United States Patent
Swamynathan et al.

(10) Patent No.: US 9,132,193 B2
(45) Date of Patent: Sep. 15, 2015

(54) USE OF SLURP1 AS AN IMUNOMODULATORY MOLECULE IN THE OCULAR SURFACE

(71) Applicants: Shivalingappa Kottur Swamynathan, Glenshaw, PA (US); Sudha Swamynathan, Glenshaw, PA (US); Kristine-Ann Gallegos Buela, Pittsburgh, PA (US); Robert Lee Hendricks, Pittsburgh, PA (US)

(72) Inventors: Shivalingappa Kottur Swamynathan, Glenshaw, PA (US); Sudha Swamynathan, Glenshaw, PA (US); Kristine-Ann Gallegos Buela, Pittsburgh, PA (US); Robert Lee Hendricks, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 40 days.

(21) Appl. No.: 14/071,559

(22) Filed: Nov. 4, 2013

(65) Prior Publication Data

US 2014/0127163 A1    May 8, 2014

Related U.S. Application Data

(60) Provisional application No. 61/722,712, filed on Nov. 5, 2012.

(51) Int. Cl.
| | |
|---|---|
| *G09B 23/28* | (2006.01) |
| *A61K 38/00* | (2006.01) |
| *A61K 39/235* | (2006.01) |
| *A61K 45/06* | (2006.01) |
| *A61K 38/17* | (2006.01) |

(52) U.S. Cl.
    CPC ............... *A61K 45/06* (2013.01); *A61K 38/177* (2013.01)

(58) Field of Classification Search
    None
    See application file for complete search history.

(56) References Cited

U.S. PATENT DOCUMENTS

| 6,277,855 | B1 * | 8/2001 | Yerxa ............................ 514/256 |
| 7,135,454 | B2 | 11/2006 | Chimienti et al. |
| 7,691,808 | B2 | 4/2010 | Chimienti et al. |
| 2007/0219130 | A1 * | 9/2007 | Chimienti et al. ............... 514/12 |
| 2010/0286065 | A1 * | 11/2010 | Lambert et al. ............... 514/20.5 |
| 2011/0098312 | A1 * | 4/2011 | Bencherif et al. ............. 514/256 |

FOREIGN PATENT DOCUMENTS

WO        WO 03077796 A2 *  9/2003

OTHER PUBLICATIONS

Sharma, Savitri. Keratitis. Bioscience Reports, 2001. 21(4):419-444.*
Norman et al., "Postnatal Gene Expression in the Normal Mouse Cornea by SAGE," *Investigative Ophthalmology & Visual Science* 45(2): 429-440 (Feb. 2004).
Swamynathan et al., "Klf4 Regulates the Expression of Slurp1, Which Functions as an Immunomodulatory Peptide in the Mouse Cornea," *Investigative Ophthalmology & Visual Science* 53(13): 8433-8446 (Dec. 2012).
Wessler and Kirkpatrick, "Acetylcholine Beyond the Neurons: The Non-Neuronal Cholinergic System in Humans," *British Journal of Pharmacology* 154(8): 1558-1571 (2008).
Norman et al., "Postnatal Gene Expression in the Normal Mouse Cornea by SAGE," *Investigative Ophthalmology & Visual Science* 45(2):429-440 (Feb. 2004).
Swamynathan, S., "Ocular Surface Expression and Functions of Slurp1," provided in a closed door presentation from *L. V. Prasad Eye Institute and Center for Cellular and Molecular Biology* in Hyderabad, India, 22 pages (Apr. 2012).
Swamynathan et al., "Klf4 Regulates the Expression of Slurp1, Which Functions as an Immunomodulatory Peptide in the Mouse Cornea," Investigative *Ophthalmology & Visual Science* 53(13):8433-8446 (Dec. 2012).

\* cited by examiner

*Primary Examiner* — Maria Leavitt
*Assistant Examiner* — Kimberly A Aron
(74) *Attorney, Agent, or Firm* — Klarquist Sparkman, LLP

(57) ABSTRACT

Methods for treating inflammation are disclosed, such as for treating ocular inflammation. In some embodiments, the ocular inflammation is inflammation of an ocular surface, such as keratitis. The methods include administering to a subject with inflammation a therapeutically effective amount of SLURP1, or a nucleic acid encoding SLURP1, thereby treating the inflammation.

21 Claims, 30 Drawing Sheets

ChIP of KLF4 bound to *SLURP1* promoter

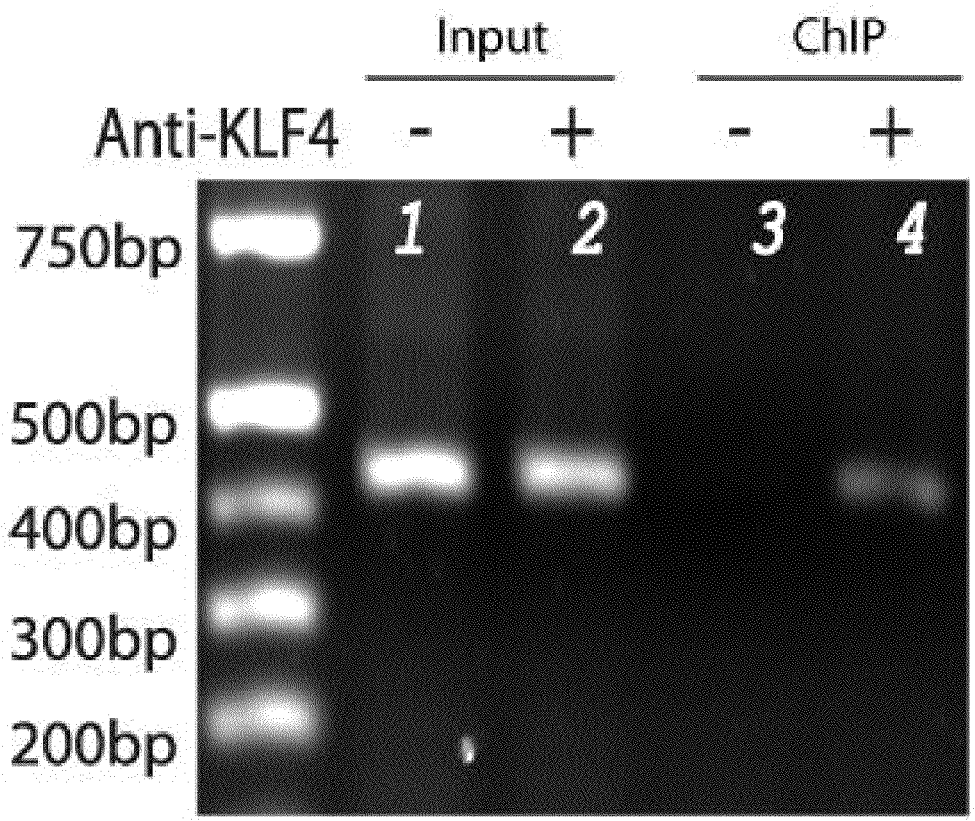

FIG. 3E

Nucleotide Sequence of *SLURP1* Proximal Promoter

```
-518 CTCACAGCAC CTATACCACA TCAGGTACTC CCTCCTTTCC ATACTGGCTC
-468 AGCCTCTACT TTGTGAGTAC ATCTGGGTGC ATAGTAGATC GGTCTTAGGC
-418 AGATGGGATA CAGTGAGGTT CCTTTTATCA GGCAGATATA AAGCAGCCTT
-368 GTACCTGAGC CTCAGGGGTT CTCGGGACCT GACTATCTGG CCTATTGGAT
-318 GCATTCACAT AGCTGAGGCA AGAGGCTCAT CTGAGAGCCA GTTGAGCCAG
-268 GCTCTAAAAG GCTTCCTCAG TTGAGGGACA GCAGAGCATG GTGTCGAGTA
-218 CTGGAGGTGC ACCAGCAGAA GCAGGACCAA GACTCCCAGA CAGAGGTTCC
-168 CCAAAAGGTC CATAGAGGGG CCCCACCCTG GGATGGTAGG TGATGATGGC
-118 TCCCATCCAC CACCCACACC CCTAGCCCTG TGCCTCCCTA CTGAGTCACT
 -68 CTGGTCCTGC CAACACCCAG AAGCCGAAGC CGGAGGCTGA GTATAAAATC
 -18 CTCACTATGA GGCCAGCCAG GGCTCCTAGC TCCTGAGCAC TGAAGAATG
                       ↑                                  ↑
              Transcription Start Site          Translation Initiation Codon
```

FIG. 3F

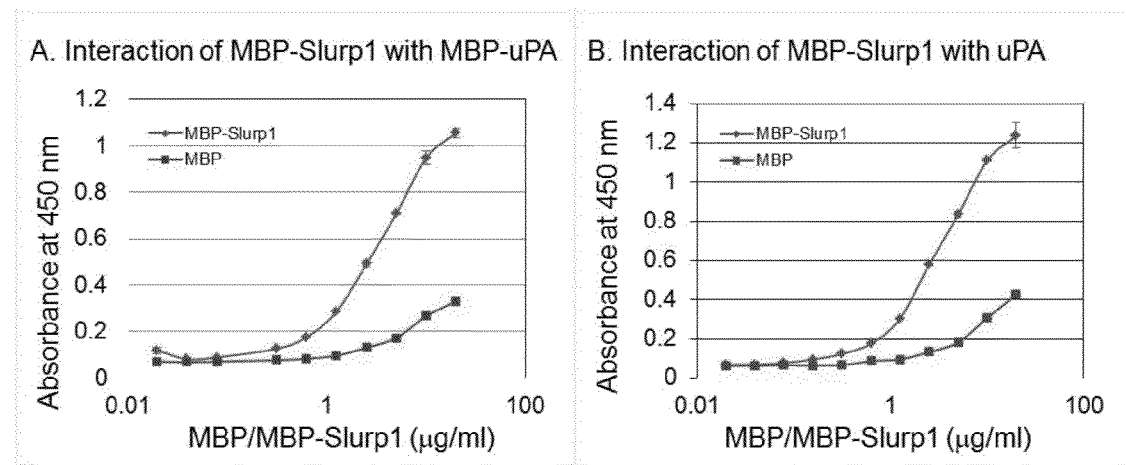
FIG. 14A  FIG. 14B
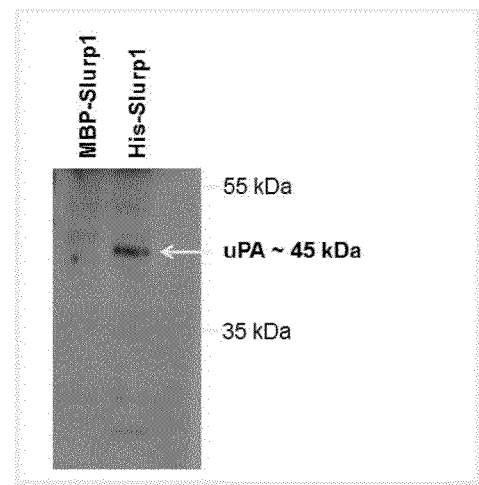
FIG. 15

USE OF SLURP1 AS AN IMUNOMODULATORY MOLECULE IN THE OCULAR SURFACE

PRIORITY CLAIM

This claims the benefit of U.S. Provisional Application No. 61/722,712, filed Nov. 5, 2012, which is incorporated herein by reference.

ACKNOWLEDGMENT OF GOVERNMENT SUPPORT

This invention was made with government support under Grant Nos. NIH EY016875, NIH EY 10359, and NIH P30EY08098 awarded by the National Eye Institute of the National Institutes of Health. The government has certain rights in the invention.

FIELD

This disclosure relates to the field of inflammatory disorders, specifically to the use of Slurp1 and agonists thereof for the treatment of ocular inflammation.

BACKGROUND

Injury, infection and allergy of the eye stimulate inflammatory reactions. Humoral and cellular immunity are involved in many external eye diseases. Inflammatory corneal disease can be infectious or non-infections, and can be vision threatening. The infectious causes of ocular inflammation are numerous, and include bacteria, viruses, fungi and parasites. The initial events of exogenous ocular infections involve microbial adherence, invasion and multiplication. Recurrent viral infections can also cause ocular inflammation.

The initial stages of ocular inflammation, such as inflammation of a surface of the eye, are often non-specific. These early manifestations include pain, warmth, redness and swelling. Common symptoms of inflammatory disease of the outer eye are itching, discomfort, dryness, redness, tearing, discharge, and blurred vision.

The most common cause of redness in the eye is conjunctival inflammation. Common causes of conjunctivitis include papillary conjunctivitis, follicular conjunctivitis, conjunctival granuloma and conjunctival ulceration. Keratitis is inflammation of the cornea. Common causes of keratitis are corneal injury, dry eye syndrome, viral infections such as adenovirus, herpes simplex, and varicella-zoster infections, bacterial infections, fungal infections, and autoimmune disorders. There is a need for methods for treating ocular inflammation, including keratitis and conjunctivitis.

SUMMARY

Methods for treating ocular inflammation are disclosed herein. In some embodiments, the methods include administering to a subject with ocular inflammation a therapeutically effective amount of Slurp1, or a nucleic acid encoding Slurp1, thereby treating the inflammation.

In some embodiments, methods are disclosed for treating the inflammation of an external surface of the eye of a subject, such as the corneal or conjunctiva, or intraocular inflammation of the anterior or posterior chamber of the eye. In particular embodiments, methods are disclosed for treating corneal inflammation such as keratitis, intraocular inflammation such as uveitis or conjunctival inflammation such as conjunctivitis in a subject.

In further embodiments, the methods include selecting a subject with ocular inflammation, and administering to the subject a therapeutically effective amount of Slurp1 polypeptide, or a polynucleotide encoding the Slurp1 polypeptide, thereby treating the subject. In some specific non-limiting examples, the subject is human. In additional non-limiting examples, the ocular inflammation is keratitis, such as keratitis caused by non-traumatic etiologies such as an infection, for example viral or bacterial infection, or inflammation caused by non-infectious means, such as trauma.

The foregoing and other objects, features, and advantages of the invention will become more apparent from the following detailed description, which proceeds with reference to the accompanying figures.

BRIEF DESCRIPTION OF THE DRAWINGS

FIG. 3A-3F. Klf4 binds and stimulates Slurp1 promoter activity. A, Schematic representation of the reporter vectors used. B, C, Relative promoter activities of different sized Slurp1 promoter fragments with increasing amounts (0, 100 or 500 ng) of co-transfected pCI-Klf4, in HCE (B) and NCTC (C) cells. D, Effect of siRNA-mediated knockdown of KLF4 on −500/+27 bp Slurp1 promoter activity in HCLE cells. Slurp1 promoter activity was reduced upon knockdown of KLF4 expression by two different siRNAs, relative to that obtained with co-transfection of control siRNA expressing plasmid. E, Chromatin immunoprecipitation was performed using HCE cells and anti-KLF4 antibody. PCR amplified SLURP1 proximal promoter fragments from the input chromatin (lanes 1-2) or immunoprecipitated chromatin (lanes 3-4) are shown. Lane 3, mock immunoprecipitated with no antibody; lane 4, immunoprecipitated with anti-KLF4 antibody. F, Nucleotide sequence of SLURP1 proximal promoter (SEQ ID NO: 7). Potential KLF4-interacting elements are shown underlined. Transcription and translation start sites are indicated.

FIGS. 14A-14B. ELISA Demonstrating Slurp1 interaction with uPA. ELISA plates were coated with partially purified maltose-binding protein (MBP) or MBP-Slurp1 fusion protein, and blocked with 5% milk. MBP-uPA fusion protein (A), or cleaved uPA (B) was layered on coated MBP or MBP-Slurp1, washed, and Slurp1-bound MBP-uPA (A) or uPA (B) detected using anti-uPA antibody. MBP-Slurp1 efficiently interacted with both MBP-uPA fusion protein (A) and cleaved, partially purified uPA (B).

FIG. 15. Pull-down assay Demonstrating Slurp1 interaction with uPA. Negative control MBP-Slurp1 (expressed in *E. coli*, purified through amylose resin) or (ii) His-Slurp1 (expressed in *E. coli*) was bound on Ni-ion resin, incubated with kidney lysate (as a source of uPA), washed thoroughly, bound proteins separated by SDS-PAGE and Slurp1-bound uPA detected by anti-uPA antibody. uPA was detected only in His-Slurp1 loaded columns, suggesting specific interaction between Slurp1 and uPA.

SEQUENCE LISTING

Figure 1A:
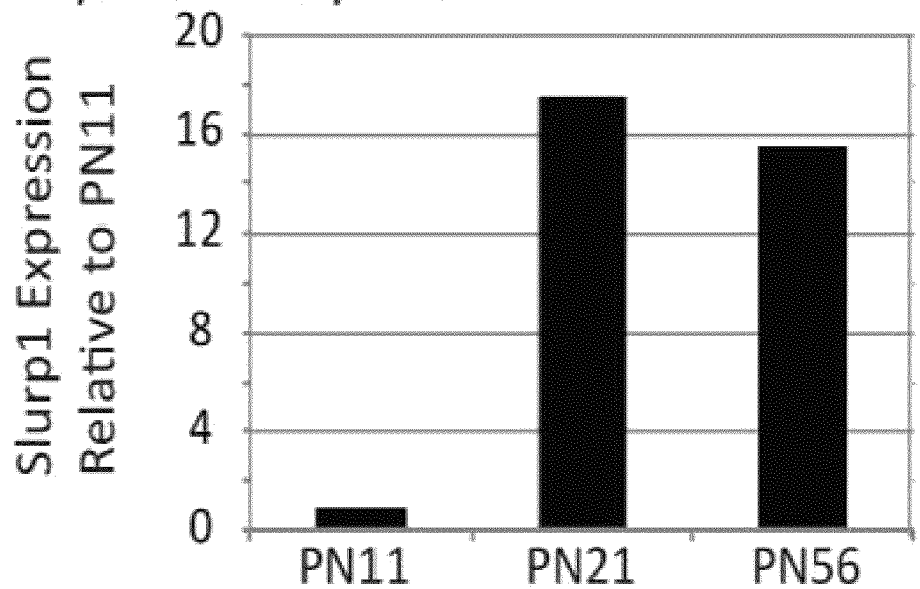
FIGS. 1A-1C. Corneal expression of Slurp1. A. QPCR demonstrating post-eyelid opening increase in Slurp1 expression Slurp1 expression increases more than 15-fold between post-natal day 11 (PN11) and PN21 B. Immunofluorescent staining of PN11, PN21 and PN56 mouse corneas showing elevated expression of Slurp1 (red) in corneal epithelium in post-eyelid opening stages. C. Immunofluorescent staining demonstrating expression of SLURP1 (green) in human corneas. Post-mortem corneal sections from a healthy 52 year-old male organ donor were used. Nuclei are stained with DAPI (blue) and corresponding 'no antibody controls' are shown in B and C. Signals emanating from the Descemet's membrane (in panel C-iv) appear to be due to autofluorescence, as they were detected in no primary antibody controls (panel C-iii) as well. Scale bars: 25 µm in B and 50 mm in C.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-90185-02_Sequence_Listing.txt, Nov. 4, 2013, 4.97 KB], which is incorporated by reference herein. In the accompanying sequence listing:

SEQ ID NO: 1 is an amino acid sequence of a human SLURP1 protein.

SEQ ID NO: 2 is an amino acid sequence of a mouse Slurp1 protein.

SEQ ID NO: 3 is an exemplary nucleic acid sequence encoding a human SLURP1 protein.

SEQ ID NO: 4 is an exemplary nucleic acid sequence encoding a murine Slurp1 protein.

SEQ ID NOs: 5-6 are primer sequences.

SEQ ID NO: 7 is the nucleic acid sequence of the SLURP proximal promoter.

DETAILED DESCRIPTION

It is disclosed herein that Slurp1 is a constitutively produced component of corneal immune privilege that inhibits leukocytic infiltration into the cornea in response to mild insults, and is rapidly down-regulated when the cornea becomes infected, permitting protective inflammation to develop. Furthermore, Slurp1, and nucleic acids encoding Slurp1, can be used to treat ocular inflammation, such as, inflammation of an ocular surface. In specific non-limiting examples, the inflammation is corneal inflammation. In other embodiments the method inhibits the migration of leukocytes into ocular surfaces, such as the cornea, conjunctiva or intraocular structures.

TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided.

Adenovirus: A virus of the family Adenoviridae, which are medium-sized (90-100 nm), nonenveloped icosahedral viruses composed of a nucleocapsid and a double-stranded linear DNA genome. The adenovirus genome is linear, non-segmented double-stranded (ds) DNA that is between 26 and 45 kb. This allows the virus to theoretically carry 22 to 40 genes. The linear dsDNA genome is able to replicate in the nucleus of mammalian cells using the host's replication machinery. However, adenoviral DNA does not integrate into the genome and is not replicated during cell division.

Adeno-associated Virus: Adeno-associated virus (AAV) is a small virus that infects humans and some other primate species. AAV is not currently known to cause disease and consequently the virus causes a very mild immune response. AAV can infect both dividing and non-dividing cells and may incorporate its genome into that of the host cell. The AAV genome is built of single-stranded deoxyribonucleic acid (ss-DNA), either positive- or negative-sensed, which is about 4.7 kilobase long. The genome comprises inverted terminal repeats (ITRs) at both ends of the DNA strand, and two open reading frames (ORFs): rep and cap. Rep is composed of four overlapping genes encoding Rep proteins required for the AAV life cycle, and Cap contains overlapping nucleotide sequences of capsid proteins: VP1, VP2 and VP3, which interact together to form a capsid of an icosahedral symmetry. For gene therapy, ITRs seem to be the only sequences required in cis next to the therapeutic gene: structural (cap) and packaging (rep) genes can be delivered in trans.

Animal: Living multi-cellular vertebrate organisms, a category that includes, for example, mammals and birds. The term mammal includes both human and non-human mammals. Similarly, the term "subject" includes both human and veterinary subjects.

Autoimmune disorder: A disorder in which the immune system produces an immune response (e.g., a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, Sjogren's syndrome, dermatomyositis, lupus erythematosus, multiple sclerosis, myasthenia gravis, Reiter's syndrome, and Grave's disease, among others.

Blepharitis: Chronic inflammation of the eyelid. Signs and symptoms that are associated with the chronic inflammation include redness of the eyelids, flaking of skin on the lids, crusting at the lid margins, generally worse on waking, cysts at the lid margin (hordeolum), red eyes, debris in the tear film, gritty sensation of the eye or foreign-body sensation, itching and eyes. The lids may become red and may have ulcerative, non-healing areas which may actually bleed. Blepharitis does not tend to cause problems with the patient's vision whatsoever, but due to a poor tear film, one may experience blurred vision.

Cornea: The transparent front part of the eye that covers the iris, pupil, and anterior chamber. Together with the lens, the cornea refracts light, and as a result helps the eye to focus, accounting for approximately two-thirds of the eye's total optical power. The cornea has unmyelinated nerve endings sensitive to touch, temperature and chemicals; a touch of the cornea causes an involuntary reflex to close the eyelid. The cornea does not have blood vessels; it receives nutrients via diffusion from the tear fluid at the outside and the aqueous humor at the inside and also from neurotrophins supplied by nerve fibers that innervate it. In humans, the cornea has a diameter of about 11.5 mm and a thickness of 0.5-0.6 mm in the center and 0.6-0.8 mm at the periphery. The cornea has five layers; from the anterior to posterior these layers are the corneal epithelium, Bowman's layer, the corneal stroma, Descemet's membrane, and the corneal endothelium.

Conjunctivitis: Inflammation of the conjunctiva, which lines the inside of the eyelids and covers the sclera. The conjunctiva is composed of non-keratinized stratified columnar epithelium with goblet cells. There are many types of conjunctivitis, including allergic conjunctivitis, bacterial conjunctivitis, viral conjunctivitis, and chemical conjunctivitis. Generally in conjunctivitis the eye appears red, but the pupils are normally reactive to light and visual acuity is unchanged.

Non-limiting example of a conjunctivitis are viral conjunctivitis, bacterial conjunctivitis, fungal conjunctivitis, parasitic conjunctivitis, or allergic conjunctivitis. Acute conjunctival inflammation is conjunctival inflammation that generally occurs for less than two weeks, 1, 2, 3, 4, 5, 6, 7, 8, 9, 10 11, 12 or 13 days or less. Chronic conjunctival inflammation is conjunctival inflammation that occurs for at least two weeks such as for 3, 4, 5, 6, 7, 8, 9, 10 weeks or more, such as for months or years.

Conjunctivitis is characterized by presence or observation of two or more (e.g., three, four, or five) of the following in a subject: an elevated number of T-lymphocytes (e.g., effector T-cells) in a conjunctiva, an elevated number of dendritic cells in a conjunctiva, an elevated number of macrophages in a conjunctiva, an elevated number of stimulated monocytes in a conjunctiva, an elevated number of natural killer cells in a conjunctiva, an elevated number of B-cells in a conjunctiva, an elevated number of eosinophils in a conjunctiva, an elevated number of mast cells in a conjunctiva, an elevated level of redness in a white of an eye or inner eyelid, pain in an eye, irritation, itchiness, burning, and/or dryness of an eye, excess tears or other discharge from an eye, difficulty opening an eyelid, blurred vision, sensitivity to light, and swelling around an eye (e.g., as compared to the levels in the same subject prior to conjunctival inflammation, a subject not having an eye disorder (a healthy subject), or a threshold value).

The detection of an elevated level of the number of immunological cells present in the conjunctiva can be accomplished using methods known in the art, such as in vivo confocal microscopy (see, e.g., Cruzat et al, Semin. Ophthalmol. 25: 171-177, 2010).

Conservative variants: "Conservative" amino acid substitutions are those substitutions that do not substantially affect or decrease an activity or antigenicity of an antigenic epitope of Brachyury. Specific, non-limiting examples of a conservative substitution include the following examples:

| Original Residue | Conservative Substitutions |
|---|---|
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |

| Original Residue | Conservative Substitutions |
|---|---|
| Tyr | Trp; Phe |
| Val | Ile; Leu |

The term conservative variant also includes the use of a substituted amino acid in place of an unsubstituted parent amino acid, provided that antibodies raised to the substituted polypeptide also immunoreact with the unsubstituted polypeptide, and/or that the substituted polypeptide retains the function of the unsubstituted polypeptide. Non-conservative substitutions are those that reduce an activity or antigenicity.

Cytokine: Proteins made by cells that affect the behavior of other cells, such as lymphocytes. In one embodiment, a cytokine is a chemokine, a molecule that affects cellular trafficking. In another embodiment, a cytokine alters the maturation of lymphocytes, and influences isotype switching by B cells.

Immunosuppressive agent: A molecule, such as a chemical compound, polypeptide small molecule, steroid, nucleic acid molecule, or other biological agent, that can decrease an immune response such as an inflammatory reaction. Immunosuppressive agents include, but are not limited to an agent of use in treating uveitis. Specific, non-limiting examples of immunosuppressive agents are corticosteroids, cyclosporine A, FK506, and anti-CD4. In additional examples, the agent is a biological response modifier, such as KINERET® (anakinra), ENBREL® (etanercept), or REMICADE® (infliximab), a disease-modifying antirheumatic drug (DMARD), such as ARAVA® (leflunomide). Agents of use to treat inflammation include non-steroidal anti-inflammatory drugs (NSAIDs), specifically a Cyclo-Oxygenase-2 (COX-2) inhibitor, such as CELEBREX® (celecoxib) and VIOXX® (rofecoxib), or another product, such as HYALGAN® (hyaluronan) and SYNVISC® (hylan G-F20).

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Inflammation: A series of local tissue reactions that take place at a site of injury and have an immunological component. The injury may be due to trauma, lack of blood supply, hemorrhage, autoimmune attack, transplanted exogenous tissue or infection. This generalized response by the body includes the release of many components of the immune system (such as cytokines), attraction of cells to the site of the damage, swelling of tissue due to the release of fluid and other processes. Inflammation can be of an infectious or a non-infectious etiology. In the eye, inflammation produces vascular dilation, fluid leakage into extra-vascular spaces, migration of leukocytes and other cells.

Infectious agent: An agent that can infect a subject, including, but not limited to, viruses, bacteria and fungi.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids and proteins.

Keratitis: An inflammation or irritation of the cornea. Typical symptoms include red eye, foreign body sensation, pain, sensitivity to light, watery eyes, and blurred vision. Keratitis is the most common cause of corneal blindness caused by infection in the United States. It can be caused by injury to the cornea, dryness and/or inflammation of the ocular surface, and infectious agents, such as herpes zoster and herpes simplex, and bacterial infections, such as *Staphylococcus aureus* and *Pseudomonas aeruginosa*. There are other forms of keratitis, such as exposure keratitis, photokeratitis caused by exposure to ultraviolet radiation, and allergic keratitis. Keratitis also can be caused by fungal infections (such as by *Fusarium*) and amoebic infections (*Acanthamoeba*). Infectious keratitis can progress rapidly, and generally requires urgent antibacterial, antifungal, or antiviral therapy to eliminate the pathogen. However, the underlying inflammation can cause persistent corneal injury (such as a scar) even after the infection or corneal trauma has been successfully treated. Corticosteroids are sometimes used to treat such inflammation but they can have undesired side effects such as increased intraocular pressure.

Superficial keratitis involves the superficial layers (the epithelium) of the cornea. Deep keratitis involves deeper layers of the cornea (including the epithelium, Bowman's Membrane and often the stroma).

Acute corneal inflammation is corneal inflammation that generally occurs for less than two weeks, such as 1, 2, 3, 4, 5, 6, 7, 8, 9, 10 11, 12 or 13 days or less. Chronic corneal inflammation is corneal inflammation that occurs for at least two weeks, such as for 3, 4, 5, 6, 7, 8, 9, 10 weeks or more, such as for months or years.

In keratitis, the presence of two or more (e.g., three, four, or five) of the following is observed in a subject: an elevated number of T-lymphocytes (e.g., effector T-cells) in a cornea, an elevated number of dendritic cells in a cornea, an elevated number of macrophages in a cornea, an elevated number of eosinophils in a cornea, an elevated number of mast cells in a cornea, an elevated number of B-cells in a cornea, an elevated number of stimulated monocytes in a cornea, an elevated number of natural killer cells in a cornea, an elevated level of redness in a cornea, pain in an eye, irritation, itchiness, burning, and/or dryness of a cornea, excess tears or other discharge from an eye, difficulty opening an eyelid, blurred vision, sensitivity to light, and swelling around the eye (e.g., as compared to the levels in the same subject prior to corneal inflammation, a subject not having an eye disorder (a healthy subject), or a threshold value). The detection of an elevated level of the number of immunological cells present in the cornea can be accomplished using methods known in the art, such as in vivo confocal microscopy (see, e.g., Cruzat et al, Semin. Ophthalmol. 25: 171-177, 2010). However, the existence of corneal inflammation also can be inferred from other underlying causes (such as trauma or infection) or the appearance of the eye (such as redness and tearing).

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Neutrophil: A type of phagocyte normally found in the blood. The nucleus has a characteristic lobed appearance, the separate lobes connected by chromatin. The nucleolus of a neutrophil disappears as the neutrophil matures. Neutrophils quickly congregate at a focus of infection, attracted by cytokines expressed by activated endothelium, mast cells, and macrophages. Neutrophils express and release cytokines, which in turn amplify inflammatory reactions by several other cell types. Neutrophils are phagocytes. For targets to be recognized, they must be coated in opsonins. Each phagocytic event resulting in the formation of a phagosome into which reactive oxygen species and hydrolytic enzymes are secreted. Neutrophils undergo a process called degranulation, wherein the contents of their granules can be released to combat infection.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intra-vitreously, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Preventing or treating a disease: "Preventing" a disease refers to inhibiting the full development of a disease, for example in a person who is known to have a predisposition to a disease such as an autoimmune disorder. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide or nucleic acid preparation is one in which the peptide, protein or nucleic acid is more enriched than the peptide, protein or nucleic acid is in its natural environment within a cell. The term purified may be used to refer to both naturally occurring and recombinant molecules. Preferably, a preparation is purified such that the protein, peptide or nucleic acid represents at least 50% of the total peptide, protein or nucleic acid content of the preparation, such as is at least about 80%, 90%, 95%, 98%, 99% or 100% of the content.

Replication defective: A viral vector that cannot further replicate and package its genomes. In one non-limiting example, when the cells of a subject are infected with a replication defective vector, a heterologous gene in the vector is expressed in the infected subject's cells. However, due to the fact that both the vector and the patient's cells lack essential genes for replication of the vector, it will not be passed on to daughter cells when the infected cell divides. Examples of essential genes for viral replication are the rev and cap genes for AAV, or gag, pol and env for a lentivirus. Generally, the genes necessary to replicate and package are not present, such that and wild-type virus cannot be formed in the subject's cells.

Secreted Ly-6/uPAR-related protein 1 (SLURP1): A protein that in humans is encoded by the SLURP1 gene. The protein encoded by this gene is a member of the Ly6/uPAR family but lacks a GPI-anchoring signal sequence. Mutations in this gene have been associated with Mal de Meleda, a rare autosomal recessive skin disorder. This gene maps to the same chromosomal region as several members of the Ly6/uPAR family of glycoprotein receptors. An exemplary human SLURP1 amino acid sequence is set forth as GENBANK Accession No. NP_065160.1, incorporated herein by reference. Additional exemplary SLURP1 amino acid sequences are provided herein.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, CABIOS 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

Therapeutic agent: Used in a generic sense, it includes treating agents, prophylactic agents, and replacement agents. SLURP1, or a polynucleotide encoding SLURP1, are forms of therapeutic agents.

Therapeutically effective amount: A quantity of an agent sufficient to achieve a desired effect in a subject being treated. For instance, this can be the amount of a SLURP1 polypeptide, or a polynucleotide encoding the SLURP1 polypeptide, sufficient to reduce inflammation, such as in the cornea, or a dose sufficient to prevent advancement, or to cause regression of a disease, or which is capable of relieving symptoms caused by a disease, such as ocular inflammation. In one example, the amount is sufficient to prevent advancement, or to cause regression of the disease. In another example, the amount is sufficient to inhibit a sign or symptom of inflammation, such as corneal inflammation, such as the presence of inflammatory cells and/or redness and/or irritation that accompanies the inflammation.

An effective amount of a SLURP1 polypeptide, or a polynucleotide encoding the SLURP1 polypeptide, can be administered systemically or locally. In addition, an effective amount of a SLURP1 polypeptide, or a polynucleotide encoding the SLURP1 polypeptide, can be administered in a single dose, or in several doses, for example daily, during a course of treatment. However, the effective amount of the SLURP1 polypeptide, or a polynucleotide encoding the SLURP1 polypeptide, will be dependent on the preparation applied, the subject being treated, the severity and type of the affliction, and the manner of administration of the compound.

The SLURP1 polypeptides, and polynucleotides encoding the SLURP1 polypeptides, disclosed herein have equal applications in medical and veterinary settings. Therefore, the general terms "subject" and "subject being treated" are understood to include all animals, including humans or other simians, dogs, cats, horses, and cows.

Uveal tract: The uveal tract is composed of three parts, the iris, the ciliary body, and the choroid. It is the middle, vascular layer of the eye, protected externally by the cornea and the sclera. It contributes to the blood supply of the retina.

The iris is the anterior section of the ciliary body. It has a relatively flat surface with an aperture in the middle called the pupil. The iris lies in contact with the lens and divides the anterior chamber from the posterior chamber. The function of the iris is to control the amount of light that enters the eye.

The ciliary body extends forward from the anterior termination of the choroid to the root of the iris. It is composed of two zones, the pars plicata and the pars plana. There are two layers of epithelium in the ciliary body, the external pigmented and an internal non-pigmented layer. The ciliary body forms the root of the iris and governs the size of the lens. Aqueous humor is secreted by the ciliary processes into the posterior chamber of the eye.

The choroid is the posterior portion of the uveal tract and the middle part of the eye, which lies between the retina and the sclera. It is largely composed of blood vessels. The function of the choroid is to nourish the outer portion of the underlying retina.

Uveitis: An intraocular inflammatory disease that includes iritis, cyclitis, panuveits, posterior uveitis and anterior uveitis. Iritis is inflammation of the iris. Cyclitis is inflammation of the ciliary body. Panuveitis refers to inflammation of the entire uveal (vascular) layer of the eye. Intermediate uveitis, also called peripheral uveitis, is centered in the area immediately behind the iris and lens in the region of the ciliary body and pars plana, and is also termed "cyclitis" and "pars planitis."

"Posterior" uveitis generally refers to chorioretinitis (inflammation of the choroid and retina). Posterior uveitis can give rise to diverse symptoms but most commonly causes floaters and decreased vision similar to intermediate uveitis. Signs include cells in the vitreous humor, white or yellow-white lesions in the retina and/or underlying choroid, exudative retinal detachments, retinal vasculitis, and optic nerve edema.

Anterior uveitis refers to iridocyclitis (inflammation of the iris and the ciliary body) and/or iritis. Anterior uveitis tends to be the most symptomatic, typically presenting with pain, redness, photophobia, and decreased vision. Signs of anterior uveitis include pupillary miosis and injections of the conjunctiva adjacent to the cornea, so-called perilimbal flush. Biomicroscopic, or slit lamp, findings include cells and flare in the aqueous humor as well as keratic precipitates, which are clumps of cells and proteinaceous material adherent to the corneal endothelium. "Diffuse" uveitis implies inflammation involving all parts of the eye, including anterior, intermediate, and posterior structures.

"Acute" uveitis is a form of uveitis in which signs and symptoms occur suddenly and last for up to about six weeks. "Chronic" uveitis is a form in which onset is gradual and lasts longer than about six weeks.

The inflammatory products (i.e., cells, fibrin, excess proteins) of ocular inflammation are commonly found in the fluid spaces of the eye, i.e., anterior chamber, posterior chamber and vitreous space as well as infiltrating the tissue imminently involved in the inflammatory response.

Uveitis may occur following surgical or traumatic injury to the eye; as a component of an autoimmune disorder (such as rheumatoid arthritis, Bechet's disease, ankylosing spondylitis, sarcoidosis), as an isolated immune mediated ocular disorder (such as pars planitis or iridocyclitis), as a disease unassociated with known etiologies, and following certain systemic diseases which cause antibody-antigen complexes to be deposited in the uveal tissues. Uveitis includes ocular inflammation associated with Bechet's disease, sarcoidosis, Vogt-Koyanagi-Harada syndrome, birdshot chorioretinopathy and sympathetic ophthalmia. Thus, non-infectious uveitis occurs in the absence of an infectious agent.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

SLURP1 Polypeptides, Polynucleotides Encoding SLURP1 and Pharmaceutical Compositions for Treatment of Ocular Inflammation Methods are disclosed herein for treating ocular inflammation. These methods disclosed herein utilize SLURP1 polypeptides and/or nucleic acids that encode SLURP1 polypeptides. An exemplary human SLURP1 protein is:
MASRWAVQLL LVAAWSMGCG EALKCYTCKE PMTSASCRTI TRCKPEDTAC MTTLVTVE-AEYPFNQSPVVT RSCSSSCVAT DPDSIGAAHL IFCCFRDLCN SEL (SEQ ID NO: 1, see GENBANK Accession No. NP_065160.1, Jun. 29, 2012, incorporated herein by reference).

An exemplary murine Slurp1 protein is
MTLRWAMWLLLLAAWSMGYGEAFRCYT-CEQPTAINSCKNIAQCKM EDTACKTV-LETVEAAFPFNHSPMVTRSCSSSCLATD-PDGIGVAHPVF CCFRDLCNSG (SEQ ID NO: 2, see GENBANK Accession No. NM_020519.1, Jun. 29, 2012, incorporated herein by reference).

In some embodiments, the SLURP1 polypeptide comprises or consists of amino acids 23-103 of the amino acid sequence set forth as SEQ ID NO: 1 or SEQ ID NO: 2. Homologs and variants, such as polypeptides about 95%, 96%, 97%, 98%, 99% identical to these polypeptides are also of use in the methods disclosed herein. In some embodiments, polypeptides 95% identical to the amino acids set forth as residues 23-103 of SEQ ID NO: 1, such as at least 95%, at least 96%, at least 97%, at least 98%, at least 99%, or 100% identical to the amino acids set forth as residues 23-103 of SEQ ID NO: 1 are of use in the methods disclosed herein. In further embodiments, the polypeptide includes at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 conservative substitutions in SEQ ID NO: 1, wherein the polypeptide retains an anti-inflammatory activity, such as reducing neutrophil infiltration in an ocular surface.

An exemplary nucleic acid encoding a human SLURP1 polypeptide is
CTCTCATCAC TTCTGAGCAC GGAGCAATGG CCTCTCGCTG GGCTGTGCAG CTGCT-GCTCGTGGCAGCCTG GAGCATGGGC TGTGGT-GAGG CCCTCAAGTG CTACACCTGC AAGGAGC-CCATGACCAGTGC TTCCTGCAGG ACCATTACCC GCTGCAAGCC AGAGGACACA GCCTGCATGACCACGCTGGT GACGGTGGAG GCAGAGTACC CCTTCAACCA GAGCCCCGTG GTGACCCGCTCCTGCTCCAG CTCCTGTGTG GCCACCGACC CCGACAGCAT CGGGGCCGCC CACCTGATCTTCTGCTGCTT CCGAGACCTC TGCAACTCGG AACTCTGAAC CCAGGGCGGC AGGGCGGAAGGTGCTCCTCA GGCACCTCCT CTCTGACGGG GCCTGGCTCC ACCTGTGATC ACCTCCCCCTGCTTCCTGCT GCTGTGGCAC AGCTCACTCA TGGGGTCTGA GGGGAGGAGAA GCACACCAGGGGCGCCCTCT GCCTTCCATA CCCCACGCTT ATAAAACATA ACTAAGCCAA (SEQ ID NO: 3, see GENBANK Accession No. NM_020427.2, Jun. 29, 2012, incorporated herein by reference).

An exemplary nucleic acid encoding mouse Slurp1 is:
AGGGCTCCTA GCTCCTGAGC ACTAAGAAT GAC-CCTTCGC TGGGCCATGT GGCTGCTGCT CTTG-GCAGCC TGGAGCATGG GCTATGGTGA GGCCT-TCCGA TGCTATACCT GTGAGCAGCC CACGGCCATT AACTCATGCA AGAATATTGC TCAGTGCAAG ATGGAAGACA CAGCCTGTAA-GACTGTACTG GAGACAGTGG AAGCAGCGTT CCCCTTCAAC CACAGTCCCA TGGTGACCCG CTCCTGCTCC AGCTCGTGTC TGGCCACCGA CCCTGATGGC ATTGGCGTTG CCCATCCTGT CTTCTGTTGC TTCCGTGACC TCTGCAACTC AGGGTTTCCA GGCTTCGTGG CAGGCCTCTA GCCACACAGG GAGCCTCCTC GTTCCTTCTC TATCCACTCT CCCGGCAGGG CCCGGTGCTG CCTGCAGTCG TCTCTACATG CCTGGATCTA TGAGCAGAGC TCACTGAGCC TCAGGTCACT CACTGTCCAC CAAGCTTGTG GAAAATAAAA TAAACCAAGG GCGAA (SEQ ID NO: 4, see GENBANK Accession No. NM_020519.12, Apr. 18, 2013, incorporated herein by reference).

Slurp1 polypeptides and polynucleotides are disclosed in U.S. Pat. No. 7,960,398 and U.S. Pat. No. 7,691,808 which are both incorporated by reference herein.

In some embodiments, the nucleic acid molecules include a nucleic acid sequence encoding an amino acid sequence at least 95% identical to the amino acids set forth as residues 23-103 of SEQ ID NO: 1, such as at least 95%, at least 96%, at least 97%, at least 98%, at least 99%, or 100% identical to the amino acids set forth as residues 23-103 of SEQ ID NO: 1. In additional embodiments, the nucleic acid molecules include a nucleic acid sequence encoding an amino acid sequence at least 95% identical to the amino acids set forth as SEQ ID NO: 1, such as at least 95%, at least 96%, at least 97%, at least 98%, at least 99%, or 100% identical to the amino acids set forth as of SEQ ID NO: 1. In further embodiments, the nucleic acid encodes a polypeptide includes at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 conservative substitutions in SEQ ID NO: 1.

These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

Nucleic acid molecules encoding SLURP1 can readily be produced by one of skill in the art, using the amino acid sequences provided herein, and the genetic code. Nucleic acid sequences encoding SLURP1 can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. Exemplary nucleic acids including sequences encoding SLURP1 can be prepared by cloning techniques.

A nucleic acid encoding a SLURP1 polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, NY, 1989). Polynucleotides also can be isolated by screening genomic or cDNA libraries with probes selected from the sequences of the desired polynucleotide under stringent hybridization conditions.

In the context of the compositions and methods described herein, a nucleic acid sequence that encodes a SLURP1 polypeptide, such as described above, is incorporated into a vector capable of expression in a host cell, using established molecular biology procedures. For example nucleic acids, such as cDNAs, that encode SLURP1 can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

Exemplary procedures sufficient to guide one of ordinary skill in the art through the production of vector capable of expression in a host cell (such as an adenoviral vector) that includes a polynucleotide sequence that encodes a SLURP1 polypeptide can be found for example in Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology*, 4th ed., Wiley & Sons, 1999.

Typically, a polynucleotide sequence encoding a SLURP1 polypeptide is operably linked to transcriptional control sequences including, for example a promoter and a polyadenylation signal. A promoter is a polynucleotide sequence recognized by the transcriptional machinery of the host cell (or introduced synthetic machinery) that is involved in the initiation of transcription. A polyadenylation signal is a polynucleotide sequence that directs the addition of a series of nucleotides on the end of the mRNA transcript for proper processing and trafficking of the transcript out of the nucleus into the cytoplasm for translation.

Exemplary promoters include viral promoters, such as cytomegalovirus immediate early gene promoter ("CMV"), herpes simplex virus thymidine kinase ("tk"), SV40 early transcription unit, polyoma, retroviruses, papilloma virus, hepatitis B virus, and human and simian immunodeficiency viruses. Other promoters are isolated from mammalian genes, including the immunoglobulin heavy chain, immunoglobulin light chain, T-cell receptor, HLA DQ α and DQ β, β-interferon, interleukin-2, interleukin-2 receptor, MHC class II, HLA-DRα, β-actin, muscle creatine kinase, prealbumin (transthyretin), elastase I, metallothionein, collagenase, albumin, fetoprotein, β-globin, c-fos, c-HA-ras, insulin, neural cell adhesion molecule (NCAM), α1-antitrypsin, H2B (TH2B) histone, type I collagen, glucose-regulated proteins (GRP94 and GRP78), rat growth hormone, human serum amyloid A (SAA), troponin I (TNI), platelet-derived growth factor, and dystrophin, and promoters specific for keratinocytes, and epithelial cells.

The promoter can be either inducible or constitutive. An inducible promoter is a promoter which is inactive or exhibits low activity except in the presence of an inducer substance. Examples of inducible promoters include, but are not limited to, MT II, MMTV, collagenase, stromelysin, SV40, murine MX gene, α-2-macroglobulin, MHC class I gene h-2 kb, HSP70, proliferin, tumor necrosis factor, or thyroid stimulating hormone gene promoter.

Typically, the promoter is a constitutive promoter that results in high levels of transcription upon introduction into a host cell in the absence of additional factors. Optionally, the transcription control sequences include one or more enhancer elements, which are binding recognition sites for one or more transcription factors that increase transcription above that observed for the minimal promoter alone.

It may be desirable to include a polyadenylation signal to effect proper termination and polyadenylation of the gene transcript. Exemplary polyadenylation signals have been isolated from bovine growth hormone, SV40 and the herpes simplex virus thymidine kinase genes. Any of these or other polyadenylation signals can be utilized in the context of the adenovirus vectors described herein.

The polynucleotides encoding a SLURP1 polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

Viral vectors can also be prepared encoding the SLURP1 polypeptides. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a SLURP1 polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus, yeast and the like.

Adenovirus vectors (Ad) vectors can be produced that encode a SLURP1 polypeptide and are of use in the methods disclosed herein. These vectors are of use in the methods disclosed herein, including replication competent, replication deficient, gutless forms thereof, and adeno-associated virus (AAV) vectors. Without being bound by theory, adenovirus vectors are known to exhibit strong expression in vitro, excellent titer, and the ability to transduce dividing and non-dividing cells in vivo (Hitt et al., Adv in Virus Res 55:479-505, 2000). When used in vivo these vectors lead to strong but transient gene expression due to immune responses elicited to the vector backbone.

Adenoviral vectors are often constructed by insertion of a nucleic acid encoding a SLURP1 polypeptide in place of, or in the middle of, essential viral sequences such as those found at the E1 region of adenovirus (Berkner, BioTechniques, 6:616-629, 1988; Graham et al., Methods in Molecular Biology, 7:109-128, Ed: Murcy, The Human Press Inc., 1991). Inactivation of essential viral genes by, for example, deletion or insertion, disables the adenovirus' ability to replicate. To propagate such vectors in cell culture, the deleted genes must be provided in trans (for example, the E1A and E1B proteins in the case of an E1 delete vector). These replication-defective adenoviruses are produced in packaging cells engineered to complement the replication-incompetent virus by expressing the subset of genetic elements deleted from their viral genome. Potential sites for the insertion of a nucleic acid of interest, such as a nucleic acid encoding a SLURP1 polypeptide, in recombinant adenoviral vectors include, without limitation, the E1, E2, E3 and the E4 region. In some embodiments, a recombinant adenoviral vector is produced from a human adenovirus that has the E1 region deleted and replaced with a nucleic acid encoding a SLURP1 polypeptide. The resulting viral vector, with one or more of its essential genes inactivated, is replication defective (Statford-Perricaudet et al., Human Gene Therapy, 1:241-256, 1990).

The recombinant adenovirus vectors can include: (1) a packaging site enabling the vector to be incorporated into replication-defective Ad virions; and (2) the nucleic acid encoding the SLURP1 polypeptide. Other elements of use for incorporation into infectious virions, include the 5' and 3' Ad ITRs; the E2 and E3 genes can be included in the vector. In some embodiments, a nucleic acid encoding a SLURP1 polypeptide is inserted into adenovirus in the deleted E1A, E1B or E3 region of the virus genome. In some embodiments, the adenovirus vectors do not express one or more wild-type adenovirus gene products, such as E1a, E1b, E2, E3, E4. In some non-limiting examples, virions are typically used together with packaging cell lines that complement the functions of E1, E2A, E4 and optionally the E3 gene regions (see, for example, U.S. Pat. Nos. 5,872,005, 5,994,106, 6,133,028 and 6,127,175, incorporated by reference herein in their entirety). Adenovirus vectors can be purified and formulated using techniques known in the art.

In some embodiments, packaging cell lines such as the human embryonic kidney 293 ("HEK-293" or "293") cell line (Graham et al., J. Gen. Virol., 36:59-72, 1977) or human embryonic retinoblast ("HER-911" or "911") cell line (Fallaux et al., Hum. Gene Ther., 7:215-222, 1996), provide in trans the missing region, such as the E1 region, so that the deleted or modified adenoviral vector can replicate in such cells. Suitable adenoviral vectors are disclosed, for example, in U.S. Patent Publication No. 20080193484, which is incorporated herein by reference. Replication-defective adenovirus virions encapsulating the recombinant adenovirus vectors can be made by standard techniques known in the art using packaging cells and packaging technology. Examples of these methods can be found, for example, in U.S. Pat. No. 5,872,005, incorporated herein by reference in its entirety.

Recombinant AAV vectors are characterized in that they are capable of directing the expression and the production of the selected transgenic products in targeted cells. Thus, the recombinant vectors comprise at least all of the sequences of AAV essential for encapsidation and the physical structures for infection of target cells.

Recombinant AAV (rAAV) virions can be constructed such that they include, as operatively linked components in the direction of transcription, control sequences including transcriptional initiation and termination sequences, and the nucleic acid encoding the SLURP1 polypeptide. These components are bounded on the 5' and 3' end by functional AAV inverted terminal repeat (ITR) sequences. By "functional AAV ITR sequences" is meant that the ITR sequences function as intended for the rescue, replication and packaging of the AAV virion. Hence, AAV ITRs for use in the vectors need not have a wild-type nucleotide sequence, and can be altered by the insertion, deletion or substitution of nucleotides, or the AAV ITRs can be derived from any of several AAV serotypes, provided they are functional. An AAV vector is a vector derived from an adeno-associated virus serotype, including without limitation, AAV-1, AAV-2, AAV-3, AAV-4, AAV-5, AAV-6, AAV-7, AAV-8, etc. In some embodiments, the AAV vectors have the wild type REP and CAP genes deleted in whole or part, but retain functional flanking ITR sequences. These vectors can all be used, without limitation, for the expression of a Slurp1 polypeptide.

It is understood that portions of the nucleic acid sequences encoding SLURP1 polypeptides can be deleted as long as the polypeptides are functionally active. For example, it may be desirable to delete one or more amino acids from the N-terminus, C-terminus, or both. It is also contemplated that the substitution of residues in the disclosed SLURP1 polypeptides can be made, for example conservative substitutions, such that the ability of the functionality of the SLURP1 polypeptides is maintained.

The SLURP1 polypeptide, or a polynucleotide encoding the SLURP1 polypeptide, described herein can be formulated in a variety of ways depending on the location and type of disease to be treated. Pharmaceutical compositions are thus provided for both local use (for example, topical or within an ocular transplant), as well as for systemic use. The subject can be any subject, such as a mammalian subject. Therefore, the disclosure includes within its scope pharmaceutical compositions comprising at least one SLURP1 polypeptide, or a polynucleotide encoding the SLURP1 polypeptide, formulated for use in human or veterinary medicine. Any of these compositions are of use in the methods disclosed herein.

The SLURP1 polypeptides and nucleic acids encoding SLURP1 polypeptides can be administered ex vivo (such as into a stem cell to be implanted into the eye) or in vivo to a cell or subject. Generally, it is desirable to prepare the compositions as pharmaceutical compositions appropriate for the intended application. Accordingly, methods for making a medicament or pharmaceutical composition containing the polypeptides, nucleic acids, or vectors described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the polypeptide, nucleic acid, or dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Administration of therapeutic compositions can be by any common route as long as the target tissue (typically, the ocular surface) is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. In some embodiments, the SLURP1 polypeptide or the polynucleotide encoding the SLURP1 polypeptide is formulated for administration to the eye, such as to the cornea, uveal tract, or conjunctiva. Such pharmaceutical compositions are usually administered as pharmaceutically acceptable compositions that include physiologically acceptable carriers, buffers or other excipients. Pharmaceutical compositions that include SLURP1, and/or a polynucleotide encoding SLURP1, as an active ingredient, can be formulated with an appropriate solid or liquid carrier, depending upon the particular mode of administration chosen.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Eye drops or sprays can be provided in unit dose dispensers (such as eye drop bottles that dispense a metered unit dose that contains the SLURP1 polypeptide, or polynucleotide encoding the SLURP1 polypeptide, either alone or in combination with other therapeutic agents such as corticosteroids). Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art. Implants can also be employed (see below).

The pharmaceutical compositions that include a SLURP1 polypeptide, or a nucleic acid encoding the SLURP1 polypeptide, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The SLURP1 polypeptide, or a nucleic acid encoding the SLURP1 polypeptide can be included in an inert matrix for either topical application or injection into the eye, such as for intra-vitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including a SLURP1 polypeptide, or a nucleic acid encoding the SLURP1 polypeptide can be applied topically, either in the form of drops or as an aqueous based cream, or can be injected intraocularly. In a formulation for topical application, the SLURP1 polypeptide, or a nucleic acid encoding the SLURP1 polypeptide is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the SLURP1 polypeptide, or a nucleic acid encoding the SLURP1 polypeptide, over time. In one example, the SLURP1 polypeptide, or a nucleic acid encoding the SLURP1 polypeptide, can be dissolved in an organic solvent such as DMSO or alcohol as previously described and contain a polyanhydride, poly(glycolic) acid, poly(lactic) acid, or polycaprolactone polymer.

The SLURP1 polypeptide, or a nucleic acid encoding the SLURP1 polypeptide, can be included in a delivery system that can be implanted at various sites in the eye, depending on the size, shape and formulation of the implant, and the type of transplant procedure. The SLURP1 polypeptide, or a nucleic acid encoding the SLURP1 polypeptide, can be used alone. However, in another embodiment, at least one additional agent, such as at least one agent that is disclosed below, can be included along with the SLURP1 polypeptide, or a nucleic acid encoding the SLURP1 polypeptide, in the delivery system, such as in an implant. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera. In one example, the delivery system is placed in the anterior chamber of the eye. In another example, the delivery system is placed in the vitreous cavity.

The implants can be inserted into the eye by a variety of methods, including placement by forceps or by trocar following making an incision in the sclera (for example, a 2-3 mm incision) or other suitable site. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of SLURP1 polypeptide, or a nucleic acid encoding the SLURP1 polypeptide, surrounding the device, and thus influence the release rates (for example, a device placed closer to the edge of the vitreous may result in a slower release rate, see U.S. Pat. No. 5,869,079 and U.S. Pat. No. 6,699,493).

The use of implants is well known in the art (see U.S. Pat. No. 6,699,493 and U.S. Pat. No. 5,869,079). In one embodiment, an implant is formulated with the SLURP1 polypeptide, or a nucleic acid encoding the SLURP1 polypeptide, associated with a bioerodible polymer matrix.

Generally, when implants are used, the SLURP1 polypeptide, or nucleic acid encoding the SLURP1 polypeptide, is homogeneously distributed through the polymeric matrix, such that it is distributed evenly enough that no detrimental fluctuations in rate of release occur because of uneven distribution of the immunosuppressive agent in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493).

The SLURP1 polypeptides and polynucleotides disclosed herein can be formulated in an implantable form with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, sodium bicarbonate. These agents can be present in amounts sufficient to maintain a pH of the system of between about 2 to about 9 such as about 4 to about 8, or at about 6 to about 7. In one example, the pH of the system is maintained at about 7. As such, the buffering agent can be as much as 5% on a weight-to-weight basis of the total composition. Electrolytes such as sodium chloride and potassium chloride may also be included in the formulation. The proportions of suppressive ODN, polymer, and any other modifiers may be empirically determined by formulating several implants with varying proportions. A USP approved method for dissolution or release test can be used to measure the rate of release (USP 23; NF 18 (1995) pp. 1790-1798). The implant sizes and shape can also be varied for use in particular regions of the eye (see U.S. Pat. No. 5,869,079).

The SLURP1 polypeptides, and polynucleotide encoding these polypeptides, can be included in a contact lens, such as a bandage lens, for treating corneal inflammation in a subject. The contact lens includes a contact lens substrate and a coating provided on at least a portion of the substrate, or within the matrix of the lens material. The coating can include an amount of SLURP1 polypeptide effective to treat corneal inflammation in a subject upon administration of the contact lens to the subject. Coatings including the therapeutic agent can be applied to a number of contact lens substrate materials known in the art. Virtually any substrate known in the art that can be fashioned into a contact lens can be used provided it is optically transparent.

In some embodiments, the substrate can include optically transparent materials that allow oxygen to reach the cornea in an amount, which is sufficient for long-term corneal health. Examples of substrates include polymers made from hydrophobic materials, such as silicone copolymers, interpolymers, oligomers, and macromers. Illustrative polysilicones are polydimethyl siloxane, polydimethyl-co-vinylmethylsiloxane. Other silicones include silicone rubbers described in U.S. Pat. No. 3,228,741; U.S. Pat. No. 3,341,490; U.S. Pat. No. 3,518,324. Substrates described in U.S. Pat. No. 4,136,250; U.S. Pat. No. 5,387,623; U.S. Pat. No. 5,760,100; U.S. Pat. No. 5,789,461; U.S. Pat. No. 5,776,999; U.S. Pat. No. 5,849,811; U.S. Pat. No. 5,314,960 and U.S. Pat. No. 5,244,981 can also be used. Cross-linked polymers of propoxylate of methyl glucose and propylene oxide and HEMA-based hydrogels can also be used as substrates of the contact lens.

Silicone compositions that can be used in forming the contact lens are the cross-linked polysiloxanes obtained by cross-linking siloxane prepolymers by means of hydrosilylation, co-condensation and by free radical mechanisms as in U.S. Pat. No. 4,143,949. Additional silicone-based substrates are cross-linked polymers of α omega.-bisamionpropyl polydimethylsiloxane, and gylycidyl methacrylate, cross-linked polymers. Silicone compositions can also be made from combining a methacrylate with one or more silicone monomers in the presence of a group transfer polymerization (GTP) catalyst to form a macromer that is subsequently polymerized with other monomers to give the final substrate. Substrates described in U.S. Pat. No. 6,951,894 are also suitable for use in the present invention.

The therapeutic agent can be prepared and applied to the contact lens as an aqueous solution, suspension, or colloid and then applied to the contact lens substrate according to any process that can provide the coating in contact with the substrate or cause the therapeutic agent to be absorbed within the contact lens. For example, processes for applying the coating to the substrate include immersion, spraying, brushing, and spin coating. Once the lens substrate is coated it may be subjected to any number of additional steps that are conducted in the manufacture of contact lenses. These can include, for example, swelling and washing steps, the addition of additives such as surfactants, and extraction steps, amongst others. The solution including the SLURP1 polypeptide, or a nucleic acid encoding this polypeptide, can adhere to the contact lens by, for example, chemical bonding, such as covalent or ionic bonding, or physical bonding. In some aspects, the coating is released from the lens substrate throughout its useful life (such as storage time plus the time in which it will be in contact with a user's eye).

The contact lens can also include more than one layer of coating. This can be desirable where the coating layer will provide the requisite surface properties (e.g. treatment of corneal inflammation) but is not particularly compatible with the lens substrate itself. For example, a tie-layer or coupling agent can be used to adhere the coating to the substrate. Selections of compatible lens substrate, therapeutic coating, and tie-layer (if necessary) materials is well within the knowledge of one skilled in the art. Generally, the contact lens is non-toxic to the subject's cornea and other tissue while providing for the treatment of corneal inflammation in the subject.

The SLURP1 polypeptide, and/or a polynucleotide encoding the SLURP1 polypeptide described herein can be formulated with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, sodium bicarbonate. These agents can be present in amounts sufficient to maintain a pH of the system of between about 2 to about 9 such as about 4 to about 8, or at about 6 to about 7. In one example, the pH of the system is maintained at about 7. As such, the buffering agent can be as much as 5% on a weight-to-weight basis of the total composition. Electrolytes such as sodium chloride and potassium chloride may also be included in the formulation. The proportions of SLURP1 polypeptide, and/or a polynucleotide encoding the SLURP1 polypeptide, polymer, and any other modifiers may be empirically determined by formulating several implants with varying proportions. A USP approved method for dissolution or release test can be used to measure the rate of release (USP 23; NF 18 (1995) pp. 1790-1798). Implant sizes and shape can also be varied for use in particular regions of the eye (see U.S. Pat. No. 5,869,079).

The SLURP1 polypeptide, and/or a polynucleotide encoding the SLURP1 polypeptide can be formulated with additional therapeutic agents. Exemplary agents include cyclosporine, FK506, steroids such as hydrocortisone, antibodies (such as anti-CD4 or antibodies that specifically bind the IL-2 receptor), cytokines (such as beta-interferon), or non-steroidal anti-inflammatory agents. Additional agents include antibiotics, such as minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefminox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofurantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol).

Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, sapercon azole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, Tomudex®, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be included such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lornoxicam, piroxicam, tenoxicam), .epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Additional Treatment Methods

Methods of treating a subject with ocular inflammation are disclosed herein. The methods include selecting a subject with ocular inflammation, and administering to the subject a therapeutically effective amount of a SLURP1 polypeptide or a nucleic acid encoding the SLURP1 polypeptide. Any of the compositions disclosed herein can be used in these methods.

In some embodiments, methods of treating ocular inflammation are provided. In some embodiments, the corneal inflammation treated by the methods disclosed herein are related to ocular disease or an ophthalmic disorder, such as uveitis, scleritis, episcleritis, keratitis, ocular or ophthalmic surgery (e.g., cornea surgery), endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, pterygium, and contact lens wear-induced conditions, such as a peripheral ulcer. The ocular inflammation can be inflammation of an external surface of the eye, such as, but not limited to, the cornea, conjunctiva or eye lid.

In some examples, the ocular inflammation results from laser eye therapy. In other examples, the ocular inflammation results from trauma. In further examples, the ocular inflammation results from exposure to ultraviolet light. In yet other examples, the ocular inflammation results from exposure to chemical stimuli or a toxin. In additional examples, the ocular inflammation results from a condition selected from the group consisting of Mal de Meleda, allergic conjunctivitis, Reiter's disease, scleritis, iridocyclitis, uveitis, Vogt-Koyanagi syndrome, photophthalmia, nongranulomatous inflammation of the uveal tract, granulomatous inflammation of the uveal tract, necrosis of neoplasms, foreign particles lodged in the eye, retinal light toxicity and retinal edema from light exposure. In yet other examples, the ocular inflammation is the result of an infection, such as a viral, bacterial or fungal infection.

The ocular inflammation can be keratitis. In other embodiments, the methods can be used to treat keratitis related to microbial infection. In one specific non-liming example, methods are provided for treating keratitis caused by various microbial infections such as gram-negative bacteria (*P. aeruginosa* and *S. marcesans*), gram positive bacteria (for example, *S. aureus, S. epidermidis* and *Corynebacterium* species (*P. acnes*)). In some embodiments, the keratitis is caused by gram positive cocci, gram negative bacilli, gram negative coccobacilli, gram positive bacilli, spirochetes, mycobacteria, or actinomycetes. Therefore, methods are provided for treating inflammation of the cornea associated with bacterial keratitis. In other embodiments, methods are provided for treating keratitis caused by a virus, such as an adenovirus, a herpes virus, a poxvirus, or a rubeola virus. Methods are also provided to treat inflammation of the cornea as a result of a fungal infection. More specifically, the methods disclosed herein can be used to treat corneal inflammation caused by an infection with, for example, *Fusarium, Penicillium, Aspergillus, Cephalosporium (Acremonium), Trichophyton, Microsporum, Epidermophyton, Scopulariopsis*, and *Candida*. Methods are also provided for the treatment of inflammation of the cornea from infection with parasites, such as *Onchocerca volvulus, Acanthamoeba casterllani, Acantomoeba polyphagia, Leishmania brasillensis, Onchocerca volvulus*, or *Trypanosoma* sp.

The methods described herein also can be used to treat sterile keratitis in which no living organisms are recovered from either a contact lens or the corneal surface. In some embodiments, the corneal inflammation is from ultraviolet light or other environmental exposure, trauma, or dry eye. The corneal inflammation can be the result of an autoimmune disease, such as Fuch's superficial marginal keratitis, rheumatoid arthritis, systemic lupus erythematosus, clearoderma, Wegner's granulomatosis, polyarteritis nodosa, relapsing polychondritis, Behcet syndrome, or inflammatory bowel disease.

In additional embodiments, keratitis can be treated in a subject, wherein the inflammation is associated with contact lens wear. These syndromes can include, but are not limited to Contact Lens Associated Corneal Infiltrates (CLACI), Contact Lens Associated Red Eye (CLARE), Contact Lens Peripheral Ulcer (CPLU). Sterile and infectious infiltrates can usually, but not always, be distinguished by slit lamp examination by those having ordinary skill in the art.

Methods are also provided for treating conjunctivitis. The conjunctivitis can be conjunctivitis from an infectious agent, such as a virus. Viral conjunctivitis can be caused by an adenovirus, a herpes simplex virus, an enterovirus or a coxsackievirus, amongst others. Bacterial conjunctivitis can be caused by *S. aureus, S. pneumoniae* or *H. influenzae*, amongst others. The conjunctivitis can be caused by *N. gonorrhoeae* or *N. meningitidis*.

In specific non-limiting examples, the conjunctivitis is chronic bacterial conjunctivitis, such as conjunctivitis caused by *S. aureus, M. lacunata* or other gram-negative enteric bacteria. The conjunctivitis can be associated with blepharitis.

The conjunctivitis can be chemically induced, such as from the introduction of an irritant, for example from the introduction of an acid or alkali substance into the eye. The conjunctivitis can be allergic conjunctivitis. Methods are also provided for treating blepharoconjunctivitis and keratoconjunctivitis. In specific non-limiting examples the keratoconjunctivitis is keratoconjunctivitis sicca, vernal keratoconjunctivitis, atopic keratoconjunctivitis, infectious bovine keratoconjunctivitis, superior limbic keratoconjunctivitis, or keratoconjunctivitis photoelectrica.

The ocular inflammation can be blepharitis. In specific non-limiting examples, the blepharitis is seborrhoeic, staphylococcal, mixed, posterior or meibomitis, or parasitic. The blepharitis can be posterior blepharitis or anterior blepharitis.

In other embodiments, the ocular inflammation can be uveitis. Thus, a method is disclosed herein for the treatment of uveitis in a subject by administering a therapeutically effective amount of SLURP1 or a nucleic acid encoding SLURP1, thereby treating the subject. Any form of uveitis can be treated using SLURP1 or a nucleic acid encoding Slurp1. For example, iritis, cyclitis, panuveits, iridocyclitis, posterior uveitis, anterior uveitis and diffuse uveitis can be treated using the methods disclosed herein. Anterior and/or posterior uveitis can be treated using Slurp1 or a nucleic acid encoding Slurp1. Both acute onset uveitis and chronic uveitis also can be treated.

In one embodiment, a method is provided for treating anterior uveitis in a subject. Subjects can be treated that are affected with idiopathic iridocyclitis, HLA-B27 positive iridocyclitis, uveitis associated with juvenile rheumatoid arthritis, Fuch's heterochromatice iridocyclitis, herpes simplex keatovueitis, ankylosing spondylitis, intraocular lens related uveitis, Reiter's syndrome, Herpes zoster keratouveitis, uveitis associated with syphilis, traumatic iridocyclitis, uveitis associated with inflammatory bowel disease, tuberculosis iridocyclitis.

In another embodiment, a method is provided for treating posterior uveitis in a subject. Thus subjects can be treated that are affected with toxoplasma retinochroiditis, retinal vasculitis, idiopathic posterior uveitis, ocular histoplasmosis, toxocariasis, cytomegalovirus retinitis, idiopathic retinitis, serpinous choroidopathy, acute multifocal placoid, pigment eptitheliopathy, acute retinal necrosis, bird shot choroidopathy, uveitis associated with a leukemia or a lymphoma, reticulum cell sarcoma, ocular candidiasis, tuberculous uveitis, lupus retinitis.

In a further embodiment, a method is provided for treating diffuse uveitis. Thus, subjects can be treated that are affected with sarcoidosis, syphilis, Vogt-Koyanagi-Harada syndrome, or Bechet's disease.

In one embodiment, a sign or a symptom of the uveitis is decreased or alleviated. Ocular signs include ciliary injection, aqueous flare, the accumulation of cells visible on ophthalmic examination, such as aqueous cells, retrolental cells, and vitreous cells, keratic precipitates, and hypema. Symptoms include pain (such as ciliary spasm), redness, photophobia, increased lacrimation, and decreased vision. One of skill in the art can readily diagnose uveitis. In one embodiment, biomicroscopy (for example, a "slit lamp") is used to diagnose uveitis, to evaluate the clinical course of the disease or to verify that a treatment protocol has been successful.

In additional embodiments, the subject can be administered an additional pharmaceutical agent, such as a steroidal or non-steroidal anti-inflammatory agent, anti-bacterial agents, anti-fungal agents, or anti-neoplastic agent. The phrase "combinatorial therapy" or "combination therapy" embraces the administration of a SLURP1 polypeptide and/or a nucleic acid encoding the SLURP1 polypeptide, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, topical administration, oral routes, intravenous routes, intramuscular routes, and direct absorption through mucous membrane tissue. The therapeutic agents can be administered by the same route or by different routes. Any of the compositions disclosed above can be used in the presently claimed methods.

In some embodiments, combinational therapy can include the administration of a SLURP1 polypeptide, and/or a nucleic acid encoding the SLURP1 polypeptide, with at least one antibacterial, antiviral or antifungal agent, such as to treat ocular inflammation, such as corneal inflammation. In one specific example, the combinational therapy includes a SLURP1 polypeptide, and/or a nucleic acid encoding the SLURP1 polypeptide, and at least one ophthalmic antibiotic or ophthalmic antiviral. Ophthalmic antibiotics include, for example, chloramphenicol sodium succinate ophthalmic (chlorampenical); CORTISPORIN® (neomycin and polymyxin β sulfates and hydrocortisone acetate cream); ILOTYCIN® (erythromycin ophthalmic ointment); NEODECADRON® (neomycin sulfate-dexamethasone sodium phosphate); POLYTRIM® (trimethoprim and polythyxin-.beta. sulfate ophthalmic solution); TERRA-CORTRIL® (oxytetracycline HCL and hydrocortisone acetate); TERRA- MYCIN® (oxytetracycline); and TOBRADEX® (tobramycin and dexamethosone ophthalmic suspension and ointment). Ophthalmic antivirals include, for example, VIRA-A® ophthalmic ointment, (vidarabine). Ophthalmic quinalones include, for example, CHIBROXIN® (norfloxacin ophthalmic solution); CILOXAN® ophthalmic solution, (Ciprofloxacin HCL); and OCUFLOX® ophthalmic solution (ofloxacin). Ophthalmic sulfonamides include, for example, BLEPHAMIDE® ophthalmic ointment (sulfacetamide sodium and prednisolone acetate); and BLEPHAMIDE® ophthalmic suspension (sulfacetamide sodium and prednisolone acetate). Antifungals include, for example, natamycin and amphotericin-B.

Methods are provided for treating an inflammatory response in a subject's eye, such as in the cornea, conjunctiva, eye lid, or uveal tract. The method includes administering to the subject a therapeutically effective amount of a SLURP1 polypeptide, and/or a nucleic acid encoding the SLURP1 polypeptide. In one aspect of the present invention, the treatment can result in the inhibition of cellular infiltrate into the subject's cornea. More particularly, the treatment of the inflammatory response can include the inhibition of neutrophil infiltration. In some embodiments, neutrophil infiltration is reduced by at least about 30%, about 35%, about 40%, about 45%, about 50%, about 55%, about 60%, about 65%, about 70%, about 75%, about 80%, about 85%, about 90%, or about 95%.

For any of the methods disclosed herein, the SLURP1 polypeptide, or polynucleotide encoding the SLURP1 polypeptide, can be administered systemically or locally. In some embodiments, the SLURP1 polypeptide, or polynucleotide encoding the SLURP1 polypeptide, is administered locally to the eye. The administration can be topical, such as in an ophthalmic solution or ointment, or in a contact lens placed in the eye. The SLURP1 polypeptide, or polynucleotide encoding the SLURP1 polypeptide, can be included in an implant that is implanted in the eye. However, administration can also be systemic.

The SLURP1 polypeptide, or a nucleic acid encoding the SLURP1 polypeptide, is delivered for a sufficient time period to achieve the desired effect. Thus, in one embodiment, the SLURP1 polypeptide, or a nucleic acid encoding the SLURP1 polypeptide, is delivered for at least about 2 days, such as for about five days, seven days, ten days, 14 or 21 days. In several embodiments, the SLURP1 polypeptide, or a nucleic acid encoding the SLURP1 polypeptide, is delivered for at least about one week, at least about two weeks, at least about three weeks, at least about four weeks, at least about five weeks, at least about six weeks, at least about seven weeks, at least about eight weeks, at least about nine weeks, at least about 10 weeks, and at least about 12 weeks. The duration of use of a SLURP1 polypeptide, or a nucleic acid encoding the SLURP1 polypeptide, can be the medical history of the subject and other contributing factors (such as use of other agents, etc.). If extended periods of administration are required, the SLURP1 polypeptide, or a nucleic acid encoding the SLURP1 polypeptide, can be administered for up to six months, or one year, or longer. In one embodiment, extended periods of delivery are achieved with the use of an implant or a contact lens (see above). Thus, administration can be continuous or repeated.

Any of the administration methods and/or compositions disclosed above can be utilized. More than one method of administration also can also be utilized, such as a combination of instillation methods. For example, implants can be sequentially implanted into the vitreous in order to maintain concentrations for even long periods. In one embodiment, more than one implant can be sequentially implanted into the eye in order to maintain therapeutic drug concentrations for longer periods. Implants or contact lens can be combined with ophthalmic solutions or ointments. Topical administration can also be combined with systemic administration.

In one embodiment, a sign or a symptom of the inflammation, such as corneal inflammation is decreased or alleviated. Administration can be systemic or local. One polypeptide or polynucleotides, or multiple polypeptides and polynucleotides can be utilized.

EXAMPLES

The secreted Ly-6/urokinase plasminogen activator receptor-related protein-1 (SLURP1) belongs to the Ly6/uPAR superfamily of proteins that participate in signal transduction, immune activation and cell adhesion and are characterized by the presence of three-finger structure generated by five disulfide bridges (Grando et al., *J Pharmacol Sci* 2008; 106:174-179, Mazar et al., *Clin Cancer Res* 2008; 14:5649-5655, Adermann et al., *Protein Sci* 1999; 8:810-819)

SLURP1 is expressed in a variety of cells including immune cells (Moriwaki et al., *Life Sci* 2007; 80:2365-2368, bronchial epithelial cells, (Horiguchi et al., *J Neurosci Res* 2009; 87:2740-2747) primary sensory neurons (Moriwaki et al., *Neurosci Res* 2009; 64:403-412), the skin, exocervix, gums, stomach, trachea and esophagus (Mastrangeli et al., *Eur J Dermatol* 2003; 13:560-570), oral keratinocytes (Arredondo et al., *Life Sci* 2007; 80:2243-2247) and the cornea (Norman et al., *Invest Ophthalmol Vis Sci* 2004; 45:429-440). In the skin, Slurp1 is abundantly expressed in the keratinocytes underlying the stratum corneum. Slurp1 is one of the most abundant transcripts in the neonatal and the adult mouse corneas (Norman et al., *Invest Ophthalmol Vis Sci* 2004; 45:429-440). Human SLURP1 mRNA expression is regulated by retinoic acid, epidermal growth factor and interferon-γ (Mastrangeli et al., *Eur J Dermatol* 2003; 13:560-570).

SLURP1 is a secreted protein, and is detected in many bodily fluids including the plasma, saliva, sweat, tears and urine, and is considered a late marker of epidermal differentiation (Favre et al., *J Invest Dermatol* 2007; 127:301-308). Slurp1 is thought to fine-tune the physiologic regulation of keratinocyte functions through the cholinergic pathways, as it is structurally similar to the snake and frog cytotoxin a-bungarotoxin, and acts as a ligand for the α7 subunit of the nicotinic acetylcholine receptors (a7nAchRs) (Mastrangeli et al., *Eur J Dermatol* 2003; 13:560-570, Arredondo et al., *J Invest Dermatol* 2005; 125:1236-1241). Slurp1 is involved in signal transduction, activation of the immune response, and cell adhesion, preventing tobacco nitrosamine-induced malignant transformation of oral cells. (Grando et al., *J Pharmacol Sci* 2008; 106:174-179, Moriwaki et al., *Life Sci* 2007; 80:2365-2368, Arredondo et al., *Life Sci* 2007; 80:2243-2247, Arredondo et al., *Biochem Pharmacol* 2007; 74:1315-1319, Chimienti et al., *Hum Mol Genet* 2003; 12:3017-3024). The secreted Ly6/uPAR-related protein-1 (SLURP1) is associated with the hyperkeratotic disorder Mal-de-Meleda.

The expression and function of Slurp1 in the corneas was evaluated and is disclosed herein. Gene expression was quantified by qPCR, immunoblots and immunofluorescent staining. Effect of Klf4 on Slurp1 promoter was evaluated by chromatin immunoprecipitation (ChIP) and transient transfections. Adenoviral vectors were used to express Slurp1 in corneas. Leukocytic infiltration in bacterial lipopolysaccharides (LPS), Herpes Simplex Virus Type-1 (HSV-1) or adenovirus (serotype-5) treated mouse corneas was characterized by flow cytometry.

As shown below, corneal expression of Slurp1 increased sharply upon mouse eyelid opening, concurrent with the elevated expression of Klf4. Slurp1 was significantly decreased in Klf4-conditional null (Klf4CN) corneas which displayed elevated expression of cytokines and cytokine receptors, and neutrophil influx consistent with a pro-inflammatory environment. In additional models of corneal inflammation, Slurp1 expression was abrogated within 24 hours (h) of bacterial LPS injection, HSV-1 or adenoviral infection, accompanied by a predominantly neutrophilic infiltrate. Neutrophilic infiltration was enhanced in HSV-1 infected Klf4CN corneas lacking Slurp1. Slurp1 promoter activity was stimulated by KLF4, suppressed by IL-4, IL-13 and TNFα, and unperturbed by interferon-γ (IFN-γ). Slurp1 downregulation and neutrophil influx were comparable in HSV-1 infected wild type (WT) and IFNγ−/− mouse corneas. Mouse corneas infected with Slurp1-expressing adenoviral vectors displayed reduced signs of inflammation and restricted neutrophilic infiltration compared with those infected with control vectors.

The results demonstrated that Klf4 regulates the expression of Slurp1, a key immunomodulatory peptide that is abundantly expressed in healthy corneas and is downregulated in pro-inflammatory conditions. Furthermore, SLURP1 can be used therapeutically as an immunomodulatory molecule to treat ocular inflammation, such as, but not limited to, keratitis.

Example 1

Materials and Methods

Mice.

Klf4CN mice were generated on a mixed background by mating Klf4$^{loxP/loxP}$, Le-Cre/− mice with Klf4$^{loxP/loxP}$ mice to obtain roughly equal proportion of Klf4$^{loxP/loxP}$, Le-Cre/− (Klf4CN) and Klf4$^{loxP/loxP}$ (WT control siblings) offspring as described earlier (Swamynathan et al., Mol Cell Biol 2007; 27:182-194). Wild type and IFN-γ knockout (GKO) BALB/c mice were purchased.

LPS Injection, HSV-1 or Adenoviral Infection of Mouse Corneas.

Mice were anesthetized by intraperitoneal injection of 2.0 mg of ketamine hydrochloride and 0.04 mg of xylazine (Phoenix Scientific, St. Joseph, Mo.) in 0.2 ml of Hanks balanced salt solution (Cambrex, Charles City, Iowa). The corneas of anesthetized mice were abraded 10 times in a crisscross fashion followed by topical application of 3 μl of RPMI 1640 (Cambrex, Charles City, Iowa) alone (mock infected) or RPMI 1640 containing $1 \times 10^5$ plaque forming units (PFU) of wild-type HSV-1 RE (HSV-1 infected) (Sheridan et. al., J Virol 2009; 83:2237-2245) Intrastromal injections of ultrapure bacterial LPS (Sigma-Aldrich Co., St. Louis, Mo.; 20 mg in 2 ml sterile water/cornea) were performed using fine tipped Hamilton syringes in tunnels generated by 32 gauge syringe needles.

Adenoviral vectors expressing Slurp1 were constructed in ADENOX® expression system (Serotype-5; Clontech Laboratories, Mountain View, Calif.) and amplified in HEK293 cells. $2 \times 10^6$ PFU of Adv5-Tet-Off alone (Control) or $10^6$ PFU each of Adv5-Tet-Off and Adv5-Slurp1 were used per abraded cornea, in mice anesthetized as above. Slit-lamp biomicroscope images were collected from anesthetized mice using SL-130 slit lamp (Carl Zeiss Meditec, Dublin, Calif.) equipped with a digital camera. Corneas were harvested at 4 days post-infection (DPI), and immersed in 1× phosphate buffered saline (PBS)-EDTA for 15 minutes at 37° C. to remove overlying epithelium, for isolating total RNA for quantitative polymerase chain reaction (QPCR). Stromal leukocytes were isolated, labeled and characterized by flow cytometry as described below.

Isolation of Total RNA and qPCR.

Corneas were excised from normal (non-infected) mice or at 6 hours (h), 12 h, 24 h, or 48 h after mock infection or HSV-1 corneal infection and soaked in RNA-Later to preserve the RNA integrity. Total RNA was isolated using the RNEASY® Mini kit (Qiagen, Valencia, Calif.). Unless otherwise mentioned, Applied Biosystems (Foster City, Calif.) was the source for the reagents, equipment and software for TAQMAN® gene expression quantitative real time PCR assays (qPCR). QPCR assays with pre-standardized gene-specific probes for different transcripts were performed in ABI STEPONE PLUS® thermal cycler using 18S rRNA or laminin-B1 as endogenous controls (to avoid skewing of the results due to the 18S rRNA from infiltrating immune cells in the inflamed corneas). Expression levels of different cytokines were quantified using the mouse cytokines PCR array following the protocol suggested by the manufacturer (SuperArray Biosystems, Frederick, Md.).

Effect of Cytokines on KLF4 and SLURP1 Expression.

cDNA was synthesized using 1 mg total RNA isolated from HCLE cells (Gipson et al., Invest Ophthalmol Vis Sci 2003; 44:2496-2506) treated with IL-2 (R and D Systems, Minneapolis, Minn.; 1 ng/ml), IL-4 (PeproTech, Rocky Hill, N.J.; 0.5 ng/ml), IL-13 (PeproTech, Rocky Hill, Rocky Hill, N.J.; 5 ng/ml), IFN-γ (Chemicon, Billerica, Mass.; 1 ng/ml), or TNFα (Fisher Scientific, Pittsburgh, Pa.; 0.2 ng/ml) for 2 days. QPCR was performed with KLF4- and SLURP1-specific probes and TAQMAN® reagents (Applied Biosystems, Carlsbad, Calif.) using 18S rRNA as endogenous control.

Immunoblots.

Equal amounts of total protein extracted by homogenizing dissected corneas in urea lysis buffer (8.0 M urea, 0.08% Triton X-100, 0.2% sodium dodecyl sulfate, 3% β-mercaptoethanol, and proteinase inhibitors) and quantified by the bicinchoninic acid method (Pierce, Rockford, Ill.) were electrophoresed in sodium dodecyl sulfate-polyacrylamide gels, transferred to polyvinylidene difluoride membranes and subjected to immunoblot analysis. Rabbit anti-mouse Slurp1 (Moriwaki Y, Watanabe Y, Shinagawa T, et al. Primary sensory neuronal expression of SLURP-1, an endogenous nicotinic acetylcholine receptor ligand. Neurosci Res 2009; 64:403-412 (Moriwaki et al., Neurosci Res 2009; 64:403-412) (1:1000 dilution) and goat anti-actin (Santa Cruz Biotechnology, Santa Cruz, Calif.) (1:1000 dilution) antibody were used as primary antibodies in PBS-Tris (PBST). Horseradish peroxidase-coupled goat anti-rabbit IgG (Invitrogen, Carlsbad, Calif.) (1:2000 dilution) or rabbit anti-goat IgG (Kirkegarad and Perry, Gaithersburg, Md.) (1:5000 dilution) was used as secondary antibody. Immunoreactive bands were detected by chemiluminescence using Super Signal West Pico solutions (Pierce, Rockford, Ill.).

Immunofluorescent Staining of Corneal Cryosections.

8-10 μm-thick cryosections from OCT-embedded mouse eyes or human central corneas were fixed in fresh 4% paraformaldehyde in PBS for 30 min, blocked for 1 h at room temperature with 10% goat serum in PBST, washed twice with PBST for 5 min each, incubated overnight at 4° C. with a 1:500 dilution of rabbit anti-mouse Slurp1 primary antibody (Moriwaki et al., Life Sci 2007; 80:2365-2368) (Moriwaki et al., Neurosci Res 2009; 64:403-412) or 1:50 dilution of goat anti-human SLURP1 antibody (Santa Cruz Biotechnology, Santa Cruz, Calif.), washed thrice with PBST for 10 min each, incubated with secondary antibody (AlexaFluor 546-coupled goat anti-rabbit IgG or Alexafluor 488-coupled donkey anti-goat IgG; Molecular Probes, Carlsbad, Calif.) at a 1:500 dilution for 1 h at room temperature, rinsed with PBS, incubated with DAPI for 10 minutes, washed thrice with PBST for 5 min each, mounted with Aqua Polymount (Polysciences, Inc), observed and images collected with Olympus IX81 microscope and Fluoview 1000 confocal system. All images presented within each composite figure were acquired under identical settings and processed in a similar manner using Adobe Photoshop and Illustrator (Adobe, Mountain View, Calif.).

Immunofluorescent Staining of Corneal Whole Mounts.

Corneas were dissected, flattened by three radial incisions, washed three times for 15 minutes each in PBS with 4% fetal bovine serum (FBS) and blocked in Fc block (BD Pharmingen, San Jose, Calif.) for 20 minutes prior to incubation with fluorescein isothiocyanate (FITC)-conjugated anti-CD45 antibody (BD Pharmingen, San Jose, Calif.) overnight at 4° C. Corneas were then washed three times each for 30 minutes in PBS/4% FBS, fixed in 1% Paraformaldehyde for 2 hours at 4° C., rinsed three times again for 30 minutes each in PBS/4% FBS and mounted in Aqua poly/Mount (Polysciences Inc, Warrington, Pa.). Images were acquired on an Olympus Fluoview 1000 confocal system with an Olympus IX81 microscope. Stacks were imaged at 20× (numerical aperture (NA) 0.85) and 60× (NA 1.42) and maximum intensity projections were imaged through the stromal portion of the stack.

Flow Cytometry.

Corneas were excised 48 h after mock or HSV-1 corneal infection, and immersed in 1×PBS-EDTA for 15 minutes at 37° C. to remove overlying epithelium. The corneal stroma was digested in collagenase type 1 (840 U/cornea, Sigma-Aldrich Co. St. Louis, Mo.) for 1 hour at 37° C. Single cell suspensions were generated by trituration and filtered through a 40-µm cell strainer cap (BD Labware, Bedford, Mass.). Suspensions were incubated with anti-mouse CD16/CD32 (Fcγ receptor; clone 2.4G2; BD Pharmingen, San Diego, Calif.), and then stained with fluorochrome-conjugated antibodies to various surface markers for 30 minutes at 4° C. The following antibodies and their corresponding isotypes were used for phenotypic analysis: PerCP-conjugated anti-CD45 (clone 30-F11; BD Pharmingen, San Diego, Calif.), APC-conjugated anti-Gr-1(clone RB6-8C5; Caltag Laboratories, Burlingame, Calif.), and eFluor450-conjugated anti-CD11b (clone M1/70; eBioscience, San Diego, Calif.). After staining, cells were fixed with 1% paraformaldehyde and mixed with COUNTBRIGHT® absolute counting beads (10,000 beads/sample; Invitrogen, Carlsbad, Calif.). Data were collected on a FACSARIA® cytometer and analyzed by FACSDIVA® Software (BD Biosciences, San Jose, Calif.). A gate was established to stop acquiring events after collecting 80% of the beads. The absolute number of each cell type per cornea was determined by calculating the number of events shown in the gate, multiplied by a factor of 1.25.

Chromatin Immunoprecipitation (ChIP).

ChIP was based on the EZ-CHIP® protocol (Upstate, Inc, Charlottesville, Va.). DNA-bound proteins were cross linked with 1% paraformaldehyde, the chromatin purified, sonicated and immunoprecipitated with pre-immune serum or anti-KLF4 antibody (Santa Cruz Biotechnology, Inc., Santa Cruz, Calif.) and protein G-sepharose. Following reversal of cross linking by heating overnight at 65° C. in the presence of NaCl and purification of eluted DNA, Slurp1 promoter fragments were detected by PCR with -396F (5' TTTATCAGGC AGGCAGATAT AAAGC 3', SEQ ID NO: 5) and +30R (5' ATTCTTCAGT GCTCAGGAGC T 3', SEQ ID NO: 6) primers.

Reporter Vectors, Cell Culture, and Promoter Activities.

Reporter vectors were generated in pGL3Basic (Promega, Madison, Wis.) by cloning the SLURP1 promoter fragments amplified using the following primers: -500F: 5'-ACA TCA GGT ACT CCC TCC T-3', -150F: 5'-GGC CCC ACC CTG GGA TGG TAG GTG A-3', and +30R: 5'-TCT TCA GTG CTC AGG AGC TAG GA-3'. Transient expression of Klf4 was achieved using CMV promoter in pCI-Klf4. Human keratinocyte NCTC cells and SV40-transformed corneal epithelial (HCE) cells (Araki-Sasaki et al., Invest Ophthalmol Vis Sci 1995; 36:614-621) were grown in six-well plates as described earlier (Swamynathan, et al., Invest Ophthalmol Vis Sci 2011; 52:1762-1769) and transfected with 0.5 µg reporter vector pSlurp1-Luc, 10 ng pRL-SV40 (Promega, Madison Wis., for normalization of transfection efficiency) and 0.5 µg pCI or pCI-Klf4, using 3 µl Fugene 6 (Roche Molecular Biochemicals, Indianapolis, Ind.). Transient knockdown of KLF4 expression in human corneal limbal epithelial (HCLE) (Gipson et al., Invest Ophthalmol Vis Sci 2003; 44:2496-2506) cells was achieved using plasmids expressing Anti-KLF4 siRNA described earlier (SuperArray Biosciences, Frederick, Md.) (Swamynathan et al., Invest Ophthalmol Vis Sci 2011; 52:1762-1769) HCLE cells in six-well plates were co-transfected with 1.0 µg control or anti-KLF4 siRNA plasmid, 0.5 µg reporter vector (-500/+27 bp Slurp1-Luc) and 15 ng pRL-SV40 (Promega, Madison Wis., for normalization of transfection efficiency) using 4.5 µl Lipofectamine 2000 (Invitrogen, Carlsbad, Calif.). After two days of transfection, cells were lysed with 500 µl of passive lysis buffer and 50 µg protein in the supernatant was analyzed using a dual-luciferase assay kit (Promega, Madison Wis.) and a Synergy-II microplate luminometer (Biotek Instruments, Winooski, Vt.) as earlier. (Swamynathan et al., Invest Ophthalmol Vis Sci 2011; 52:1762-1769) Results from three independent experiments, normalized for transfection efficiency using the SV40 promoter-driven Renilla luciferase activity, were used to obtain mean promoter activities and standard deviation. Fold-activation was determined by dividing mean promoter activity in the presence of pCI-Klf4 by the promoter activity in the absence of pCI-Klf4.

Example 2

Corneal Expression of Slurp1

Figure 1B:
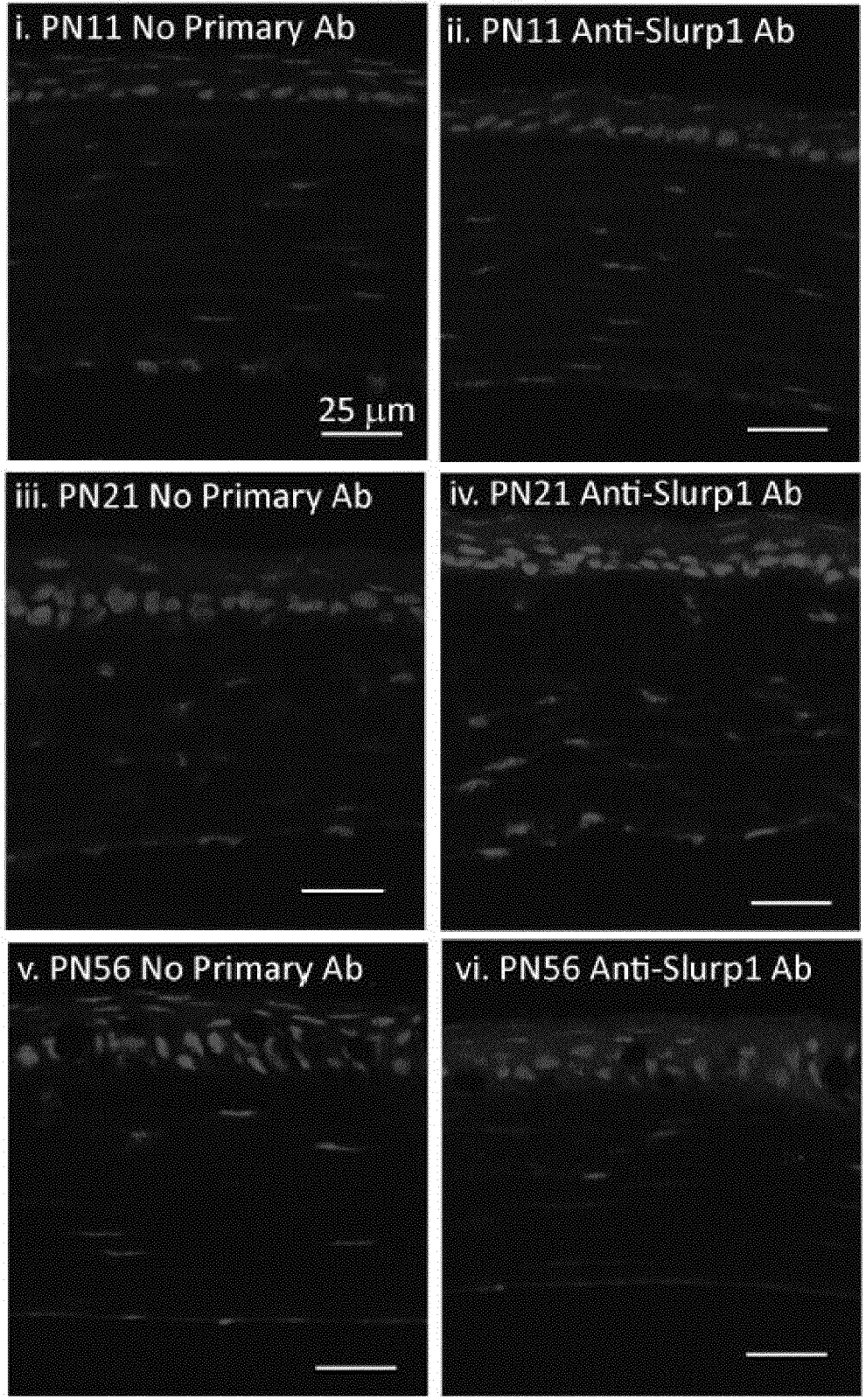
Figure 1C:
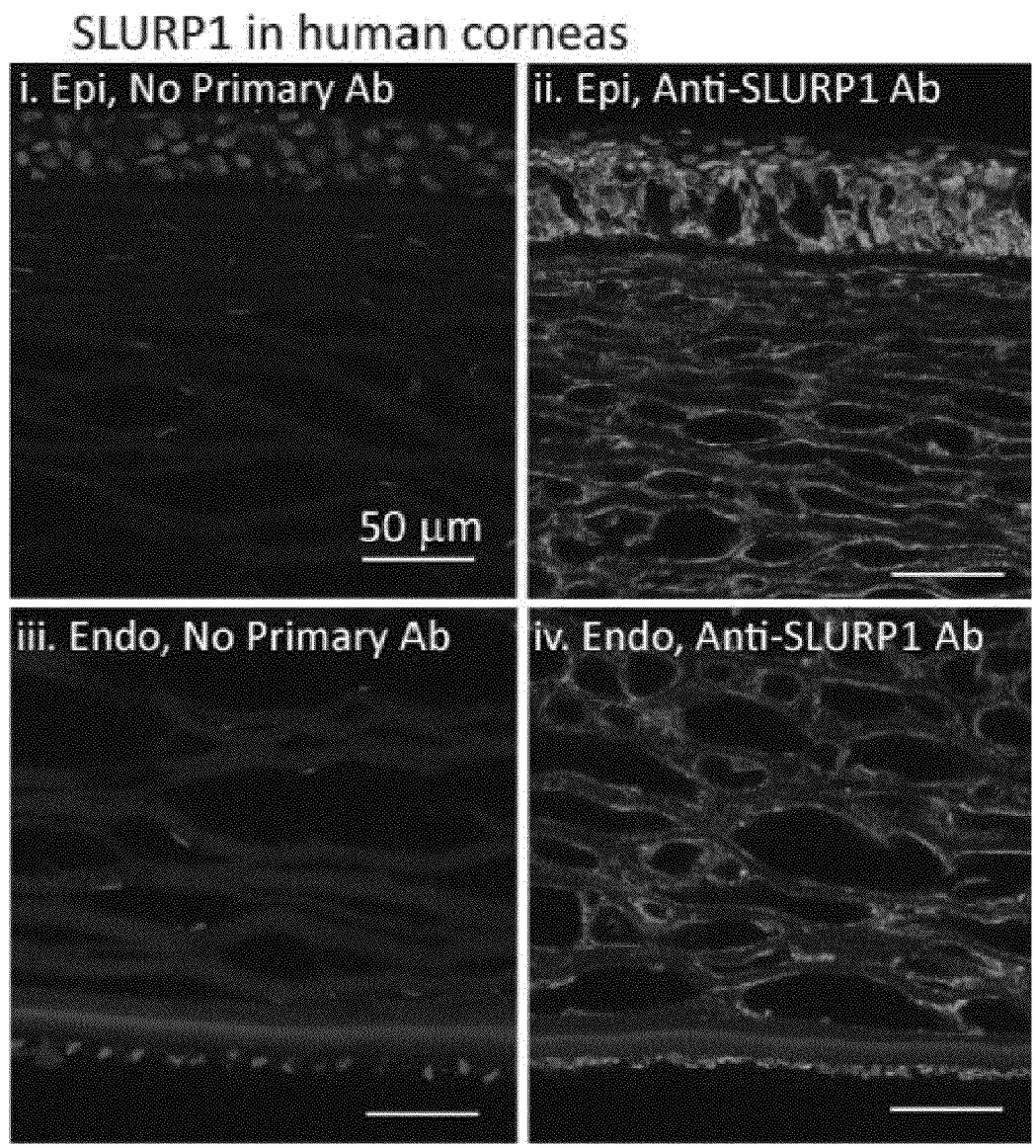

QPCRs revealed, and immunofluorescent staining confirmed that Slurp1 expression is increased by more than 15-fold between postnatal day 11 (PN11) and PN21 (FIGS. 1A and B), suggesting a critical role for Slurp1 in post-eyelid opening stages when the cornea is first exposed to the environment. Though Slurp1 was detected in all layers of the cornea, its expression was much higher in the epithelium (FIG. 1B), consistent with the previous in situ hybridization data (Norman et. al., Invest Ophthalmol Vis Sci 2004; 45:429-440). The spatial distribution of SLURP1 in human corneas was comparable to that in the mouse corneas, albeit with a little higher expression in the stroma, as demonstrated by immunofluorescent staining of human corneal sections from a healthy 52 year-old male organ donor (FIG. 1C). Together, these results reveal that Slurp1 is expressed at high levels in mature mouse and human corneas, with comparable tissue distribution (FIG. 1).

Example 3

Slurp1 and the Ocular Surface

The effect of Slurp1 on the functions of membrane-tethered uPAR, such as by acting as a soluble scavenger of its ligand urokinase-type plasminogen activator (uPA) was evaluated. It was also evaluated whether human SLURP1 expression is dependent on ocular surfaces health.

For these studies, recombinant 6× His-Slurp1 and MBP-uPA were expressed in E. coli and partially purified using nickel-ion and amylose columns, respectively. The interaction of Slurp1 with uPA was detected using ligand blots, enzyme-linked immunosorbent assays (ELISA), pull-down assays and immunofluorescent staining. Mouse corneal stromal fibroblast M/KT-1 cells were employed to examine the effect of Slurp1 on cell proliferation, migration, and attachment to extracellular matrix (ECM). Expression of Slurp1 in human tears from healthy or inflamed ocular surface was assessed by immunoblots.

The ligand blots, ELISA, and pull-down assays indicated that Slurp1 efficiently interacts with uPA. Immunofluorescent staining demonstrated that exogenous Slurp1 decreased the amount of cell surface-bound uPA present in discrete foci in stagnant cells, and in the leading edge of migrating cells. M/KT-1 cell proliferation, ECM attachment, and migration rate were suppressed by Slurp1. SLURP1 was abundant in tears from healthy human ocular surface and was either decreased or absent in tears from inflamed ocular surface.

Without being bound by theory, Slurp1 can modulate corneal inflammation by serving as a soluble scavenger of uPA, and regulating the ocular surface functions of uPAR. Furthermore, the results confirmed that SLURP1 is active in humans.

Example 4

Klf4 Binds and Upregulates Slurp1 Promoter Activity

Figure 2A:
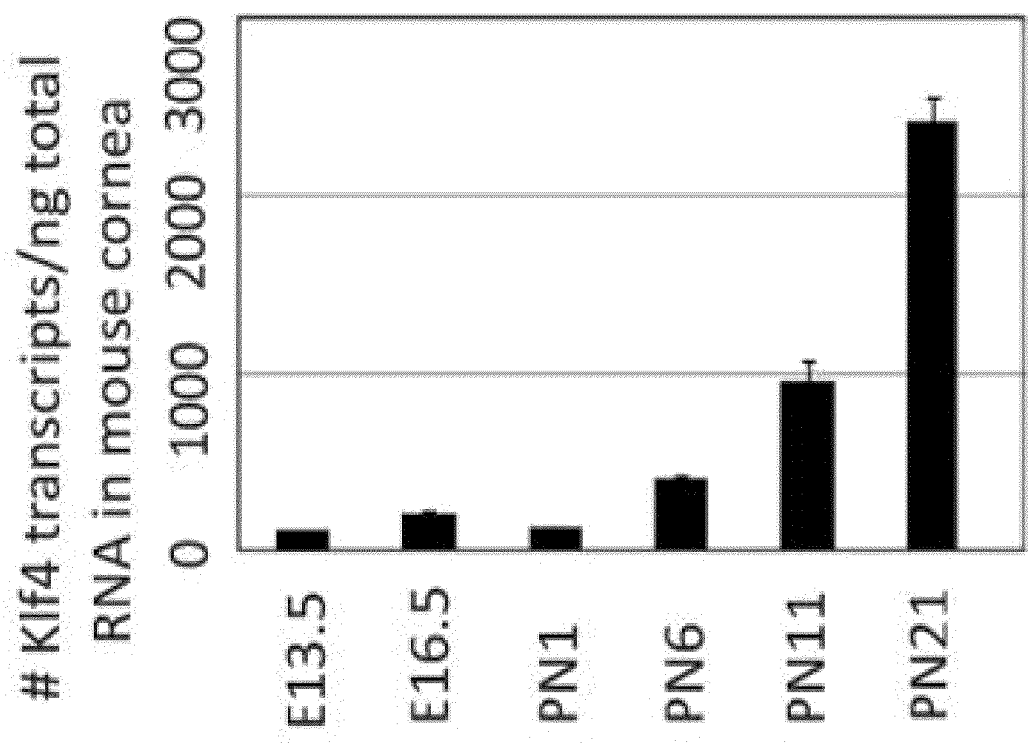
FIGS. 2A-2D. Downregulation of Slurp1 expression in the Klf4CN cornea. A, Changes in Klf4 expression during mouse corneal development. Absolute numbers of Klf4 transcripts per ng total RNA were calculated using the standard curve method of QPCR with total RNA from mouse corneas at different stages of development. B, Slurp1 transcript levels in the WT and Klf4CN corneas measured by microarray (Swamynathan et al., *Invest Ophthalmol Vis Sci* 2008; 49:3360-3370) and QPCR. C, Immunoblot with rabbit anti-mouse Slurp1 antibody detects a strongly reacting band at about 21 kDa in the WT, but not in Klf4CN corneal extracts (left panel). The blot was stripped of the primary antibody and re-probed with anti-actin antibody, to ensure equal loading of protein (right panel). D, Immunofluorescent staining with anti-Slurp1 antibody. Left panel, WT with no primary antibody; middle panel, WT with anti-Slurp1 antibody; Right panel, Klf4CN with anti-Slurp1 antibody.
Figure 2B:
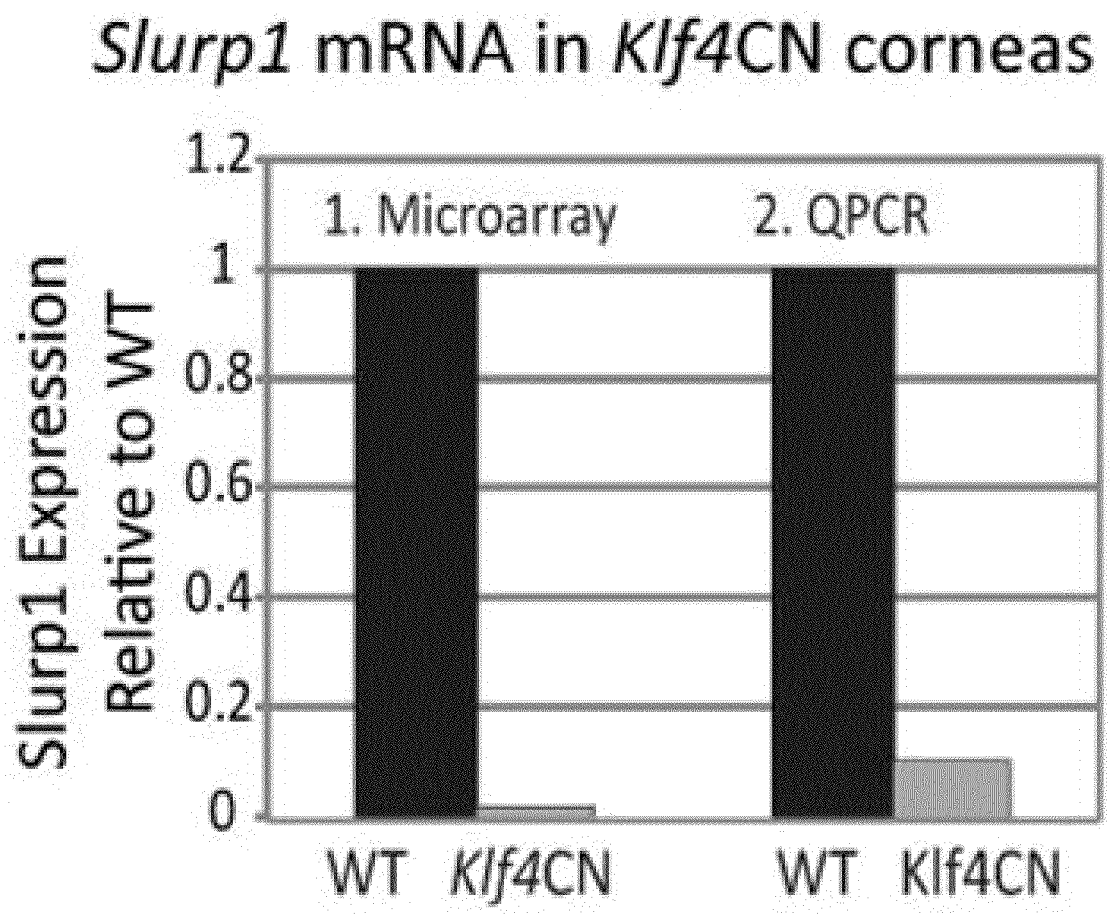
Figure 2C:
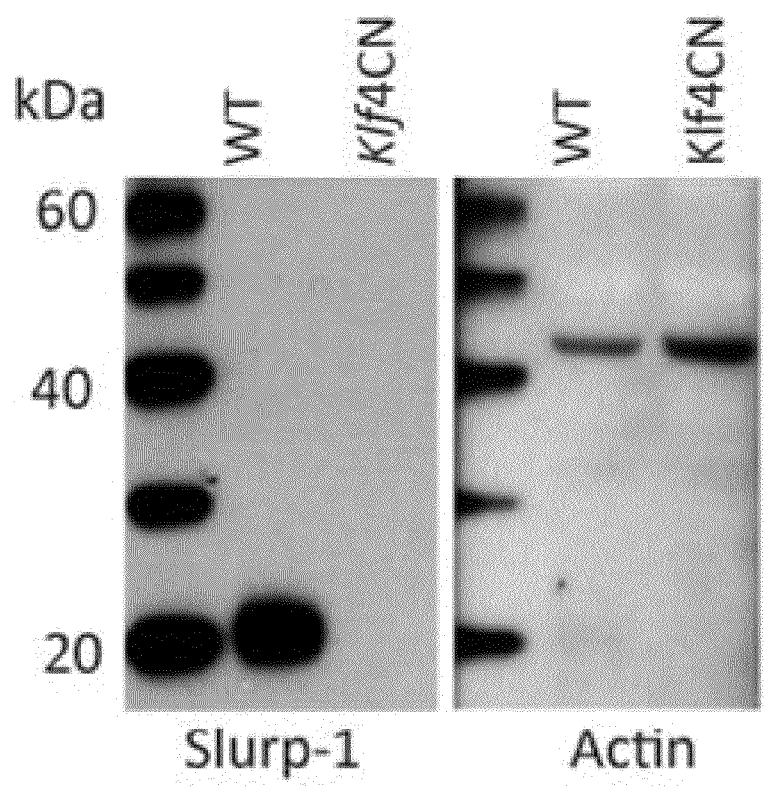
Figure 2D:
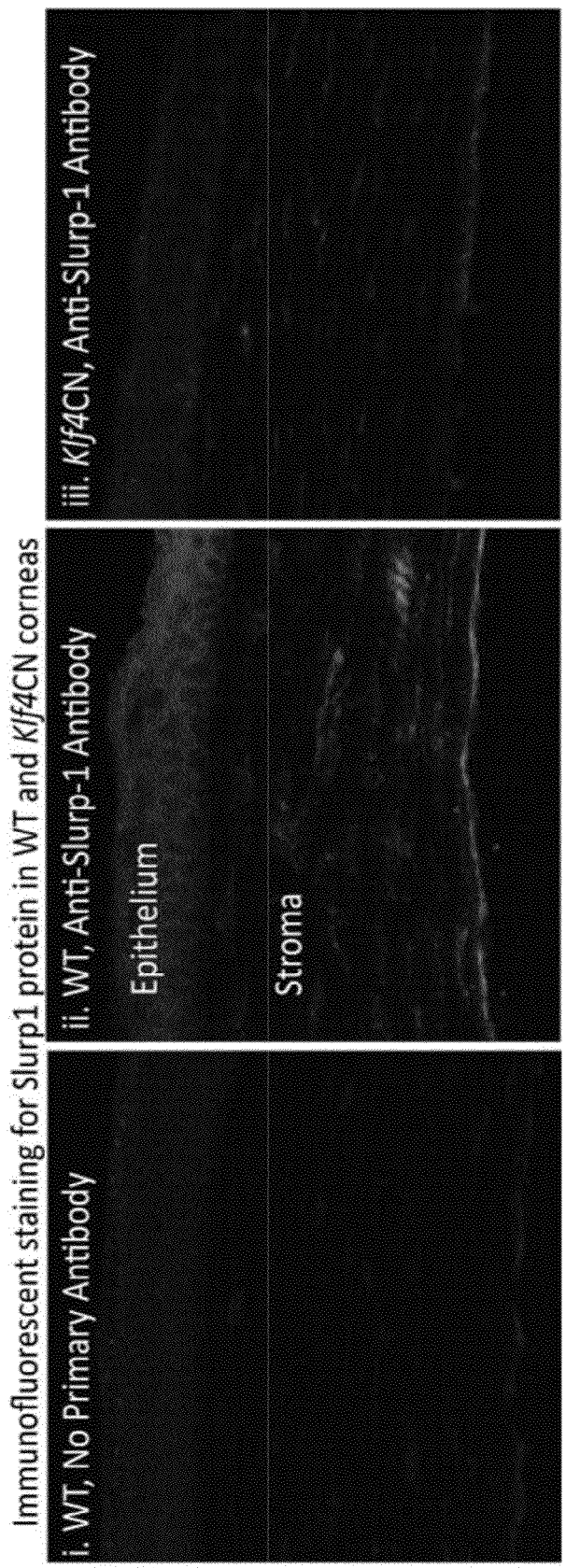

The increase in Slurp1 expression during post-eyelid opening stages is concurrent with an increase in the expression of Klf4 (FIG. 2A) which plays critical roles in maturation and maintenance of the mouse ocular surface (Swamynathan et al., Invest Ophthalmol Vis Sci 2011; 52:1762-1769, Swamynathan et al., Invest Ophthalmol Vis Sci 2008; 49:3360-3370, Swamynathan et al., Mol Cell Biol 2007; 27:182-194) raising the possibility that Klf4 regulates Slurp1 expression. Microarray data (Swamynathan et al., Invest Ophthalmol Vis Sci 2008; 49:3360-3370), and the present quantitative polymerase chain reaction (QPCR), immunoblots and immunofluorescent staining confirmed a significant decrease in Slurp1 expression in Klf4CN compared with the WT corneas (FIGS. 2B, C, and D). These results suggest that Klf4 regulates the sharp increase in post-eyelid opening expression of Slurp1.

Figure 3A:
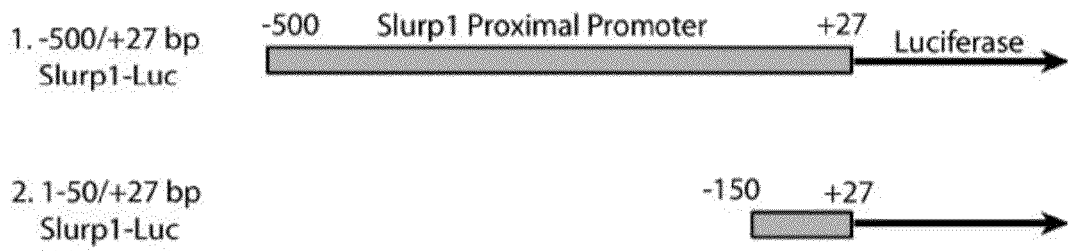
Figure 3B:
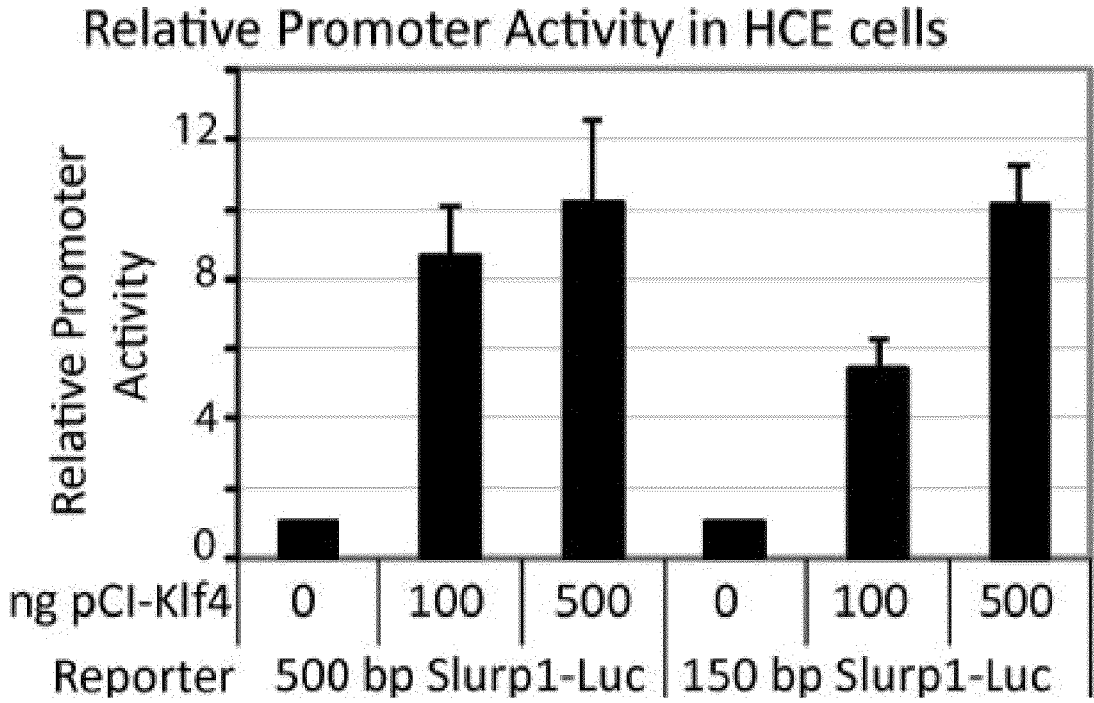
Figure 3C:
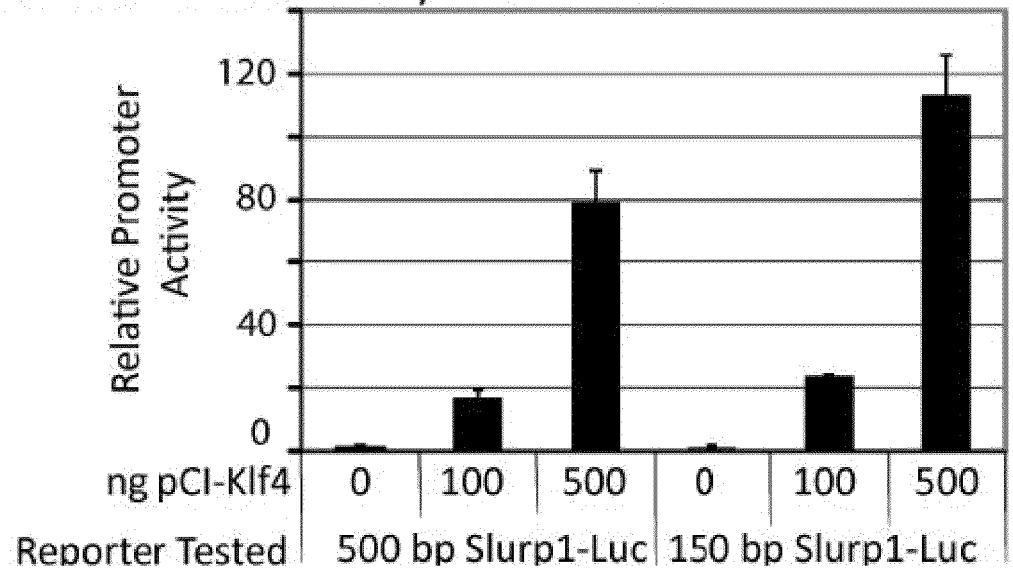
Figure 3D:
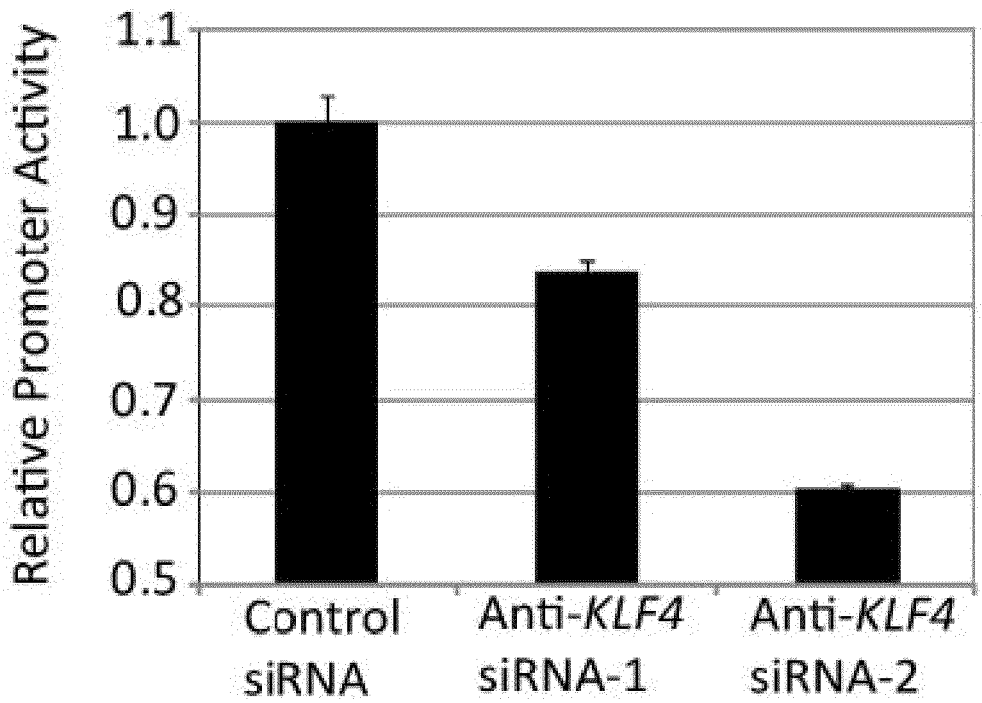
Figure 4A:
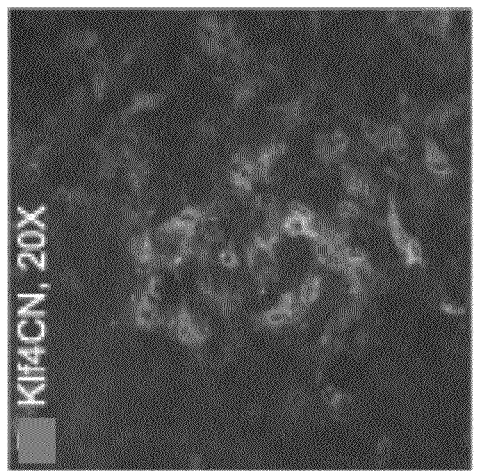
FIGS. 4A-4D. Localization of CD45$^+$ cells in the WT and Klf4CN corneas. Flat mounts of WT (panels A and C) and Klf4CN (panels B and D) corneas were stained with fluorescein isothiocyanate (FITC)-conjugated anti-CD45 antibody and examined by confocal microscopy. Representative stacked images of the central region of corneas are shown at 20× (panels A and B; numerical aperture (NA) 0.85) and 60× (panels C and D; NA 1.42) magnification. Note the relatively even distribution and lower density of CD45$^+$ cells in the WT corneas compared with their higher density and clustering in Klf4CN corneas.
Figure 4B:
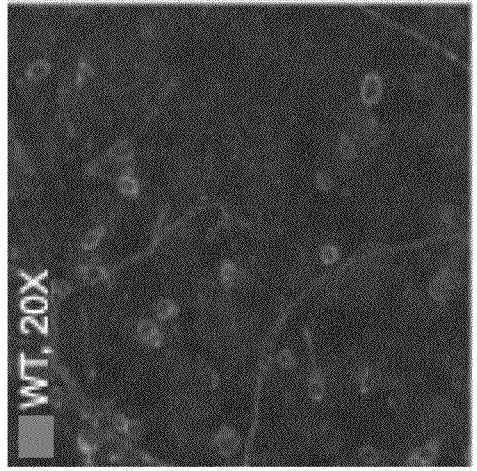
Figure 4C:
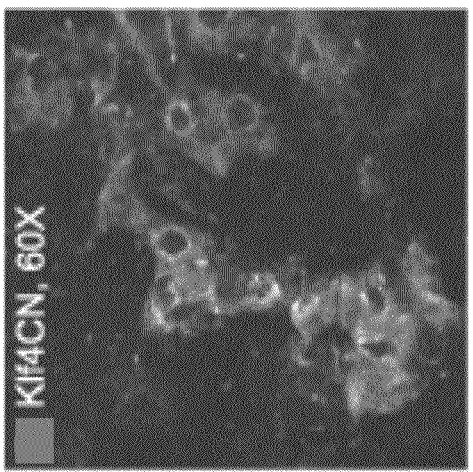
Figure 4D:
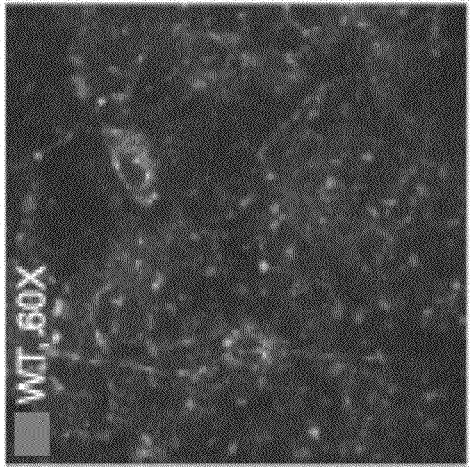

In order to directly test if Klf4 regulates Slurp1 promoter activity, the luciferase reporter vectors driven by mouse Slurp1 promoter (−500/+27 base pair (bp) or −150/+27 bp fragments; FIG. 3A) was co-transfected with increasing amounts of the empty control vector pCI or the expression vector pCI-Klf4, in human corneal epithelial (HCE) or skin keratinocyte (NCTC) cells. Activities of both −500/+27 bp and −150/+27 bp Slurp1 promoter fragments were increased upon co-transfection with pCI-Klf4 (FIGS. 3B and C), suggesting that the Klf4-responsive elements are located within the −150/+27 bp Slurp1 proximal promoter. In addition, specific siRNA-mediated knockdown of KLF4 resulted in reduced −500/+27 bp Slurp1 promoter activity, relative to that obtained with co-transfection of control siRNA-expressing plasmids in HCLE cells (FIG. 3D). Chromatin immunoprecipitation (ChIP) assays demonstrated that the −396/+30 bp Slurp1 promoter fragment is bound by KLF4 in HCE cells (FIG. 3E). Finally, examination of the Slurp1 promoter sequence revealed the presence of several potential KLF4-binding sites (GC-rich regions with a core sequence $CACCC^{41}$) within the −500/+27 bp fragment, many clustered within the −150/+27 bp region (FIG. 3F), consistent with the stimulation of the −150/+27 bp proximal promoter activity by Klf4. Taken together, these results demonstrate that Klf4 binds and upregulates Slurp1 proximal promoter activity.

Example 5

Inflammatory Environment in Klf4CN Corneas

Deletions or mutations in SLURP1 cause autosomal recessive inflammatory disorder Mal-de-Meleda (Mastrangeli et al., Eur J Dermatol 2003; 13:560-570, Favre et al., J Invest Dermatol 2007; 127:301-308, Arredondo et al., Biochem Pharmacol 2007; 74:1315-1319, Chimienti et al., Hum Mol Genet 2003; 12:3017-3024, Fischer et al., Hum Mol Genet 2001; 10:875-880, Eckl et al., Hum Genet 2003; 112:50-56, Hu et al., J Invest Dermatol 2003; 120:967-969, Marrakchi et al., J Invest Dermatol 2003; 120:351-355, Ward et al., J Invest Dermatol 2003; 120:96-98). Slurp1 expression is decreased in diverse pro-inflammatory conditions including suture- or alkali burn-induced corneal neovascularization (Jia et al., Mol Vis 2011; 17:2386-2399) (NCBI GEO accession number GSE23347), asthmatic lungs (Narumoto et al., Biochem Biophys Res Commun 2010; 398:713-718), Barrett's esophagus, adenocarcinomas, malignant melanomas, cervical cancer, and oral squamous cell carcinomas, (NCBI GEO Accession Numbers GDS1321, GDS3472, GDS1375 and GDS1584). It was tested if down regulation of Slurp1 is accompanied by pro-inflammatory conditions in Klf4CN corneas. QPCR revealed that the expression of interferon-γ, 19 different chemokines, 8 chemokine receptors, 5 interleukins, and 5 interleukin receptors is up-regulated by more than 4-fold in the Klf4CN compared with the WT corneas (Table 1), indicating a pro-inflammatory environment in Klf4CN corneas.

Table 1

Real Time Q-RT-PCR Estimation of the Expression Levels of Cytokines, Chemokine Ligands and Chemokine Receptors in the Klf4CN Cornea A. Cytokines/Chemokine Ligands

| Gene | Relative Expression in Klf4CN cornea | Target Cells (Chemoattractant for) |
| --- | --- | --- |
| Il13 | 19.126 | |
| Il4 | 6.904 | |
| Il1f6 | 5.380 | |
| Il3 | 5.054 | |
| Il10 | 5.342 | |
| Ifng | 5.089 | |
| Cxcl5 | 12.707 | Neutrophils |
| Cxcl11 | 9.563 | Activated T cells |
| Cxcl15 | 8.923 | Neutrophils |
| Ccl12 | 8.268 | Peripheral blood monocytes |
| Ccl19 | 7.931 | Dendritic cells |
| Ccl11 | 7.822 | Eosinophils |
| Cxcl10 | 7.555 | Macrophages, T cells, NK cells, and dendritic cells |

-continued

| Gene | Relative Expression in Klf4CN cornea | Target Cells (Chemoattractant for) |
|---|---|---|
| Ccl1 | 6.904 | Monocytes, NK cells, immature B cells and dendritic cells |
| Ccl6 | 6.353 | Macrophages, B cells, CD4 T cells, eosinophils |
| Cxcl9 | 6.309 | Activated T cells and NK cells |
| Ccl8 | 5.969 | Mast cells, eosinophils, basophils, monocytes, T cells, and NK cells |
| Ccl20 | 5.726 | Dendritic cells |
| Ccl5 | 5.531 | T cells, eosinophils, and basophils |
| Cxcl13 | 5.269 | B cells |
| Ccl17 | 5.232 | Activated T cells |
| Ccl22 | 4.985 | Dendritic cells, NK cells, and Th2 cells |
| Ccl7 | 4.882 | Monocytes |
| Cxcl12 | 4.749 | Lymphocytes |
| Pf4 | 4.250 | Neutrophils and monocytes |

B. Chemokine Receptors

| Gene | Relative Expression in Klf4CN cornea |
|---|---|
| Ccr7 | 15.322 |
| Il1r2 | 14.395 |
| Ccr4 | 8.325 |
| Il5ra | 8.325 |
| Ccr1 | 7.001 |
| Ccr6 | 6.487 |
| Ccr2 | 5.726 |
| Il10ra | 5.342 |
| Ccr3 | 5.342 |
| Cxcr5 | 5.306 |
| Xcr1 | 5.160 |
| Il8rb | 4.221 |
| Il2rg | 4.192 |
| Cd40lg | 12.884 |
| Itgb2 | 11.856 |

Furthermore, Klf4CN corneas displayed a significantly higher density of bone marrow-derived $CD45^+$ cells in comparison with the WT corneas (FIG. 4). While $CD45^+$ cells were sparsely and evenly distributed throughout the WT corneal stromas, they were present in large numbers in discrete clusters in the Klf4CN corneas (FIG. 4). Thus, Klf4CN corneas lacking Slurp1 exhibit a marked pro-inflammatory environment.

Example 6

Slurp1 Expression is Reduced in Inflamed Corneas

Figure 5A:
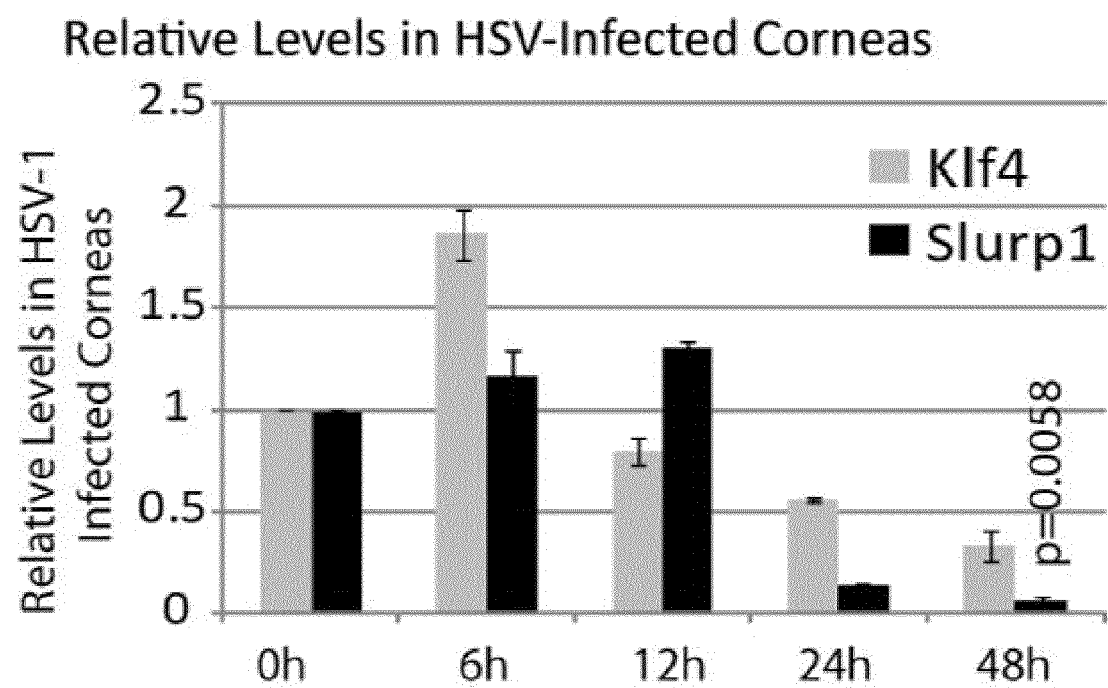
FIGS. 5A-5C. Expression of Klf4 and Slurp1 in herpes simplex virus serotype-1 (HSV-1) infected (A and B), and (C) bacterial lipopolysaccharide (LPS)-injected corneas. Control (mock infected or PBS-injected), HSV-1 infected (A), or LPS-injected (C) WT mouse corneas were harvested at the indicated time after treatment. Klf4 and Slurp1 transcripts were quantified by QPCR. Bars indicate relative expression levels (mean±SEM) of Klf4 and Slurp1 in HSV-1 infected (A), or LPS-injected (C) corneas. B. Immunofluorescent staining with anti-Slurp1 antibody in mock- or HSV-1-infected mouse corneas at 1 and 2 days post-scratching (DPS, Control) or post-infection (DPI). Nuclei are stained with DAPI (blue) and corresponding 'no antibody controls' are shown. Note that Slurp1 is abundantly expressed in control (panels iii and iv), and sharply decreased in HSV-1 infected corneal epithelia (panels v and vi) at both 1 and 2 DPI. Scale bars: 25 mm.
Figure 5B:
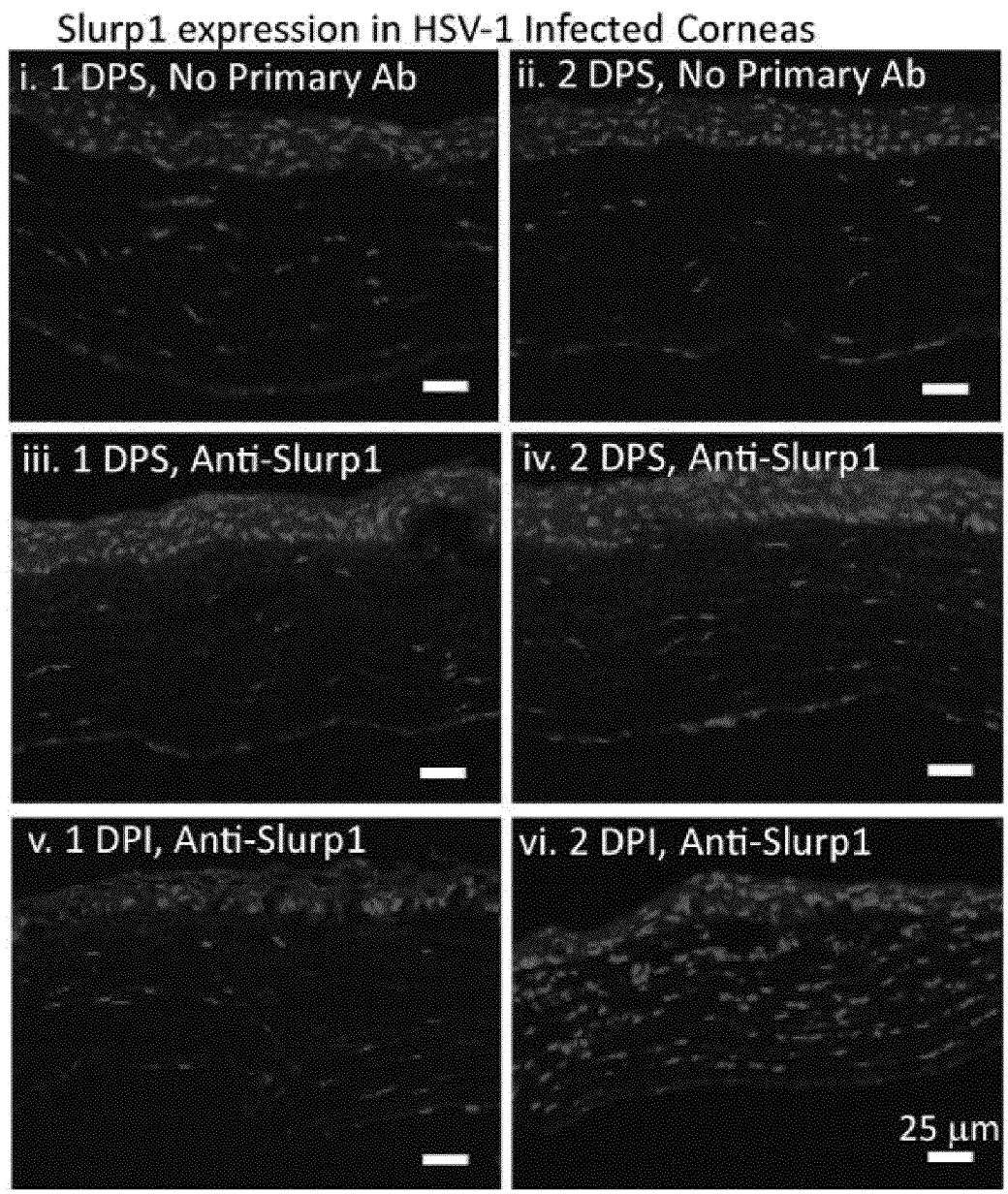
Figure 5C:
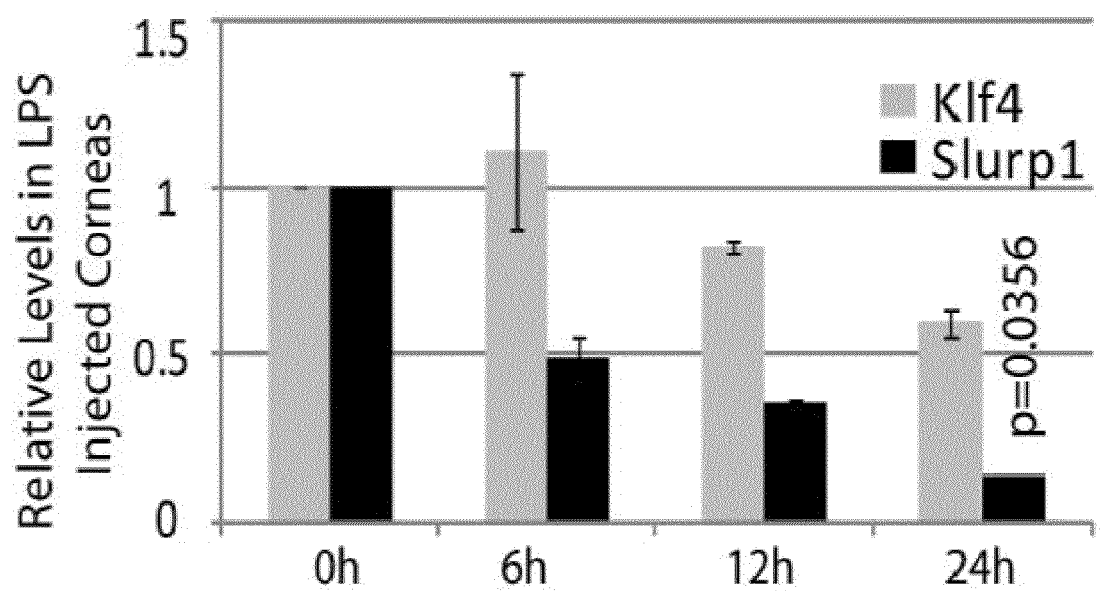

In order to determine if reduced expression of Slurp1 is a common theme in inflamed corneas, additional models of corneal inflammation including Herpes Simplex Virus Type-1 (HSV-1) infection and bacterial lipopolysaccharide (LPS) injection were examined. Slurp1 was sharply decreased one day after HSV-1 infection or LPS-injection, while Klf4 was not affected (FIG. 5). Klf4 was only partially reduced after two days in HSV-1 infected corneas, suggesting that the rapid reduction in Slurp1 levels within 24 h of LPS or HSV-1 treatment is not due to inadequate Klf4 levels (FIG. 5) Immunofluorescent staining confirmed the decreased expression of Slurp1 in HSV-1 infected mouse corneas at both 1 and 2 DPI (FIG. 5B). Along with a decrease in Slurp1 expression, a greater influx of cells stained with DAPI was also observed after HSV-1 infection. Taken together, these results demonstrate that the decreased expression of Slurp1 is a common theme in inflammation independent of the nature of insults, and suggest an immunomodulatory role for Slurp1.

Example 7

Figure 6A:
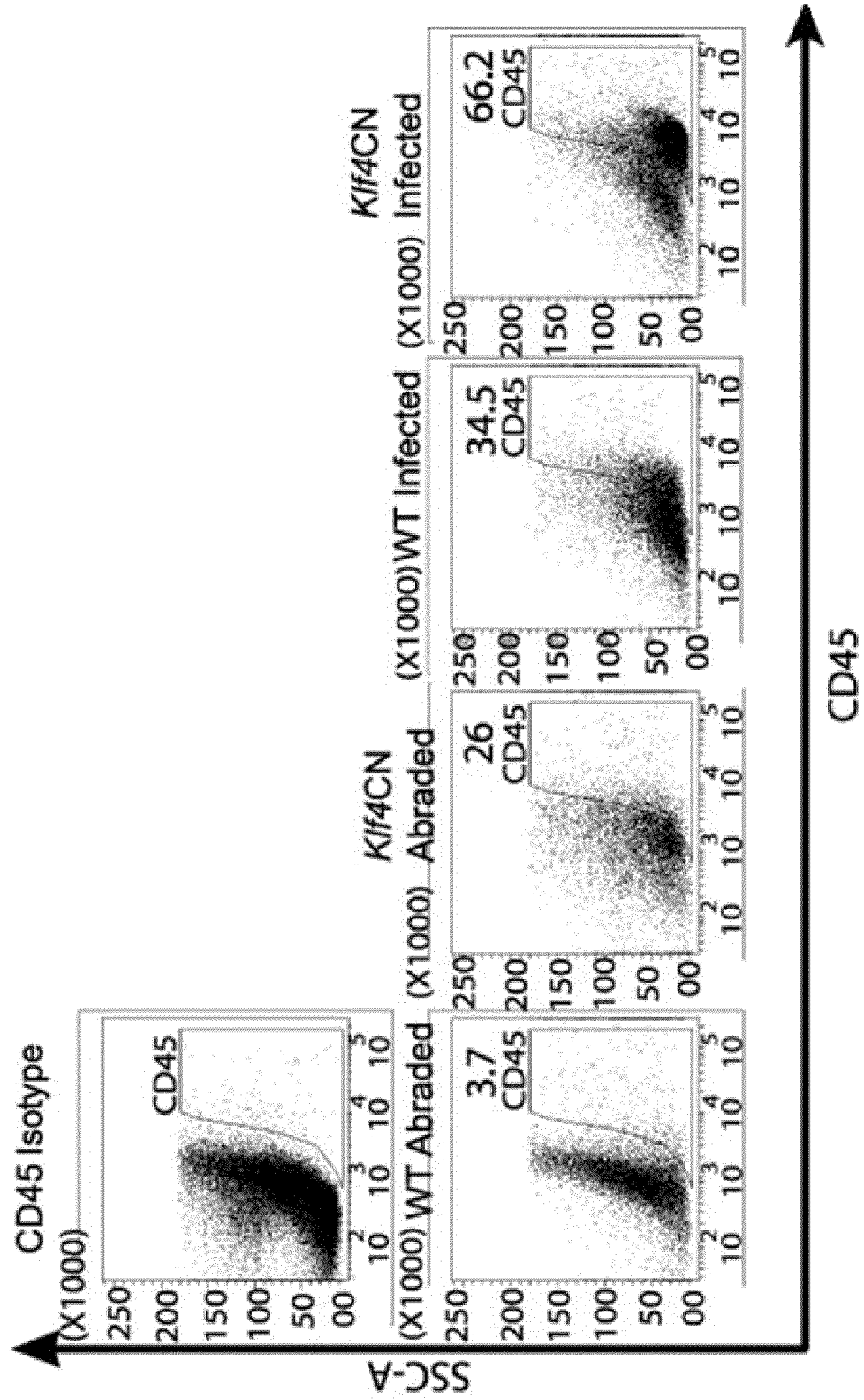
FIGS. 6A-6D. Leukocyte populations in mock- and HSV-1-infected corneas. Mock- or HSV-1-infected corneas from WT and Klf4CN littermates were excised 2 DPI, the cells dispersed with collagenase, stained with fluorochrome-conjugated antibodies specific for CD45, CD11b, and Gr-1, and analyzed by flow cytometry. (A) Representative dot plots illustrate gating on CD45$^+$ cells. Percentage of CD45$^+$ cells among stromal cells is shown within each dot plot. (B) The scatter plot shows the frequency of CD45$^+$ cells in mock infected and HSV-1 infected corneas. (C) Representative dot plots illustrate gating on CD11b$^+$ Gr-1$^+$ cells within a population gated on CD45$^+$ cells. Percentage of Gr-1$^+$ CD11b$^+$ cells among stromal CD45$^+$ cells is shown within the upper right quadrant of each dot plot. (D) The scatter plot shows the frequency of CD11b$^+$ Gr-1$^+$ cells among CD45$^+$ cells in mock infected and HSV-1 infected corneas.
Figure 6B:
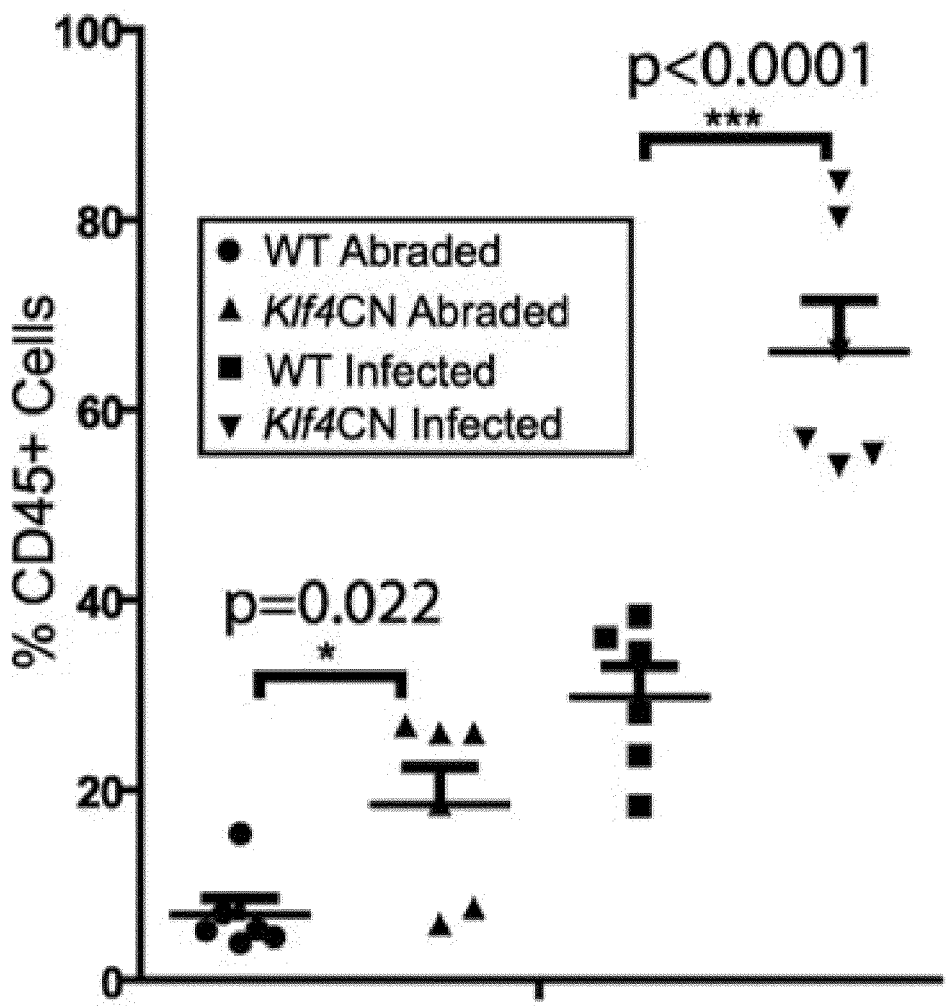
Figure 6C:
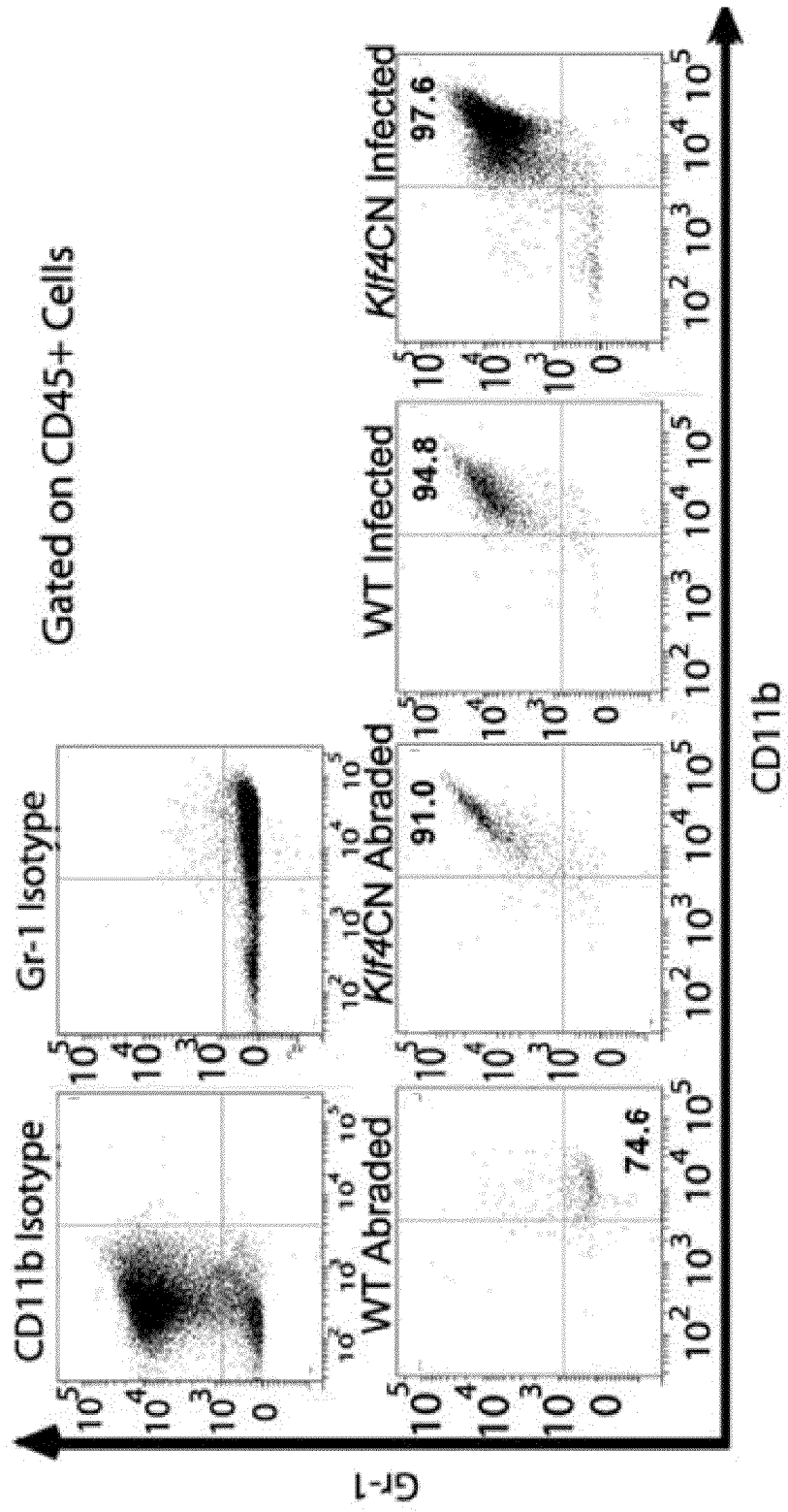
Figure 6D:
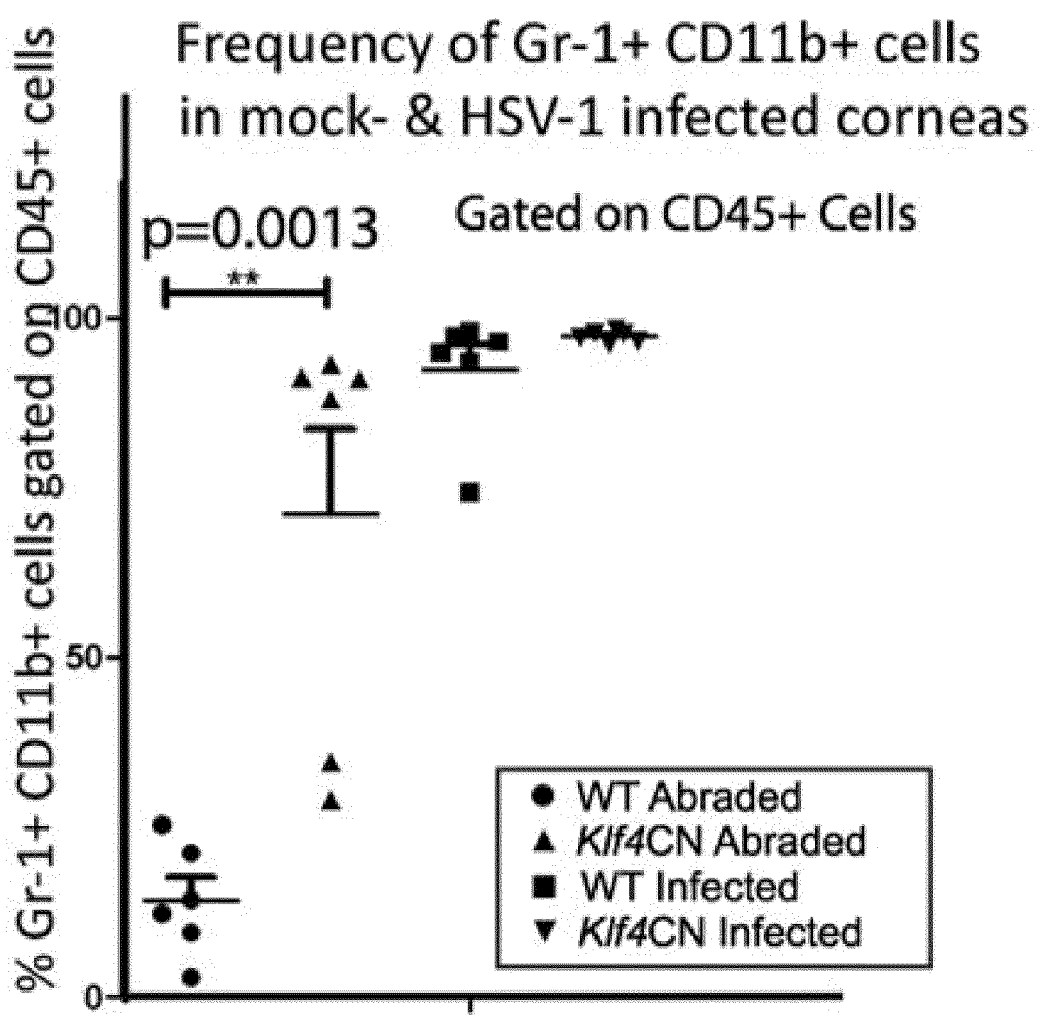

Reduced Expression of Slurp1 is Associated with Increased Neutrophilic Infiltration Flow cytometric analysis 2 days after mock infection revealed significantly (p=0.02) higher frequency of $CD45^+$ cells in the Klf4CN compared with the WT corneas (FIGS. 6A and B). The Klf4CN corneal $CD45^+$ cells were predominantly neutrophilic in nature ($CD11b^+$ $Gr-1^+$) compared with the predominantly macrophage phenotype ($CD11b^+$ $Gr-1^-$) of wild type (WT) corneal $CD45^+$ cells (FIGS. 6C and D). At 2 DPI, both WT and Klf4CN corneas exhibited elevated infiltration of bone marrow-derived $CD45^+$ cells comprised predominantly of $CD11b^+$ $Gr-1^+$ neutrophils, the frequency of which was significantly higher (p<0.0001) in the Klf4CN corneas (FIG. 6). Although it did not reach statistical significance, there was a trend towards higher absolute numbers of neutrophils in the infected Klf4CN corneas (Table 2A).

TABLE 2

Enumeration of CD45+, and Gr-1+ CD11b+ cells

| Treatment | CD45+ Cells ± SEM | Gr-1+ CD11b+ Cells ± SEM |
|---|---|---|
| (A) Abraded and HSV-1-infected WT and Klf4CN corneas | | |
| WT Abraded | 210 ± 65 | 41 ± 14 |
| WT Infected | 1350 ± 361 | 1310 ± 356 |
| Klf4CN Abraded | 455 ± 160 (p = 0.1938) | 403 ± 157 (p = 0.0507) |
| Klf4CN Infected | 8687 ± 3793 (p = 0.0903) | 8529 ± 3733 (p = 0.0904) |
| (B) Abraded and HSV-1-infected WT and GKO corneas | | |
| WT Abraded | 1997 ± 394 | 445 ± 129 |
| WT Infected | 12283 ± 1677 | 9729 ± 2730 |
| GKO Abraded | 1994 ± 355 (p = 0.9956) | 686 ± 201 (p = 0.3425) |
| GKO Infected | 13125 ± 2443 (p = 0.7835) | 11096 ± 2319 (p = 0.7127) |

CD45+, and Gr-1+ CD11b+ cells were enumerated in abraded and HSV-1-infected (A) WT and Klf4CN corneas (mixed background), and (B) WT and GKO corneas (BALB/c). Average number of cells derived from three independent replicates is provided with standard error of mean (SEM). The p values provide a measure of statistical significance in comparison with the corresponding WT samples. The differences in CD45+ and Gr-1+ CD11b+ cell numbers in the WT abraded and infected corneas between the two experiments may be due to the different strains used, and/or different size of the cornea analyzed, to account for the smaller Klf4CN corneas.

Thus, HSV-1 infection overcomes the barrier to neutrophilic infiltration into WT corneas, but does so more effectively in Klf4CN corneas lacking Slurp1 from the time of infection, consistent with the immunomodulatory role of Slurp1.

Example 8

SLURP1 Expression is Inhibited by Pro-Inflammatory Cytokines IL-4, IL-13 and TNF-α, but not Interferon-γ

Figure 7A:
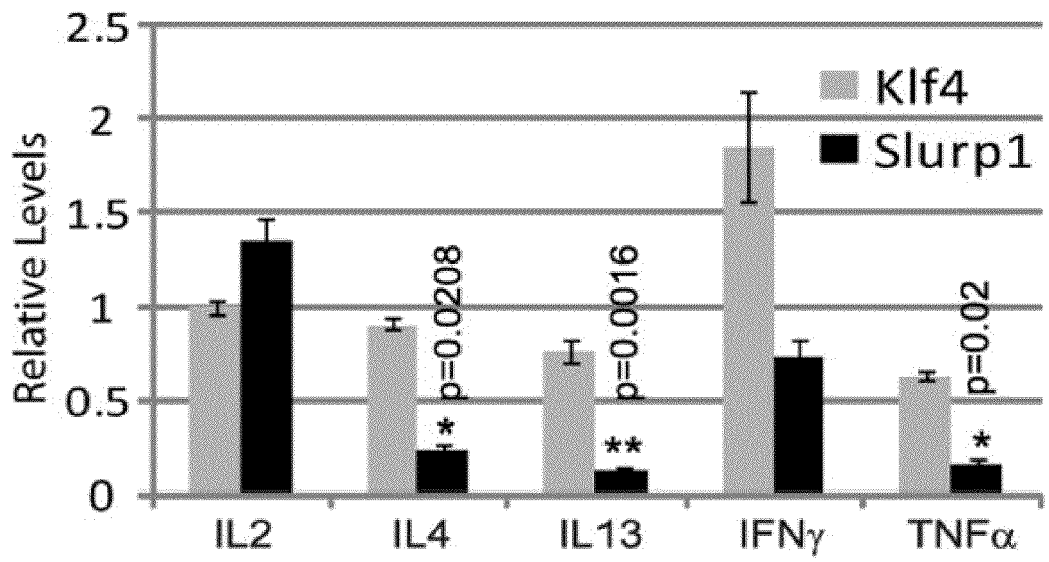
FIGS. 7A-7D. Interferon-gamma (IFN-γ) is not required for Slurp1 down-regulation and neutrophilic infiltration into infected corneas. (A) Slurp1 and Klf4 transcripts in HCLE cells exposed to different cytokines. QPCR was performed with total RNA from HCLE cells exposed to different cytokines indicated for two days, with 18s rRNA as endogenous control. Mean data from 3 independent experiments is presented. Error bars represent standard error of mean (SEM). The p values were calculated using Student's t-test. (B) Slurp1 and Klf4 transcripts in mock- or HSV-1 infected BALB/c WT or GKO corneas at 2 DPI. Bars indicate the mean±SEM fold change in Slurp1 expression in mock- or HSV-1 infected corneas over that in control corneas. The p values were calculated using Student's t-test. (C & D) The cells in mock- or HSV-1 infected WT or GKO corneas were dispersed with collagenase, stained with fluorochrome-conjugated antibodies specific for CD45, CD11b, and Gr-1, and analyzed by flow cytometry. (C) The scatter plot shows the frequency of CD45$^+$ cells in mock infected and HSV-1 infected corneas. (D) The scatter plot shows the frequency of CD11b$^+$ and Gr-1$^+$ double positive cells among CD45$^+$ cells in mock infected and HSV-1 infected corneas. Cumulative data from five different abraded mock- or HSV-infected WT and GKO animals each is shown.
Figure 7B:
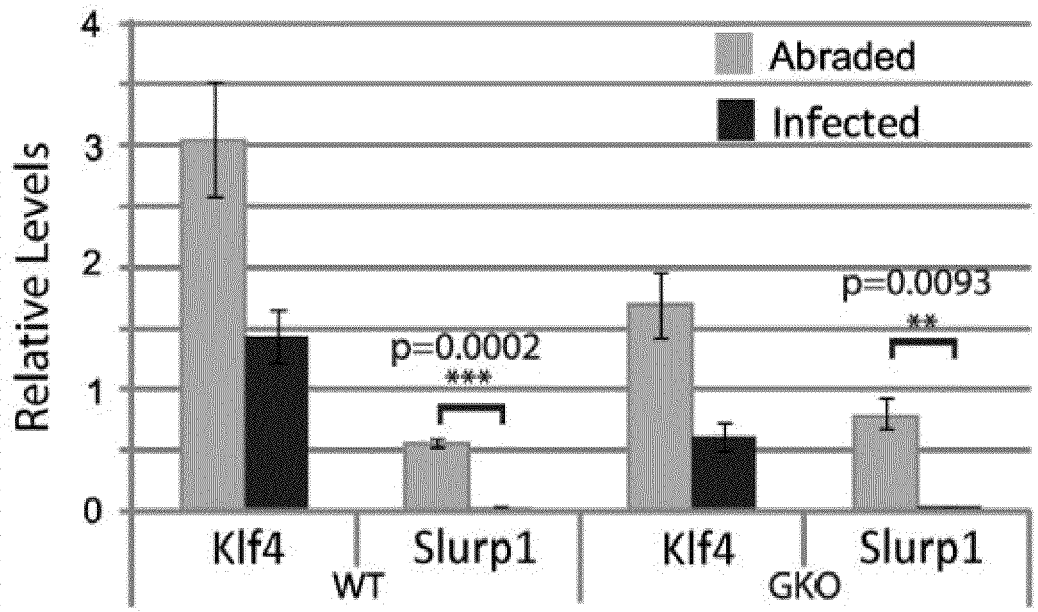
Figure 7C:
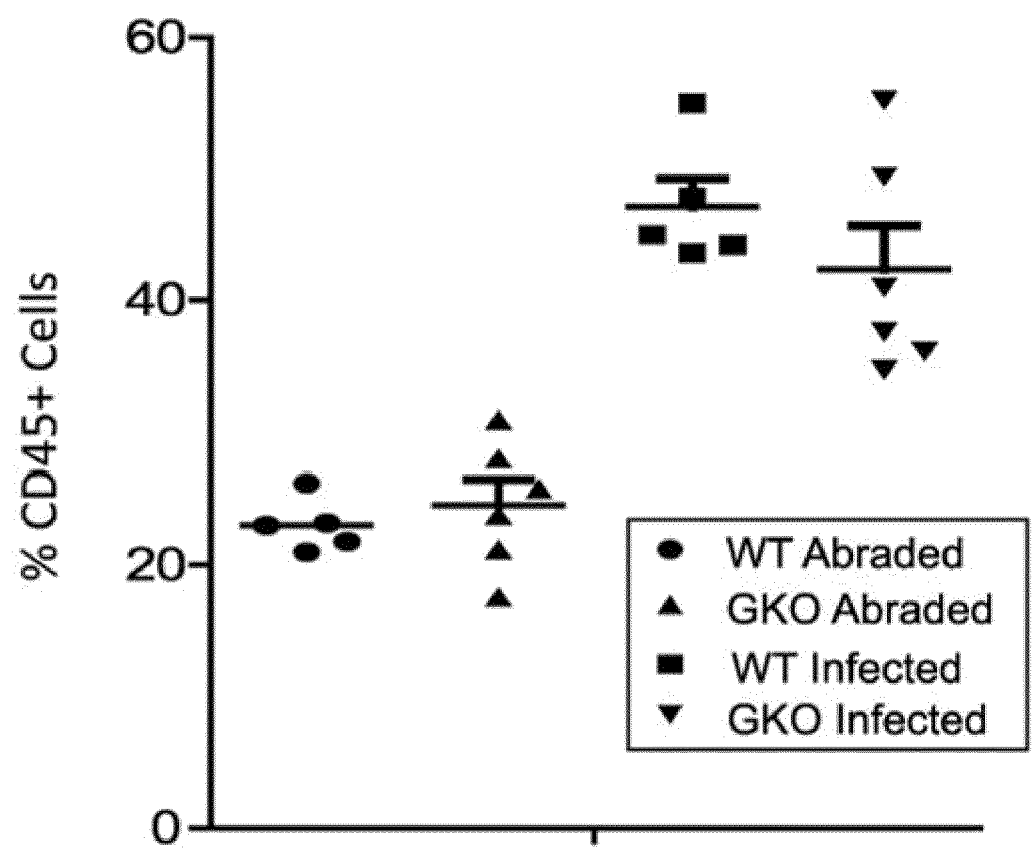
Figure 7D:
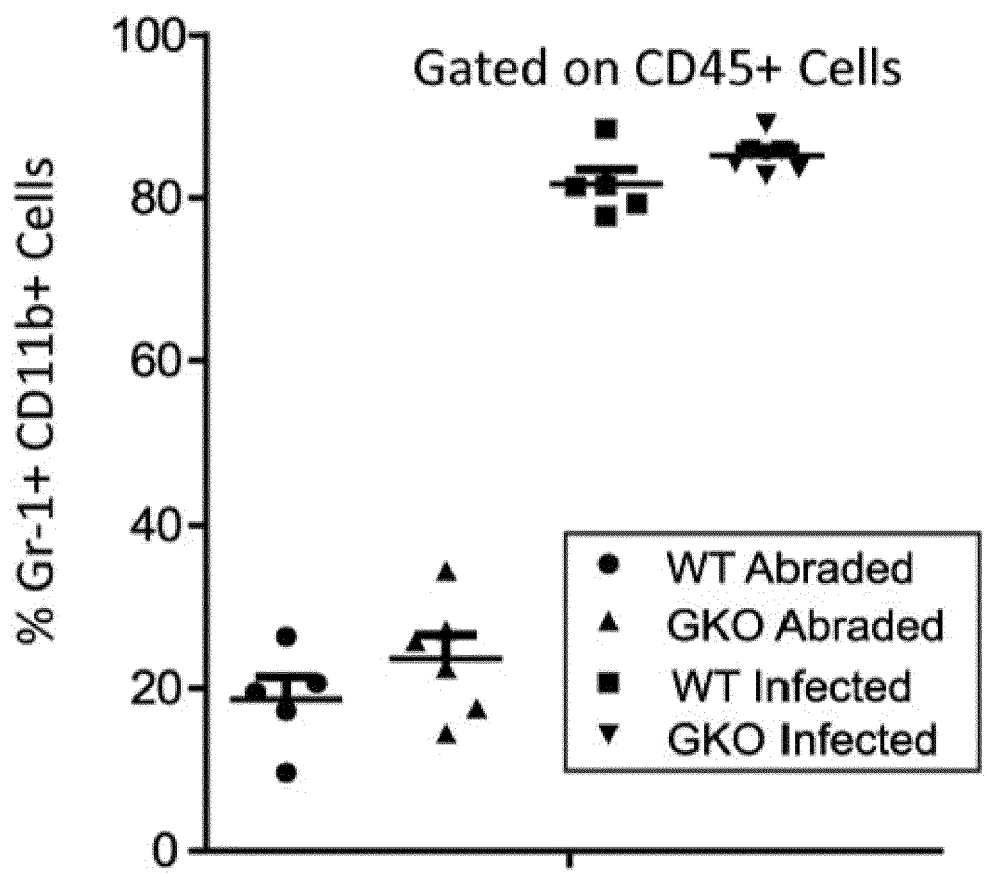

Interferon-γ (IFN-γ) and interleukin 13 (IL-13) suppress Slurp1 (Mastrangeli et al., *Eur J Dermatol* 2003; 13:560-570, Narumoto et al., *Biochem Biophys Res Commun* 2010; 398: 713-718). Many inflammatory cytokines are upregulated in Klf4CN corneas lacking Slurp1 (Table 1; FIG. 2). Slurp1 was down-regulated in HSV-1 infected and LPS-injected corneas in the presence of normal levels of Klf4 (FIG. 5). Thus, inflammatory cytokines could selectively inhibit Slurp1 production without affecting Klf4. Consistent with this, treatment of HCLE cells with IL-4, IL-13 and TNF-α suppressed SLURP1 production, while IFN-γ did not affect SLURP1 levels significantly (FIG. 7A). It was determined if elevated levels of IFN-γ play a role in downregulation of Slurp1 in HSV-1 infected corneas by measuring the Klf4 and Slurp1 levels in abraded or HSV-1 infected WT and IFN-γ knockout (GKO) mice. At 2 DPI, both the extent of Slurp1 downregulation and the nature of leukocytic infiltrate was comparable between the WT and GKO corneas (FIGS. 7B, C and D; Table 2B), suggesting that IFN-γ is not involved in down-regulation of Slurp1 in HSV-1-infected corneas. Thus, in pro-inflammatory conditions, SLURP1 expression is inhibited by cytokines IL-4, IL-13 and TNF-α, but not IFN-γ.

Example 9

Slurp1 Restricts Neutrophilic Infiltrate in Adenovirus-Infected Corneas

Figure 8A:
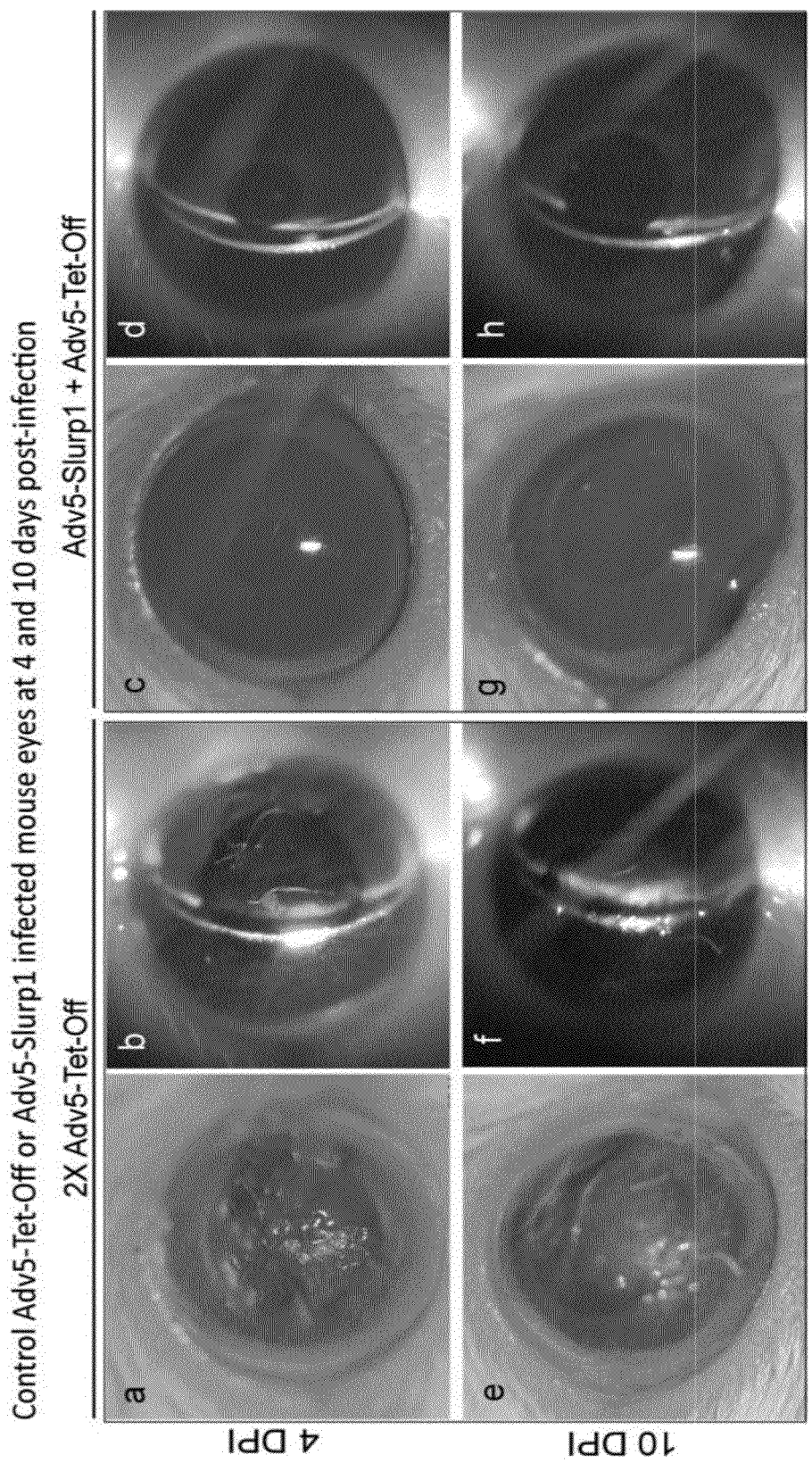
FIGS. 8A-8D. Evidence for immunomodulatory role for Slurp1. WT BALB/c mouse corneas (n=4) abraded and infected with either 2×10$^6$ PFU Adv5-Tet-Off vector alone (a, b, e, f) or 10$^6$ PFU each of Adv5-Slurp1 and Adv5-Tet-Off vectors (c, d, g, h) were imaged 4 and 10 DPI under normal (a, e, c, g) and slit-lamp (b, f, d, h) illumination (A). Signs of mild inflammation were observed in corneas infected with Adv5-Tet-Off vector alone, while those infected with Adv5-Slurp1 and Adv5-Tet-Off vectors remained normal (A). Corneas harvested at 4 DPI were separated into epithelium and stroma+endothelium. Total RNA isolated from epithelial cells was used to quantify relative expression of Slurp1 by QPCR (B). Stromal cells were isolated and stained with fluorochrome-conjugated antibodies specific for CD45, CD11b and Gr-1, and analyzed by flow cytometry (C and D). Number of CD45+ (C) and CD11b$^+$ Gr-1$^+$ cells (D) was significantly reduced in Adv5-Slurp1 infected corneas compared with those infected with Adv5-Tet-Off vector (control) alone.
Figure 8B:
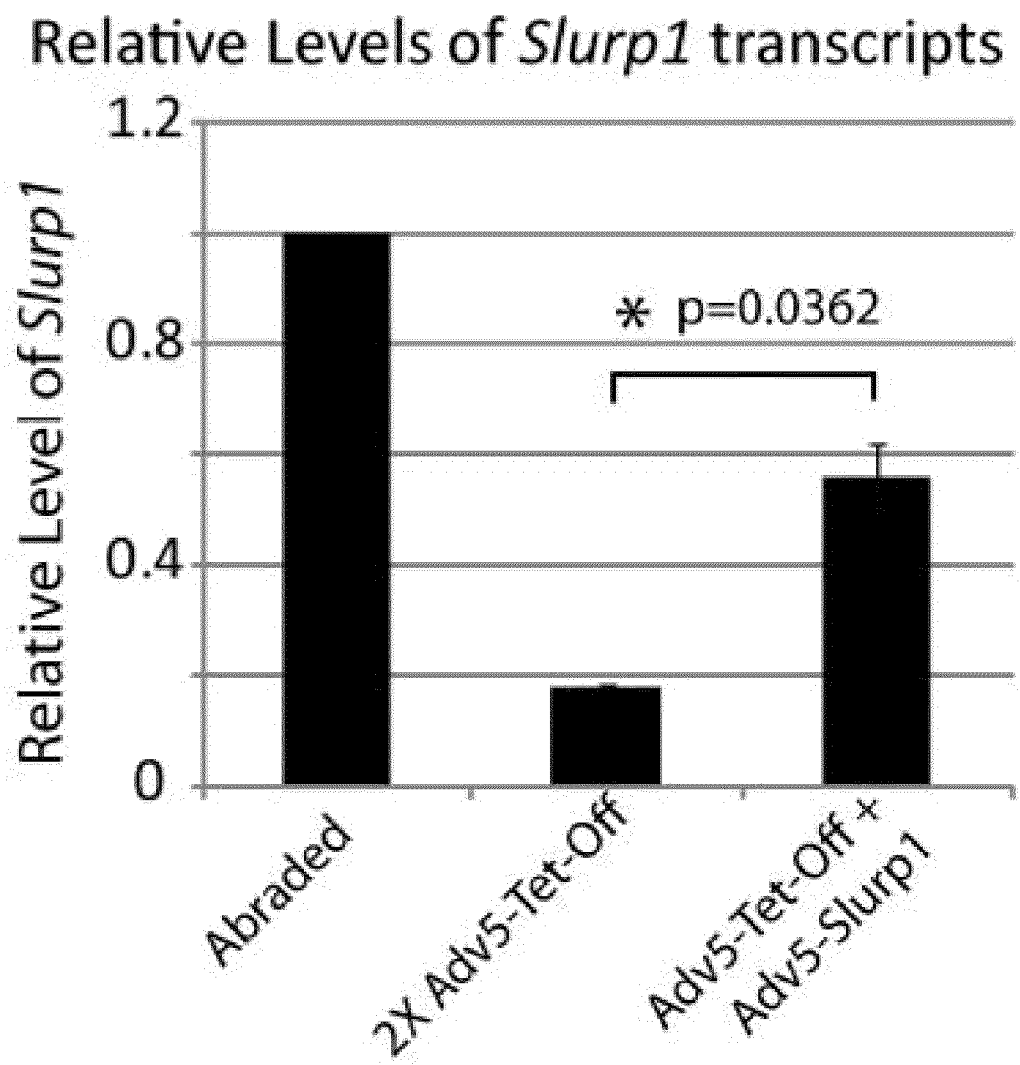
Figure 8C:
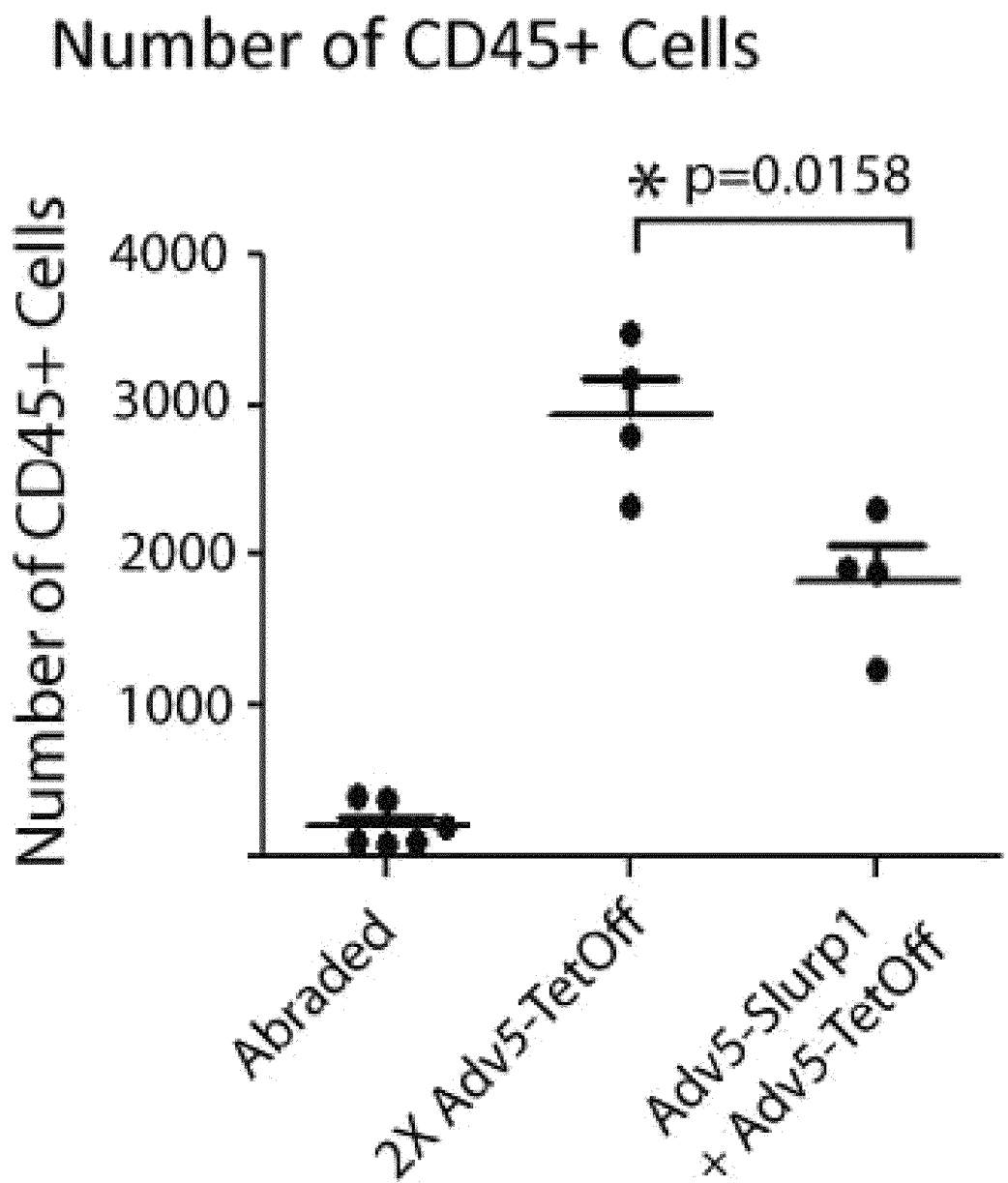
Figure 8D:
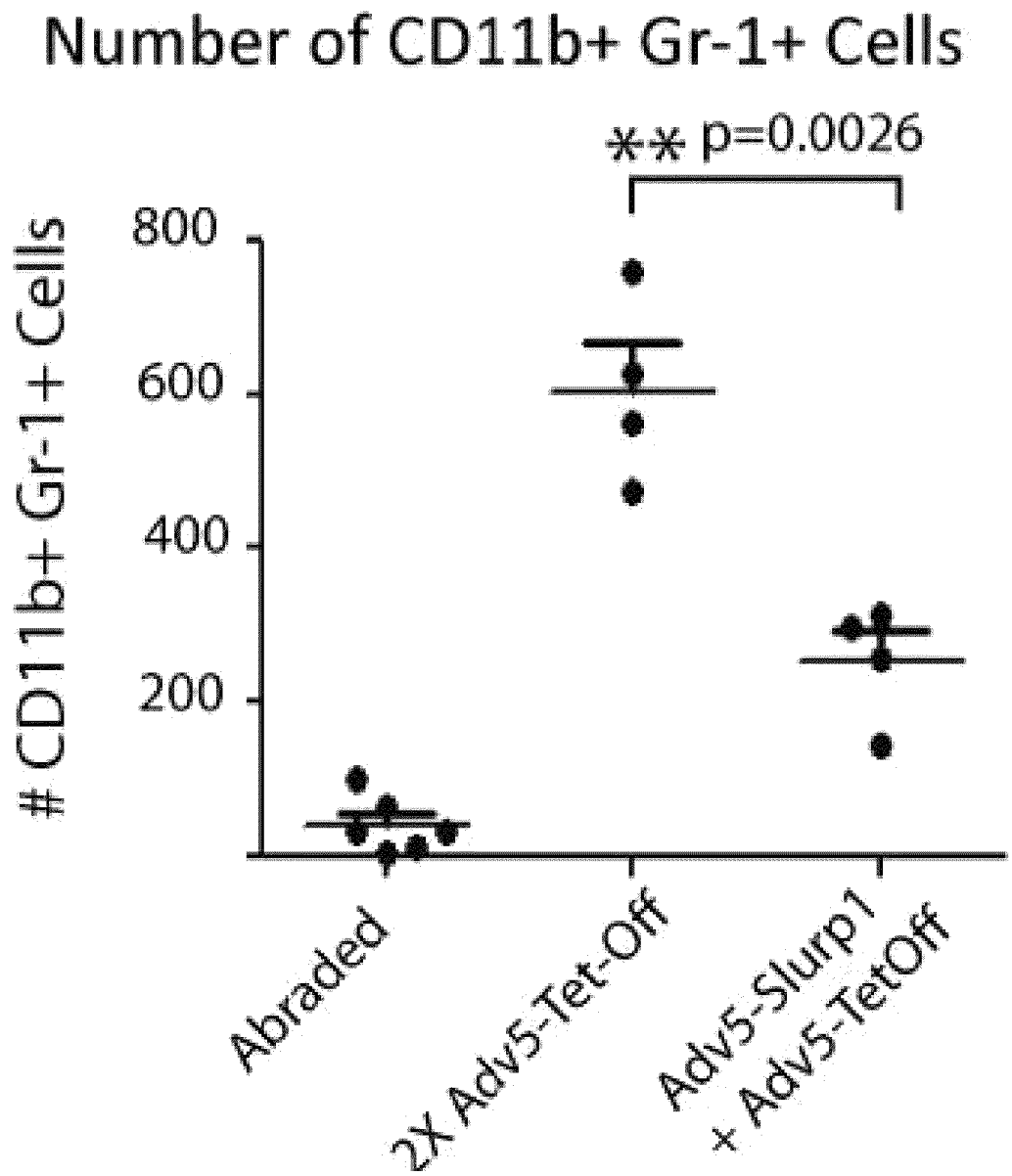

In order to directly test the immunomodulatory role of Slurp1, an adenoviral vector (serotype-5) expressing Slurp1 under the control of CMV promoter (Adv5-Slurp1) was generated. Wild-type (WT) BALB/c mouse corneas were abraded and infected with control Adv5-Tet-Off vector alone ($2 \times 10^6$ plaque forming units (PFU)/cornea) or Adv5-Slurp1 and Adv5-Tet-Off vectors ($10^6$ PFU each/cornea). Examination of the infected eyes at 4 and 10 DPI through a slit-lamp biomicroscope revealed signs of mild inflammation in corneas infected with Adv5-Tet-Off vector alone, while those infected with Adv5-Slurp1 and Adv5-Tet-Off vectors remained normal (FIG. 8A). The corneas were harvested from these mice at 4 DPI, and Slurp1 expression in epithelial cells was estimated by QPCR. In parallel, the nature of leukocytic infiltrate in corresponding corneal stromas was assessed by flow cytometry as above. Slurp1 expression in Adv5-Tet-Off virus infected corneas was reduced to 17% of that in the abraded corneas, and was partially restored in Adv5-Tet-Off and Adv5-Slurp1 co-infected corneas, to 55% of that in the abraded corneas (FIG. 8B). The reduced expression of Slurp1 in Adv5-Tet-Off virus infected corneas was accompanied by significantly elevated neutrophilic infiltrate, compared with the small number of neutrophils identified in control abraded corneas expressing normal levels of Slurp1 (FIGS. 8C and D). Partial restoration of Slurp1 expression in Adv5-Slurp1 and Adv5-Tet-Off co-infected corneas significantly restricted the neutrophilic infiltrate (FIG. 8B). These results, taken together with those described above with HSV-1 infected, LPS-injected and Klf4CN corneas, provide additional evidence of the immunomodulatory role for Slurp1.

It is demonstrated herein that Slurp1 expression is (i) increased upon mouse eyelid opening when the cornea is first exposed to the environment, (ii) decreased in inflamed Klf4CN corneas, (iii) critically dependent on the transcription factor Klf4, (iv) abrogated upon bacterial LPS injection, HSV-1, or adenoviral infection, (v) suppressed by pro-inflammatory cytokines IL-4, IL-13 and TNF-α, and (vi) capable of restricting neutrophilic infiltrate in adenovirus infected corneas. Taken together, the results provide the necessary evidence that Slurp1 is a key immunomodulatory molecule that contributes to corneal immune privilege by suppressing leukocyte infiltration in healthy corneas, and that is rapidly down-regulated in acute inflammatory conditions to allow protective inflammation to develop.

The findings demonstrate the relationship between reduced Slurp1 and increased inflammation. Without being bound by theory, it is possible that increased inflammation in the Klf4CN corneas is directly related to reduced Slurp1 expression, as Klf4 modulates the expression of many genes including Slurp1 (Swamynathan et al., *Invest Ophthalmol Vis Sci* 2011; 52:1762-1769, Swamynathan et al., *Invest Ophthalmol Vis Sci* 2008; 49:3360-3370, Swamynathan et al., *Mol Cell Biol* 2007; 27:182-194). Moreover, the absence of conjunctival goblet cells (Swamynathan et al., *Mol Cell Biol* 2007; 27:182-194) and the loss of corneal epithelial barrier function (Swamynathan et al., *Invest Ophthalmol Vis Sci* 2011; 52:1762-1769) can also generate pro-inflammatory signals in the Klf4CN ocular surface.

The concept of corneal immune privilege arose from the antithetical nature of inflammation and essential corneal transparence (Niederkorn et al., *Ocul Immunol Inflamm* 2010; 18:19-23, Azar et al., *Trans Am Ophthalmol Soc* 2006; 104: 264-302, Hazlett et al., *Ocul Immunol Inflamm* 2010; 18:237-243, Barabino et al., *Prog Retin Eye Res* 2012; 31:271-285, Clements et al., *Semin Ophthalmol* 2011; 26:235-245, Yamanaka et al., *Endocr Metab Immune Disord Drug Targets* 2010; 10:331-335, Gronert et al., *Exp Eye Res* 2010; 91:478-485, Ambati et al., *Nature* 2006; 443:993-997, Cursiefen et al., *Proc Natl Acad Sci USA* 2006; 103:11405-11410, Stuart et al., *Invest Ophthalmol Vis Sci* 2003; 44:93-98, Morris et al., *J Immunol* 2012; 188:793-799, Jin et al., *Am J Pathol* 2011; 178:1922-1929, El Annan et al., *Invest Ophthalmol Vis Sci* 2010; 51:3418-3423, Tandon et al., *Curr Mol Med* 2010; 10:565-578). As it is the most anterior part of the eye, the cornea is constantly exposed to various biological, chemical and physical insults. The requirement for its transparence to ensure proper vision mandates that the cornea be kept free of chronic inflammation in the presence of mild but constant insults. Corneal cells constitutively express a variety of molecules that function to inhibit important components of the inflammatory response. For instance, the avascular nature of the cornea is maintained in part by the constitutive production of soluble vascular endothelial growth factor (VEGF) receptor-1 (sVEGF-R1) and -3 (VEGF-R3) that inhibit the angiogenic activity of VEGF (Azar et al., *Trans Am Ophthalmol Soc* 2006; 104:264-302, Ambati et al., *Nature* 2006; 443:993-997, Cursiefen et al., *Proc Natl Acad Sci USA* 2006; 103:11405-11410). The cornea constitutively expresses surface molecules such as FAS ligand and Programmed Death Ligand 1 (PD-L1) that can inhibit or kill infiltrating leukocytes (Stuart et al., *Invest Ophthalmol Vis Sci* 2003; 44:93-98, Morris et al., *J Immunol* 2012; 188:793-799, Jin et al., *Am J Pathol* 2011; 178:1922-1929, El Annan et al., *Invest Ophthalmol Vis Sci* 2010; 51:3418-3423, Keir et al., *Annu Rev Immunol* 2008; 26:677-704), and secreted molecules such as transforming growth factor beta that potently inhibits the function of a variety of inflammatory cells (Tandon et al., *Curr Mol Med* 2010; 10:565-578). It is documented herein that Slurp1 is a constitutively expressed molecule that inhibits inflammatory response in the cornea.

Figure 9A:
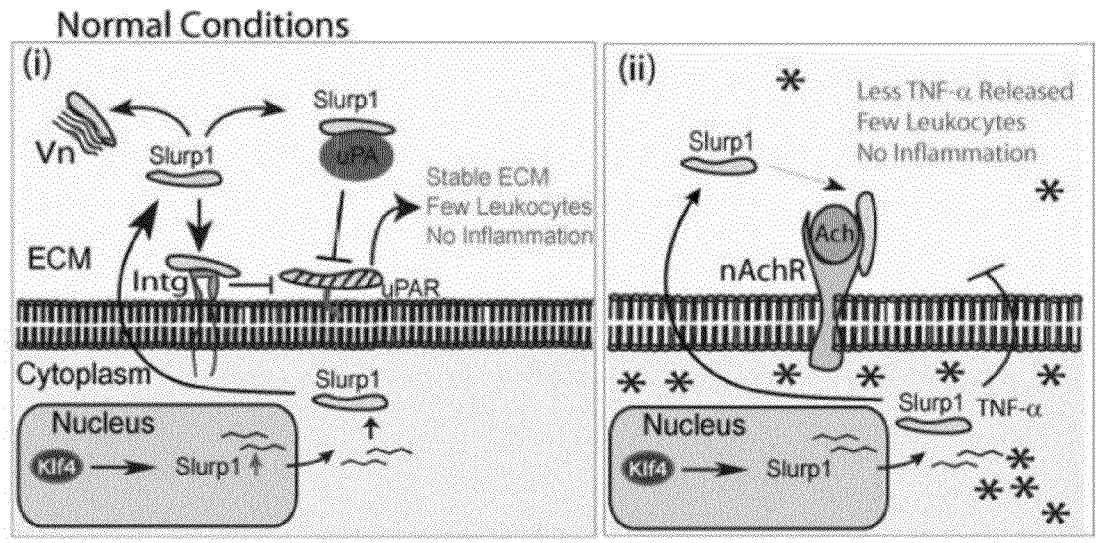
FIGS. 9A-9B. Proposed model for the function of Slurp1 in the ocular surface. Slurp1 is a part of the machinery that suppresses inflammation at the ocular surface. A. Under normal conditions or conditions of mild trauma, Klf4 supports constitutive high level production of Slurp1 by the corneal epithelium. Slurp1 can (i) block urokinase-type plasminogen activator receptor (uPAR) function by competing for its ligands urokinase-type plasminogen activator (uPA), vitronectin (Vn) and integrins (Intg), and/or (ii) interact with membrane-bound nicotinic acetylcholine receptor (nAchR) on the surface of resident corneal cells such as macrophages and dendritic cells, potentiating the ability of acetylcholine (bound to nAchR) to block the release of intracellular TNF-α, maintaining the cornea in a non-inflamed state. B. Under severe trauma or microbial infection favoring inflammation, Slurp1 production is rapidly reduced by pro-inflammatory cytokines, facilitating (iii) uPAR-mediated extracellular matrix (ECM) degradation and/or (iv) the release of intracellular cytokines such as TNF-α, culminating in neutrophilic infiltration.
Figure 9B:
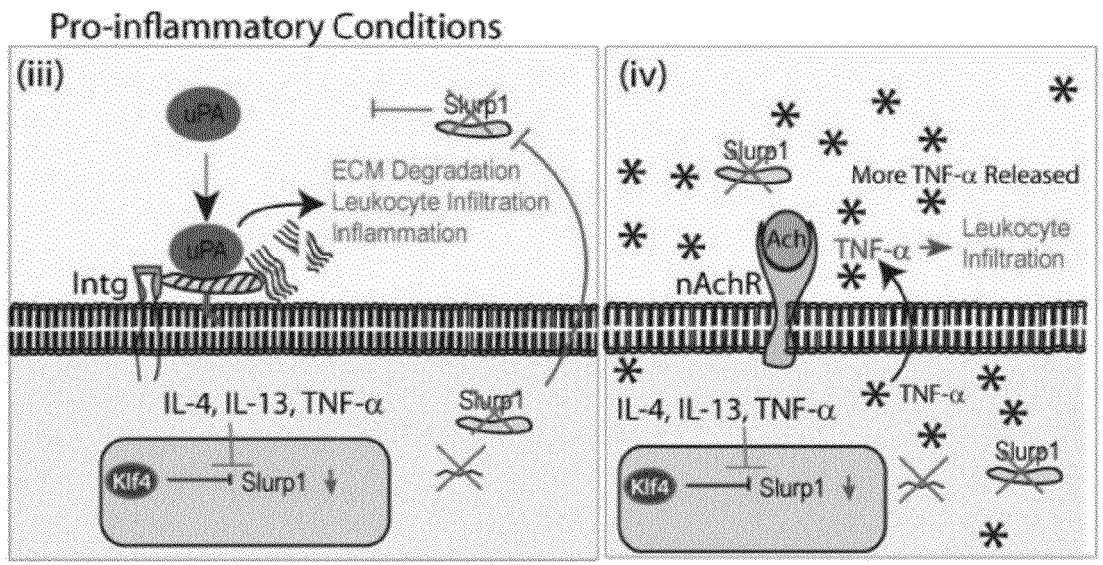
Figure 10:
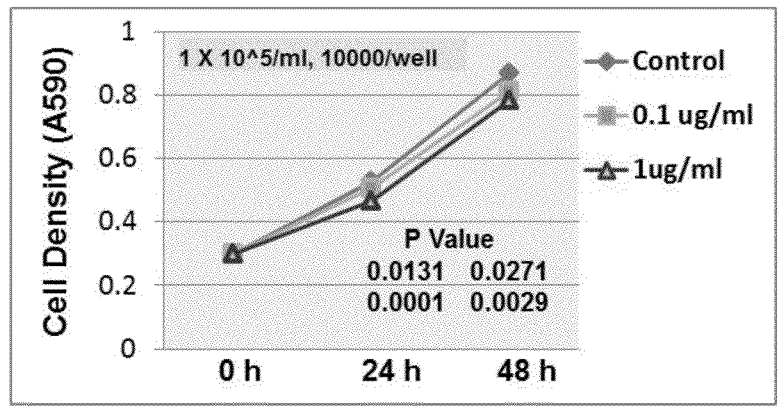
FIG. 10. Effect of Slurp1 on mouse corneal fibroblast MK/T-1 cell proliferation. MK/T-1 cells were seeded in a tissue culture-treated 96 well plate. One set was removed for staining 4 hours after plating (0 h). For the rest, Slurp1 was added at 0, 0.1 or 1 mg/ml in 100 µl medium with 5% FBS. Fresh medium with/without Slurp1 was added at 24 h interval as required. Cells were fixed and stained with crystal violet at appropriate times and absorbance measured at 590 nm. The presence of Slurp1 decreased the rate at which MK/T-1 cells proliferated.
Figure 11:
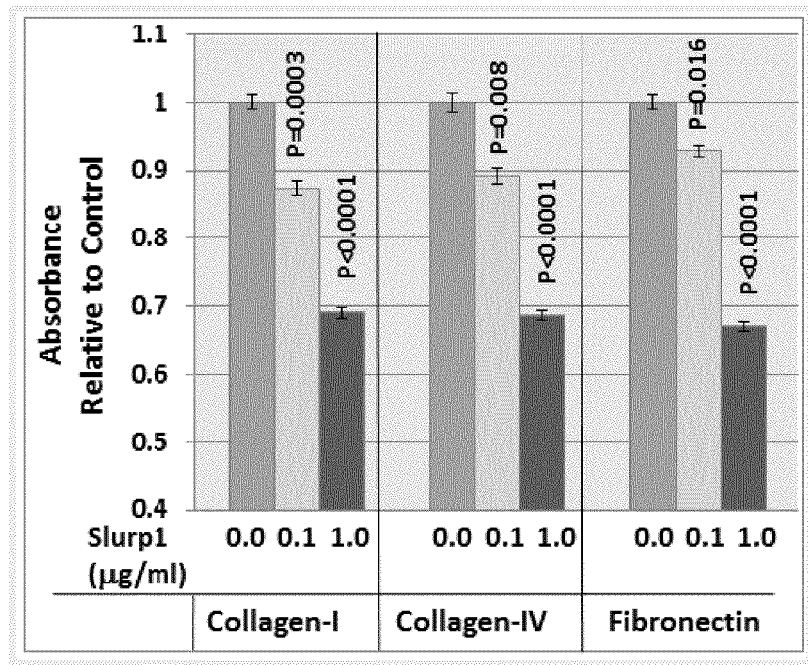
FIG. 11. Effect of Slurp1 on adhesion of MK/T-1 cells to collagen-I-, -IV- and fibronectin-coated surfaces. MK/T-1 cells were harvested using 0.4 mM EDTA (Trypsin was not used to avoid digestion of membrane-bound proteins). The cells were incubated for 1 h at 37° C. with increasing amounts of Slurp1 on collagen-I, collagen-IV, or fibronectin coated plates blocked with BSA, washed, and adherent cell density estimated by crystal violet staining and measuring A590. Slurp1 was found to inhibit MK/T-1 cells adhesion to collagen-I, -IV and fibronectin. The presence of Slurp1 decreased the adhesion of MK/T-1 cells to three different components of the extracellular matrix tested.
Figure 12:
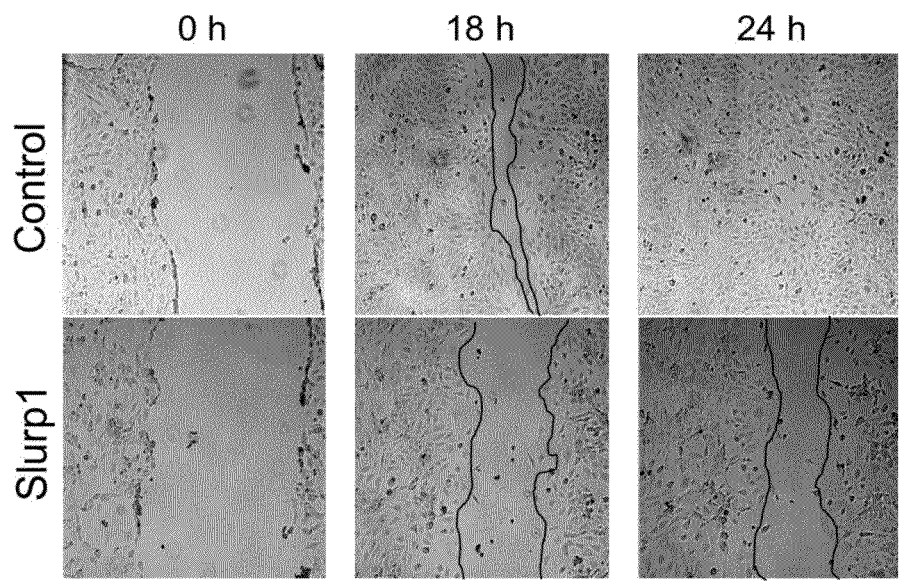
FIG. 12. Effect of Slurp1 on MK/T-1 cell migration in in vitro gap filling assays. MK/T-1 cells were infected with either 2× Tet-Off helper adenovirus (control), or 1× each of Slurp1-expressing adenovirus and Tet-Off helper adenovirus (Slurp1). One day later, when the cells were confluent, a gap was generated by streaking with a 200 μl pipette tip. Gap filling by migration was monitored at 0 h, 18 h and 24 h post-gap generation. By 24 h, roughly 50% of the gap remains open in cells infected with Slurp1-expressing adenovirus while the gap in control virus infected cells is completely filled.
Figure 13:
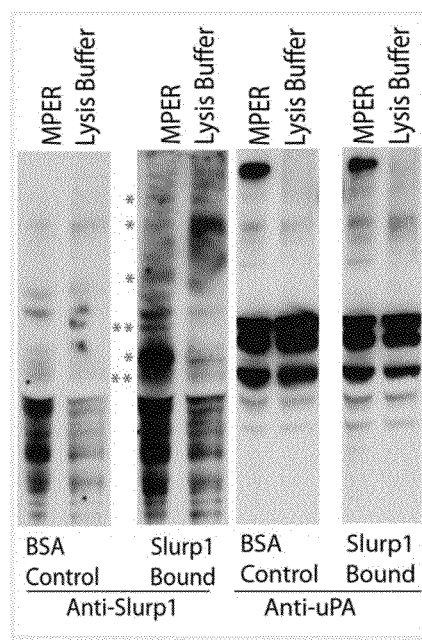
FIG. 13. Ligand-binding assay to identify Slurp1-interacting proteins. Kidney cells, which express Slurp1 and many uPAR ligands, and offer the advantage of relatively abundant tissue availability, were used to screen for Slurp1-interacting proteins. Kidney lysates were prepared using either homemade Lysis Buffer (20 mM Tris-HCl (pH 8.0), 150 mM NaCl, 1 mM phenylmethylsulfonyl fluoride (PMSF), 0.25% Tween-20) or M-PER (A non-denaturing commercial detergent formulation that extracts soluble protein). Kidney lysates were separated by non-denaturing PAGE, transferred to nitrocellulose membrane, blocked with 5% milk in phosphate buffered Tris saline (PBST), incubated with bovine serum alubumin (BSA) or partially purified His-Slurp1 (expressed in *E. coli*), and probed with anti-Slurp1 antibody to detect Slurp1-binding proteins (*). Blots were stripped and re-probed with anti-uPA antibody, and aligned with each other to detect Slurp1-interacting protein bands overlapping with those detected by anti-uPA antibody (**). There were additional Slurp1-interacting proteins (*).
Figure 16A:
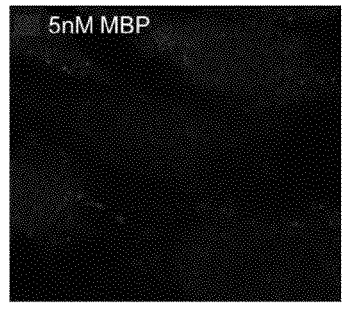
FIGS. 16A-16D. Slurp1 decreases the amount of cell surface bound uPA in quiescent and migrating MK/T-1 cells. MK/T-1 cells were plated on collagen coated coverslip, surface bound uPA removed by acid wash (0.05M glycine, pH-3.0) and neutralized by Hepes solution, and blocked with BSA. The cells were then treated with MBP or uPA, with or without Slurp1 for 10 minutes, washed with PBS, and immunofluorescence was performed with anti-uPA antibody. The number of foci on cell surface increased with uPA addition (panel B compared with panel A), and this increase was not seen when Slurp1 is added along with uPA (panel D compared with panel C).
Figure 16B:
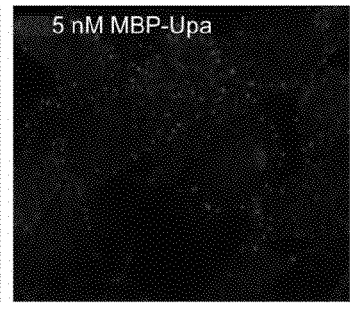
Figure 16C:
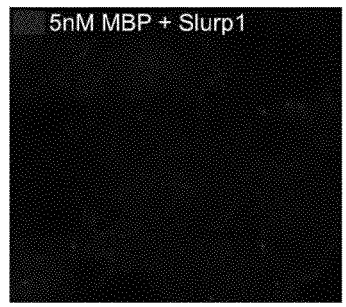
Figure 16D:
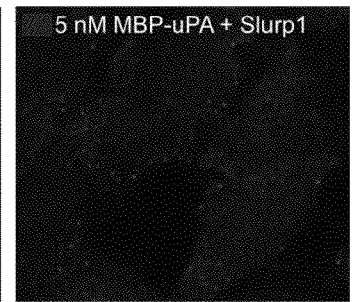
Figure 17:
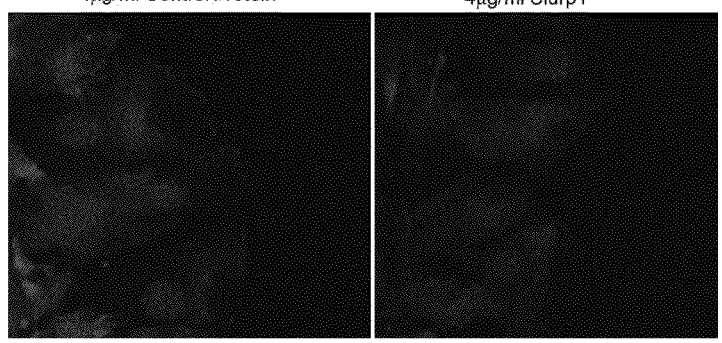
FIG. 17. Slurp1 decreases the amount of cell surface bound uPA in leading edges of migrating MK/T-1 cells. Following introduction of linear gaps in confluent MK/T-1 cells with a 200 μl pipette tip, the cells were treated with Slurp1 or control protein for 4 hours, at the end of which uPA was detected in the leading edges by immunofluorescence with rabbit anti-uPA antibody. While uPA was detected in the leading edges of control protein treated migrating cells, it was markedly decreased in those treated with Slurp1.
Figure 18:
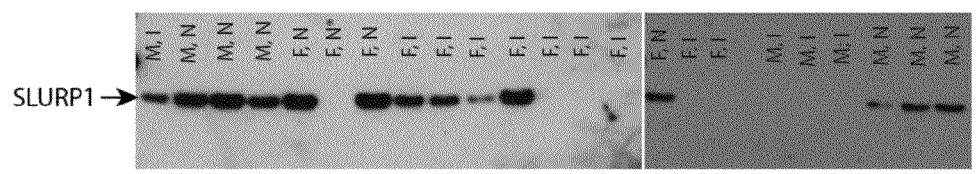
FIG. 18. Slurp1 expression is decreased in tears from inflamed human ocular surface. Tears were collected from male (M) or female (F) human volunteers with normal (N) or inflamed (I) ocular surface (cause of inflammation was not distinguished) following informed consent. In a single-blind experiment, equal amount of tear proteins were separated by SDS-PAGE, transferred to PVDF membrane and immunoblot performed with goat anti-human SLURP1 antibody. While abundant SLURP1 expression was detected in tears from normal ocular surface, it was either decreased or completely absent in tears from inflamed human ocular surface, regardless of the gender.

Without being bound by theory, Slurp1 is a part of the mechanism that prevents neutrophil infiltration into the normal cornea by one or both of the pathways depicted in FIG. 9. The first scenario predicts that Slurp1, which is structurally similar to membrane-tethered uPAR required for neutrophil recruitment in response to bacterial infections (Gyetko et al., *J Immunol* 2000; 165:1513-1519, Rijneveld et al., *J Immunol* 2002; 168:3507-3511, Smith et al., *Nat Rev Mol Cell Biol* 2010; 11:23-36), functions as a soluble scavenger of uPAR ligands and blocks its functions, analogous to the role of soluble VEGFR in blocking corneal angiogenesis (Ambati et al., *Nature* 2006; 443:993-997) (FIG. 9A, i). Although uPAR-mediated neutrophil recruitment is independent of uPA, (Gueler et al., *J Immunol* 2008; 181:1179-1189, Connolly et al., *Blood* 2010; 116:1593-1603), other activities of uPAR such as its interaction with vitronectin and b1-integrin, and bacterial clearance are dependent on uPA (Connolly et al., *Blood* 2010; 116:1593-1603, Nguyen et al., *J Cell Biol* 1999; 146:149-164, Sidenius et al., *J Biol Chem* 2002; 277:27982-27990, Caiolfa et al., *J Cell Biol* 2007; 179:1067-1082). The second scenario predicts that Slurp1, which shares the structural features of α-bungarotoxin and serves as a ligand for the α7nAchRs (Arredondo et al., *J Invest Dermatol* 2005; 125: 1236-1241), suppresses the release of inflammatory mediators such as TNF-α from macrophages by enhancing α7nAChR mediated responses (Moriwaki et al., *Neurosci Res* 2009; 64:403-412) (FIG. 9A, ii). Normal mouse corneas possess a network of stromal macrophages and a sparse population of dendritic cells (Brissette-Storkus et al., *Invest Ophthalmol Vis Sci* 2002; 43:2264-2271, Knickelbein et al., *Ophthalmol Eye Dis* 2009; 1:45-54, Hamrah et al., *Int Ophthalmol Clin* 2009; 49:53-62), which are likely to express α7nAchR (Kawashima et al., *Life Sci* 2007; 80:2314-2319), ligation of which results in inhibition of cytokine and chemokine release (Grando et al., *J Pharmacol Sci* 2008; 106:174-179). In either scenario, when the cornea needs to mount a rapid immune response to deal with acute infections or severe chemical or physical insults, downregulation of Slurp1 serves as a molecular switch facilitating further progression of inflammation (FIG. 9B). This role of Slurp1 as a molecular switch regulating inflammation may not be limited to the cornea; it may serve a similar function in the other epithelia where it is abundantly expressed.

An important observation is that the resident population of bone marrow-derived $CD45^+$ cells is altered in Klf4CN corneas that lack Slurp1. The resident leukocyte population in these corneas is not only larger, but is also phenotypically distinct from that found in normal corneas of WT mice. While WT corneal stromas contain mainly $CD11b^+$ $Gr-1^-$ macrophages, those of Klf4CN mice lacking Slurp1 expression contain a population of $CD11b^+$ Gr-1– cells, a phenotype characteristic of neutrophils. As eosinophils express CD11b and Gr-1 (Rothenberg et al., *Annu Rev Immunol* 2006; 24:147-174), a contribution of eosinophils to the leukocytic population in corneas of Klf4CN mice cannot be ruled out. The chemokine showing the greatest up-regulation in non-infected Klf4CN corneas is CXCL5, a chemokine that is induced by IL-1 and TNF-α and is a potent chemoattractant for neutrophils. In addition, two of the three most up-regulated chemokines in non-infected Klf4CN corneas relative to WT corneas are chemotactic for neutrophils (Table 1). The Klf4CN corneas also exhibited increased expression of the type 2 cytokines IL-4 and IL-13, and the chemokine CCL11, all known to attract and activate eosinophils. As IL-4 and IL-13 inhibit Slurp 1 expression, the reduced expression of Slurp1 1 in the Klf4CN mouse corneas could reflect the cumulative effect of the absence of Klf4 and elevated levels of IL-4 and IL-13.

Mock infection of the WT corneas involving abrasion of the corneal epithelium did not reduce Slurp1 expression. These corneas showed few if any cells expressing a neutrophil phenotype. HSV-1 infection of the mouse corneas resulted in a rapid infiltration of leukocytes consisting primarily of neutrophils, consistent with the previous reports (Hendricks et al., *Invest Ophthalmol Vis Sci* 1990; 31:1929-1939). It was hypothesized that Slurp1 expression would have to be down-regulated to permit neutrophil infiltration into HSV-1 infected corneas. It was found that Slurp1 expression is abrogated in the cornea by 24 h after HSV-1 corneal infection, and Slurp1 down-regulation was associated with a leukocytic infiltrate predominated by neutrophils.

Interestingly, Slurp1 down-regulation in corneas 24 h after infection occurred in the presence of relatively unchanged levels of Klf4, indicating that the early reduction in Slurp1 was not due to a deficiency in Klf4. Slurp1 was virtually abrogated, even though only a portion of corneal epithelial cells were infected by the virus, suggesting that down-regulation of Slurp1 does not require direct infection of corneal epithelial cells. Without being bound by theory, it seems likely that suppression of Slurp1 expression is mediated by a soluble mediator that is induced by HSV-1 infection. IL-4, IL-13 and TNFα-mediated suppression of Slurp1 expression without perturbing Klf4 levels is consistent with this likelihood. Even though IFN-γ is rapidly produced in the cornea following HSV-1 infection (Hendricks et al., *J Immunol* 1992; 149:3023-3028), and inhibits Slurp1 expression in vitro (Mastrangeli et al., *Eur J Dermatol* 2003; 13:560-570), the results presented herein demonstrate that IFN-γ is not involved in down-regulation of Slurp1 following corneal infection with HSV-1. This is most likely due to overlapping effects of other inflammatory cytokines.

Mutations or deletions in SLURP1 gene are associated with Mal de Meleda, a rare autosomal recessive palmoplantar hyperkeratotic disorder in humans (Mastrangeli et al., *Eur J Dermatol* 2003; 13:560-570, Favre et al., *J Invest Dermatol* 2007; 127:301-308, Chimienti et al., *Hum Mol Genet* 2003; 12:3017-3024, Fischer et al., *Hum Mol Genet* 2001; 10:875-880, Eckl et al., *Hum Genet* 2003; 112:50-56, Hu et al., *J Invest Dermatol* 2003; 120:967-969, Marrakchi et al., *J Invest Dermatol* 2003; 120:351-355, Ward et al., *J Invest Dermatol* 2003; 120:96-98). Although diverse inflammatory keratodermas are often associated with ocular surface defects (Messmer et al., *Ophthalmology* 2005; 112:e1-6, Mohammad et al., *Pediatr Dermatol* 2009; 26:113-115, Sonoda et al., *Am J Ophthalmol* 2004; 137:181-183), no such defects have been described so far in Mal de Meleda patients.

It is demonstrated herein that Klf4 regulates the expression of Slurp1, a key immunomodulatory molecule that is abundantly expressed in the healthy cornea, and that is rapidly downregulated in pro-inflammatory conditions. Regulation of expression of Slurp1 is a mechanism in which Klf4 contributes to maintenance of the corneal homeostasis. SLURP1 is identified herein as a novel target for therapeutic intervention in managing corneal inflammatory disorders of diverse etiologies. SLURP1 is expressed in other tissues such as skin, oral mucosa, intestine, lung, and cervical epithelium. Thus, SLURP1 can be used in findings and conclusions in other epithelia frequently exposed to similar insults as the ocular surface.

It is demonstrated herein that Slurp1 modulates corneal fibroblast M/KT-1 cell (i) proliferation, (ii) adhesion to different components of the extracellular matrix, and (iii) migration in in vitro gap-filling assays. It is also demonstrated herein that Slurp1 interacts with uPA, and reduces the amount of cell surface-bound uPA, providing evidence that Slurp1 serves as a soluble scavenger of uPAR ligands. Finally, it is demonstrated that the expression of SLURP1 in human tears is dependent on the ocular surface health, indicating that our findings with the mouse model system are generally applicable in humans (see FIGS. 10-18).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating keratitis in a subject, comprising selecting a subject with keratitis, and
administering locally to the cornea of the subject a therapeutically effective amount of a nucleic acid encoding the SLURP1 polypeptide operably linked to a regulatory sequence, wherein the SLURP1 polypeptide comprises an amino acid sequence at least 95% identical to the amino acid sequence set forth as amino acids 23-103 of SEQ ID NO: 1, wherein the SLURP1 polypeptide is expressed in the cornea, thereby treating the keratitis subject.

2. The method of claim 1, wherein the subject is a human.

3. The method of claim 1, wherein the keratitis is bacterial keratitis.

4. The method of claim 1, wherein the keratitis is viral keratitis.

5. The method of claim 1, wherein the keratitis results from laser eye therapy, trauma, exposure to ultraviolet light, exposure to chemical stimuli, contact lens wear, corneal transplant, or exposure to a toxin.

6. The method of claim 1, wherein the keratitis is ulcerative.

7. The method of claim 1, wherein the nucleic acid encoding the SLURP1 polypeptide is administered topically.

8. The method of claim 1, wherein the nucleic acid encoding the SLURP1 polypeptide is administered in an ophthalmic solution or ointment.

9. The method of claim 1, further comprising administering an additional anti-inflammatory agent to the subject.

10. The method of claim 1, wherein the nucleic acid encoding SLURP1 is operably linked to a heterologous constitutive promoter.

11. The method of claim 1, comprising administering to the subject a therapeutically effective amount of a replication defective adenoviral vector comprising the nucleic acid encoding SLURP1.

12. The method of claim 11, wherein the adenoviral vector is administered topically to the eye.

13. The method of claim 12, wherein the vector is administered in an ophthalmic solution or ointment.

14. The method of claim 1, wherein administration of the therapeutically effective amount of the nucleic acid encoding the SLURP1 polypeptide reduces neutrophil infiltration in the cornea.

15. The method of claim 1, wherein the keratitis is caused by a bacteria, and wherein the method further comprises administering to the subject a therapeutically effective amount of an antibacterial agent.

16. The method of claim 1, wherein the SLURP1 polypeptide comprises the amino acid sequence set forth as SEQ ID NO: 1.

17. The method of claim 11, wherein the SLURP1 polypeptide comprises the amino acid sequence set forth as SEQ ID NO: 1.

18. The method of claim 13, wherein the SLURP1 polypeptide comprises the amino acid sequence set forth as SEQ ID NO: 1.

19. A method of reducing neutrophil infiltration in a cornea of a subject with corneal inflammation, comprising
selecting a subject with an elevated number of leukocytes in the cornea resulting from a microbial infection of the cornea, a viral infection of the cornea, a fungal infection of the cornea, or an autoimmune disease causing corneal inflammation,
wherein the elevated number of leukocytes comprises neutrophil infiltration in the cornea, and administering locally to the cornea of the subject a therapeutically effective amount of a viral vector comprising a nucleic acid encoding a SLURP1 polypeptide operably linked to a regulatory sequence, wherein the SLURP1 polypeptide comprises an amino acid sequence at least 95% identical to the amino acid sequence set forth as amino acids 23-103 of SEQ ID NO: 1, and
wherein the SLURP1 polypeptide is expressed in the cornea, thereby reducing neutrophil infiltration in the cornea of the subject with corneal inflammation.

20. The method of claim 19, wherein the SLURP1 polypeptide comprises the amino acid sequence set forth as SEQ ID NO: 1.

21. The method of claim 19, wherein the vector is an adenoviral vector.

* * * * *

SEQUENCE LISTING

<160> NUMBER OF SEQ ID NOS: 7

<210> SEQ ID NO 1
<211> LENGTH: 103
<212> TYPE: PRT
<213> ORGANISM: Homo sapiens

<400> SEQUENCE: 1

Met Ala Ser Arg Trp Ala Val Gln Leu Leu Leu Val Ala Ala Trp Ser
1               5                   10                  15

Met Gly Cys Gly Glu Ala Leu Lys Cys Tyr Thr Cys Lys Glu Pro Met
            20                  25                  30

Thr Ser Ala Ser Cys Arg Thr Ile Thr Arg Cys Lys Pro Glu Asp Thr
        35                  40                  45

Ala Cys Met Thr Thr Leu Val Thr Val Glu Ala Glu Tyr Pro Phe Asn
    50                  55                  60

Gln Ser Pro Val Val Thr Arg Ser Cys Ser Ser Cys Val Ala Thr
65                  70                  75                  80

Asp Pro Asp Ser Ile Gly Ala Ala His Leu Ile Phe Cys Cys Phe Arg
                85                  90                  95

Asp Leu Cys Asn Ser Glu Leu
            100

<210> SEQ ID NO 2
<211> LENGTH: 102
<212> TYPE: PRT
<213> ORGANISM: Mus musculus

<400> SEQUENCE: 2

Met Thr Leu Arg Trp Ala Met Trp Leu Leu Leu Ala Ala Trp Ser
1               5                   10                  15

Met Gly Tyr Gly Glu Ala Phe Arg Cys Tyr Thr Cys Glu Gln Pro Thr
            20                  25                  30

Ala Ile Asn Ser Cys Lys Asn Ile Ala Gln Cys Lys Met Glu Asp Thr
        35                  40                  45

Ala Cys Lys Thr Val Leu Glu Thr Val Glu Ala Ala Phe Pro Phe Asn
    50                  55                  60

His Ser Pro Met Val Thr Arg Ser Cys Ser Ser Cys Leu Ala Thr
65                  70                  75                  80

Asp Pro Asp Gly Ile Gly Val Ala His Pro Val Phe Cys Cys Phe Arg
                85                  90                  95

Asp Leu Cys Asn Ser Gly
            100

<210> SEQ ID NO 3
<211> LENGTH: 530
<212> TYPE: DNA
<213> ORGANISM: Homo sapiens

<400> SEQUENCE: 3
ctctcatcac ttctgagcac ggagcaatgg cctctcgctg ggctgtgcag ctgctgctcg      60
tggcagcctg gagcatgggc tgtggtgagg ccctcaagtg ctacacctgc aaggagccca    120
tgaccagtgc ttcctgcagg accattaccc gctgcaagcc agaggacaca gcctgcatga    180
ccacgctggt gacggtggag gcagagtacc ccttcaacca gagccccgtg gtgacccgct    240
cctgctccag ctcctgtgtg gccaccgacc ccgacagcat cggggccgcc cacctgatct    300
tctgctgctt ccgagacctc tgcaactcgg aactctgaac ccagggcggc agggcggaag    360

```
gtgctcctca ggcacctcct ctctgacggg gcctggctcc acctgtgatc acctcccct       420 gcttcctgct gctgtggcac agctcactca tggggtctga ggggagagaa gcacaccagg       480
ggcgccctct gccttccata ccccacgctt ataaaacata actaagccaa                 530
```

```
<210> SEQ ID NO 4
<211> LENGTH: 525
<212> TYPE: DNA
<213> ORGANISM: Mus musculus

<400> SEQUENCE: 4
agggctccta gctcctgagc actgaagaat gacccttcgc tgggccatgt ggctgctgct       60
cttggcagcc tggagcatgg gctatggtga ggccttccga tgctatacct gtgagcagcc      120
cacggccatt aactcatgca agaatattgc tcagtgcaag atggaagaca cagcctgtaa      180
gactgtactg gagacagtgg aagcagcgtt ccccttcaac cacagtccca tggtgacccg      240
ctcctgctcc agctcgtgtc tggccaccga ccctgatggc attggcgttg cccatcctgt      300
cttctgttgc ttccgtgacc tctgcaactc agggtttcca ggcttcgtgg caggcctcta      360
gccacacagg gagcctcctc gttccttctc tatccactct cccggcaggg cccggtgctg      420
cctgcagtcg tctctacatg cctggatcta tgagcagagc tcactgagcc tcaggtcact      480
cactgtccac caagcttgtg gaaaataaaa taaaccaagg gcgaa                      525
```

```
<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
tttatcaggc aggcagatat aaagc                                            25
```

```
<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
attcttcagt gctcaggagc t                                                21
```

```
<210> SEQ ID NO 7
<211> LENGTH: 549
<212> TYPE: DNA
<213> ORGANISM: Mus musculus

<400> SEQUENCE: 7
ctcacagcac ctataccaca tcaggtactc cctcctttcc atactggctc agcctctact       60
ttgtgagtac atctgggtgc atagtagatc ggtcttaggc agatgggata cagtgaggtt      120
ccttttatca ggcagatata aagcagcctt gtacctgagc tcagggggtt ctcgggacct      180
gactatctgg cctattggat gcattcacat agctgaggca agaggctcat ctgagagcca      240
gttgagccag gctctaaaag gcttcctcag ttgagggaca gcagagcatg gtgtcgagta      300
ctggaggtgc accagcagaa gcaggaccaa gactcccaga cagaggttcc ccaaaaggtc      360
catagagggg ccccaccctg ggatggtagg tgatgatggc tcccatccac cacccacacc      420
```

```
cctagccctg tgcctcccta ctgagtcact ctggtcctgc caacacccag aagccgaagc    480
cggaggctga gtataaaatc ctcactatga ggccagccag ggctcctagc tcctgagcac    540
tgaagaatg                                                            549
```